(12) United States Patent
Mullick et al.

(10) Patent No.: US 8,877,062 B2
(45) Date of Patent: Nov. 4, 2014

(54) ANTITHROMBOGENIC HOLLOW FIBER MEMBRANES AND FILTERS

(75) Inventors: Sanjoy Mullick, Brampton (CA); Weilun Chang, Toronto (CA); Hanje Chen, Toronto (CA); Mark Steedman, Toronto (CA); Roseita Esfand, Mississauga (CA)

(73) Assignee: Interface Biologics, Inc., Toronto (CA)

( * ) Notice: Subject to any disclaimer, the term of this patent is extended or adjusted under 35 U.S.C. 154(b) by 480 days.

(21) Appl. No.: 12/834,730

(22) Filed: Jul. 12, 2010

(65) Prior Publication Data

US 2011/0009799 A1 Jan. 13, 2011

Related U.S. Application Data

(63) Continuation-in-part of application No. 12/780,200, filed on May 14, 2010, now abandoned.

(60) Provisional application No. 61/178,861, filed on May 15, 2009.

(51) Int. Cl.
*A61M 1/16* (2006.01)
*A61M 1/34* (2006.01)
(Continued)

(52) U.S. Cl.
CPC ........... *B01D 63/023* (2013.01); *A61M 1/3672* (2013.01); *B01D 63/022* (2013.01); *B01D*
(Continued)

(58) Field of Classification Search
CPC ...... B01D 61/20; B01D 61/28; B01D 61/246; B01D 63/04; B01D 69/08; B01D 71/06; B01D 71/26; B01D 71/44; B01D 71/54; B01D 71/68; B01D 71/76; B01D 71/80; B01D 71/82; B01D 2313/04; B01D 2323/10; B01D 2323/28; B01D 2323/36; A61M 1/16; A61M 1/34; A61M 1/3672; A61M 2001/1623; A61M 2001/34

USPC ............ 210/500.23, 500.24, 500.27, 500.36, 210/500.41, 500.42, 321.61, 321.78, 210/321.79, 321.8, 321.87, 321.88, 321.89, 210/500.43; 604/5.01, 6.01, 6.09, 19

See application file for complete search history.

(56) References Cited

U.S. PATENT DOCUMENTS 3,392,183 A 7/1968 Windemuth et al.
3,427,366 A 2/1969 Ryan et al.
(Continued)

FOREIGN PATENT DOCUMENTS

CN 1711127 A 12/2005
CN 1894302 A 1/2007
(Continued)

OTHER PUBLICATIONS

U.S. Appl. No. 12/780,200, filed May 14, 2010, Mullick et al.
(Continued)

*Primary Examiner* — Joseph Drodge
(74) *Attorney, Agent, or Firm* — Clark & Elbing LLP; Kristina Bieker-Brady

(57) ABSTRACT

The invention relates to extracorporeal blood circuits, and components thereof (e.g., hollow fiber membranes, potted bundles, and blood tubing), including 0.005% to 10% (w/w) surface modifying macromolecule. The extracorporeal blood circuits have an antithrombogenic surface and can be used in hemofiltration, hemodialysis, hemodiafiltration, hemoconcentration, blood oxygenation, and related uses.

41 Claims, 31 Drawing Sheets

(51) Int. Cl.

| | | |
|---|---|---|
| *B01D 61/20* | (2006.01) | |
| *B01D 61/28* | (2006.01) | |
| *B01D 71/06* | (2006.01) | |
| *B01D 71/26* | (2006.01) | |
| *B01D 71/44* | (2006.01) | |
| *B01D 71/68* | (2006.01) | |
| *B01D 71/76* | (2006.01) | |
| *B01D 63/02* | (2006.01) | |
| *A61M 1/36* | (2006.01) | |
| *B01D 67/00* | (2006.01) | |
| *B01D 69/02* | (2006.01) | |
| *B01D 69/08* | (2006.01) | |
| *B29C 47/00* | (2006.01) | |
| *B29L 23/00* | (2006.01) | |
| *B29L 31/00* | (2006.01) | |

(52) U.S. Cl.
CPC ..... 67/0093 (2013.01); *B01D 69/02* (2013.01); *B01D 69/08* (2013.01); *B01D 69/087* (2013.01); *B01D 71/44* (2013.01); *B01D 71/68* (2013.01); *B29C 47/00* (2013.01); *B29C 47/0014* (2013.01); *B29C 47/0026* (2013.01); *B29L 2023/00* (2013.01); *B29L 2031/731* (2013.01); *B01D 2323/30* (2013.01)
USPC ............... 210/645; 210/321.61; 210/321.89; 210/500.23; 210/500.27; 210/500.41; 210/500.43; 210/646; 604/5.01; 604/6.01; 604/6.09; 604/19

(56) References Cited

U.S. PATENT DOCUMENTS

| | | | |
|---|---|---|---|
| 3,872,058 A | | 3/1975 | Gresham |
| 4,312,907 A | | 1/1982 | Hiraoka et al. |
| 4,424,311 A | * | 1/1984 | Nagaoka et al. ............ 525/303 |
| 4,584,362 A | | 4/1986 | Leckart et al. |
| 4,661,530 A | | 4/1987 | Gogolewski et al. |
| 4,742,090 A | | 5/1988 | Hunter et al. |
| 4,743,629 A | * | 5/1988 | Karakelle et al. ............ 521/175 |
| 4,788,083 A | | 11/1988 | Dammann et al. |
| 4,792,354 A | | 12/1988 | Matsuo et al. |
| 4,861,830 A | | 8/1989 | Ward |
| 4,879,032 A | | 11/1989 | Zemlin |
| 4,966,699 A | * | 10/1990 | Sasaki et al. ............... 210/321.8 |
| 4,994,503 A | | 2/1991 | Harris et al. |
| 5,064,871 A | | 11/1991 | Sciangola |
| 5,145,727 A | | 9/1992 | Potts et al. |
| 5,149,576 A | | 9/1992 | Potts et al. |
| 5,242,995 A | | 9/1993 | Kim et al. |
| 5,395,525 A | | 3/1995 | Takano et al. |
| 5,428,123 A | * | 6/1995 | Ward et al. ..................... 528/28 |
| 5,486,570 A | | 1/1996 | St. Clair |
| 5,542,200 A | | 8/1996 | Matsuoka |
| 5,543,200 A | | 8/1996 | Hargis et al. |
| 5,589,563 A | | 12/1996 | Ward et al. |
| 5,779,897 A | | 7/1998 | Kalthod et al. |
| 5,908,701 A | | 6/1999 | Jennings et al. |
| 5,929,201 A | | 7/1999 | Gibbons et al. |
| 5,954,966 A | * | 9/1999 | Matsuura et al. ............ 210/640 |
| 6,111,049 A | | 8/2000 | Sendijarevic et al. |
| 6,127,485 A | | 10/2000 | Klun et al. |
| 6,127,507 A | | 10/2000 | Santerre |
| 6,254,645 B1 | | 7/2001 | Kellis, Jr. et al. |
| 6,348,152 B1 | * | 2/2002 | Kawahara et al. ....... 210/500.24 |
| 6,353,057 B1 | | 3/2002 | He et al. |
| 6,448,364 B1 | | 9/2002 | Clatty et al. |
| 6,685,832 B2 | * | 2/2004 | Mahendran et al. ....... 210/321.8 |
| 8,071,683 B2 | | 12/2011 | Mullick et al. |
| 8,178,620 B2 | | 5/2012 | Mullick et al. |
| 2004/0121175 A1 | | 6/2004 | Flexman et al. |
| 2004/0234575 A1 | * | 11/2004 | Horres et al. ................. 424/426 |
| 2005/0176893 A1 | * | 8/2005 | Rana et al. ................... 525/242 |
| 2007/0037891 A1 | * | 2/2007 | Esfand et al. ............... 514/772.1 |
| 2008/0228253 A1 | | 9/2008 | Mullick et al. |
| 2008/0237127 A1 | * | 10/2008 | Okafuji et al. ................ 210/646 |
| 2009/0211968 A1 | | 8/2009 | Ho et al. |
| 2011/0009799 A1 | | 1/2011 | Mullick et al. |
| 2011/0207893 A1 | | 8/2011 | Mullick et al. |
| 2012/0148774 A1 | | 6/2012 | Mullick et al. |
| 2012/0220724 A1 | | 8/2012 | Mullick et al. |

FOREIGN PATENT DOCUMENTS

| | | |
|---|---|---|
| EP | 0 068 509 | 1/1983 |
| EP | 0 073 978 | 3/1983 |
| EP | 0 231 927 | 2/1987 |
| EP | 0 332 261 | 9/1989 |
| EP | 0 335 664 | 10/1989 |
| EP | 0 615 778 | 9/1994 |
| EP | 0 894 823 | 2/1999 |
| JP | S612868 A | 1/1986 |
| JP | 2000-317275 A | 11/2000 |
| JP | 2004-248904 A | 9/2004 |
| RU | 2215012 | 10/2003 |
| WO | WO95/26993 | 10/1995 |
| WO | WO97/06195 | 2/1997 |
| WO | WO98/34718 | 8/1998 |
| WO | WO2004/056459 | 7/2004 |
| WO | WO2007/084514 | 7/2007 |
| WO | WO2008/076345 | 6/2008 |
| WO | 2010/000746 | 1/2010 |
| WO | WO2010/025398 | 3/2010 |
| WO | WO2011/072398 | 6/2011 |

OTHER PUBLICATIONS

U.S. Appl. No. 12/834,730, filed Jul. 12, 2010, Mullick et al.

BioInterface 2011 Conference Agenda (available at sib.affiniscape.com/cde.cfm?event=331217& addEventId=331217), with text of abstracts from presentations by Cai, "Carboxyl-Ebselen-Based Layer-by-Layer Film: A Potential Antithrombotic and Antimicrobial Coating" (Oct. 25, 2011); Cook, "Surface Modifications with Improved Long-Term Hemocompatability" (Oct. 25, 2011); Dirks, "Non-Adhesive and Antimicrobial Coatings for Medical Implants" (Oct. 26, 2011); and Strokowski, "Adsorption and Hemocompatibility Properties of Elastin-like Polypeptide Surfaces" (Oct. 25, 2011).

Engelberg et al., "Physico-Mechanical Properties of Degradable Polymers Used in Medical Applications: A Comparative Study," *Biomaterials*, 12: 292-304 (1991).

Fang, "Separation of Liquid Mixtures by Membranes," *Department of Chemical Engineering, University of Ottawa*, Canada, ON, 1996.

Goldberg, "Elastomeric Polycarbonate Block Copolymers," *Journal of Polymer Science: Part C*, 4: 707-730 (1963).

Ho et al., "The Effect of Fluorinated Surface Modifying Macromolecules on the Surface Morphology of Polyethersulfone Membranes," *J. Biomater. Sci.* 11(10): 1085-1104, 2004.

Ho, "The Effects of Surface Modifying Macromolecules on the Blood Compatibility of Polyethersulfone Membranes Intended for Biomedical Applications," *Graduate Department of Chemical Engineering and Applied Chemistry, University of Toronto*, 1997.

Jin et al., "Thermotropic Liquid Crystalline Polyesters With Rigid or Flexible Spacer Groups," *The British Polymer Journal*. 132-146 (1980).

Kakimoto et al., "Preparation and Properties of Fluorine-Containing Polyarylates From Tetrafluoroisophthaloyl Chloride and Bisphenols," *Journal of Polymer Science: Part A: Polymer Chemistry*, 25: 2747-2753 (1987).

Khayet et al., "Application of Surface Modifying Macromolecules for the Preparation of Membranes for Membrane Distillation," *Desalination 158*: 51-56, 2003.

Khayet et al., "Design of Novel Direct Contact Membrane Distillation Membranes," *Desalination 192*: 105-111, 2006.

Kim et al., "Application of Surface Modifying Macromolecules in Poly(Ether Suflone) Ultrafiltration Membranes: Influence on Surface Morphology," *Research Study, University of Ottawa and Myongji University*, Korea (6 pages).

(56) References Cited

OTHER PUBLICATIONS

Kulesza et al., "Thermal Decomposition of Bisphenol A-Based Polyetherurethanes Blown With Pentane Part I-Thermal and Pyrolytical Studies," *J. Anal. Appl. Pyrolysis*, 76: 243-248 (2006).
La Mantia et al., "Thermo-Mechanical Degradation of Polymer Blends," *Die Angewandte Makromolekulare Chemie*, 216: 45-65 (1994).
Liaw et al., "Curing Kinetics of Epoxy Resins Based on Bisphenol-S and its Derivatives," *Die Angewandte Makromolekulare Chemie*, 200: 137-146 (1992).
Liaw et al., "Synthesis of Epoxy Resins Based on Bisphenol-S and its Derivatives," *Die Angewandte Makromolekulare Chemie*, 199: 171-190 (1992).
Liaw et al., "Radical Polymerization of Mono- and Di-Methacrylic Esters Containing Bisphenol-S," *Die Angewandte Makromolekulare Chemie*, 207: 43-52 (1993).
Liaw et al., "Curing of Acrylated Epoxy Resin Based on Bisphenol-S," *Polymer Engineering and Science*, 34(16): 1297-1303 (1994).
Liaw, "The Relative Physical and Thermal Properties of Polyurethane Elastomers: Effect of Chain Extenders of Bisphenols, Diisocyanate, and Polyol Structures," *Journal of Applied Polymer Science*, 66: 1251-1265 (1997).
Marks, "Interfacial Synthesis and Characterization of Random and Segmented Block Bisphenol A-Tetrabromobisphenol A Copolycarbonates," *Journal of Applied Polymer Science*, 52: 467-481 (1994).
Maruyama et al., "Synthesis and Properties of Polyarylates From 2,2-Bis(4-hydroxyphenyl)-1,1,1,3,3,3- Hexafluoropropane and Aromatic Diacid Chlorides," *Journal of Polymer Science: Part A: Polymer Chemistry*, 24: 3555-3558 (1986).
Maruyama et al., "Synthesis and Properties of Fluorine-Containing Aromatic Polybenzoxazoles from Bis(o-aminophenols) and Aromatic Diacid Chlorides by the Silylation Method," *Macromolecules*, 21(8): 2305-2309 (1988).
Mitsui NOTIO™ Nano-crystal Structure Controlled Elastomer (available at www.mitsuichemicals.com/ otion.htm#).
Mohd-Norddin et al., "Charged Surface Modifying Macromolecules in Polymer Electrolyte Membrane," *Jurnal Teknologi* 49(F): 91-102, 2008.
Nagata et al., "Synthesis and Properties of Polyamides Derived from Systematically Halogenated Terephthalic Acids with Fluorine, Chlorine, or Bromine Atoms," *Journal of Polymer Science: Part A: Polymer Chemistry*, 26: 235-245 (1988).
Shimizu et al., "Synthesis and Characterization of Fluorine-Countaining Aromatic Polyethers From Tetrafluoroisophthalonitrile and Bisphenols," *Journal of Polymer Science: Part A: Polymer Chemistry*, 25: 2385-2393 (1987).
Suk et al., "Study on the Kinetics of Surface Migration of Surface Modifying Macromolecules in Membrane Preparation," *Macromolecules* 35: 3017-3021, 2002.
Suk et al., "Effects of Surface Modifying Macromolecule (SMM) on the Properties of polyethersulfone Membranes," *Desalination 149*: 303-307, 2002.
Sukumar et al., "Synthesis and Thermal Studies of Block Copolymers from NR and MDI-Based Polyurethanes," *Journal of Applied Polymer Science*, 111: 19-28 (2009).
Tang et al., "Surface Modifying Macromolecules for Improved Resistance of Polyurethanes to Biodegradation," *Canadian Biomaterials Society Meeting*, Quebec City, QC, 1994.
Tang et al., "The Use of Surface Modifying Macromolecules to Inhibit Biodegradation of Segmented Polyurethanes," *Society for Biomaterials*, Boston, MA, 1994.
Tang, "Surface Modifying Macromolecules for Biomaterials," *Department of Chemical Engineering, University of Ottawa*, 1995.
Tang et al., "Synthesis of Surface-Modifying Macromolecules for use in Segmented Polyurethanes," *Journal of Applied Polymer Science*, 62:1133-1145 (1996).
Tang et al., "Use of Surface-Modifying Macromolecules to Enhance the Biostability of Segmented Polyurethanes," *Journal of Biomedical Materials Research Part A*, 35:371-381 (1997).
Office Action pertaining to U.S. Appl. No. 08/690,108 mailed Oct. 31, 1997.
Office Action pertaining to U.S. Appl. No. 08/690,108 mailed Apr. 24, 1998.
Examination Report issued for European Patent Application No. 96 925 626.2-2115, dated Dec. 15, 1998.
Examination Report issued for European Patent Application No. 96 925 626.2-2115, dated Apr. 30, 1999.
Office Action pertaining to U.S. Appl. No. 09/198,268, mailed May 12, 1999.
Office Action pertaining to U.S. Appl. No. 09/198,268, mailed Jan. 21, 2000.
Examination Report issued for European Patent Application No. 96 925 626.2-2115, dated Feb. 17, 2000.
International Search Report and Written Opinion (PCT/US07/25577) mailed Apr. 17, 2008.
International Preliminary Report on Patentability for PCT/US07/25577 issued Jun. 16, 2009.
International Search Report and Written Opinion for PCT/US2009/055418, dated Oct. 20, 2009.
Office Action pertaining to U.S. Appl. No. 12/002,226 mailed Jan. 26, 2010.
Extended European Search Report from European Patent Application No. 07862900.3, dated Jul. 27, 2010.
Office Action pertaining to U.S. Appl. No. 12/002,226 mailed Oct. 5, 2010.
European Search Report issued for European Patent Application No. 10014044, dated Jan. 26, 2011.
International Preliminary Report on Patentability for PCT/US2009/055418, dated Mar. 1, 2011.
European Search Report for European Patent No. 07862900.3, dated Jun. 20, 2011.
European Search Report for European Patent No. 07862900.3, dated Mar. 28, 2012.
Office Action for U.S. Appl. No. 13/323,427 dated Apr. 9, 2012.
Office Action for Chinese Application No. 200980142814.7, mailed Jul. 4, 2012.
Office Action for U.S. Appl. No. 13/060,542 dated Jul. 5, 2012.
English Translation of the Second Office Action for Chinese Patent Application No. 201080001316,2 , mailed Apr. 17, 2014 (21 pages).
English Translation of First Office Action for Chinese Patent Application No. 201080001316.2, mailed Sep. 12, 2013 (17 pages).
First Office Action for European Patent Application No. 10014044.1, mailed Nov. 8, 2013 (4 pages).
Second Office Action for European Patent Application No. 10014044.1, mailed Apr. 24, 2014 (5 pages).
Office Action for Canadian Patent Application No, 2,716,502, mailed Feb. 19, 2014 (2 pages).
Office Action for Australian Patent Application No. 2010224421, mailed May 23, 2014 (3 pages).
English Translation of Final Office Action for Japanese Patent Application No. 2013-516412, mailed Jun. 17, 2014 (4 pages).
English Translation of First Office Action for Japanese Patent Application No. 2013-516412, mailed Dec. 17, 2014 (5 pages).

\* cited by examiner

VIII-b
PTMO = Poly(tetramethylene oxide) Diol

VIII-d
PLN = (Polyethylene Glycol – Polypropylene Glycol- Polyethylene Glycol) Diol IX-a
PCN = Poly(2,2 dimethyl -1-3 propylcarbonate) Diol X-a
PCN = Poly(2,2 dimethyl -1-3 propylcarbonate) Diol X-b
PHCN = Poly(hexamethylene carbonate) diol KI-a
C22- = (Propylene Oxide-Polydimethyl Siloxane-Propylene Oxide) Diol XII-a
HLB = Hydrogenated – Hydroxyl terminated Polybutadiene Diol XII-b
HLB = Hydrogenated – Hydroxyl terminated Polybutadiene Diol XIII-a
HLB = Hydrogenated – Hydroxyl terminated Polybutadiene Diol XIII-b
HLB = Hydrogenated – Hydroxyl terminated Polybutadiene Diol XIII-c
HLB = Hydrogenated – Hydroxyl terminated Polybutadiene Diol XIII-d
H-HTPI = Hydrogenated – Hydroxyl terminated Polyisoprene Diol XIV-a
PDP = (Diethylene Glycol- Ortho Phthalic Anhydride Polyester Ester) Diol XIV-b
PEGA = Poly(diethylene glycol) adipate diol Average change in Pr: Control vs. VII-a and XI-a (n = 6)
Average Gamma Count/10: Control vs. VII-a and XI-a (n = 6)

ANTITHROMBOGENIC HOLLOW FIBER MEMBRANES AND FILTERS

CROSS-REFERENCE TO RELATED APPLICATIONS

This application is a continuation-in-part of U.S. application Ser. No. 12/780,200, filed May 14, 2010, which claims benefit from U.S. Provisional Application No. 61/178,861, filed May 15, 2009, hereby incorporated by reference.

BACKGROUND OF THE INVENTION

The invention relates to antithrombogenic extracorporeal blood circuits and components thereof, such as hollow fiber membranes, blood tubing, and filters, and their use in hemofiltration, hemodialysis, hemodiafiltration, hemoconcentration, blood oxygenation, and related uses.

For a treatment of a patient suffering from renal failure, various blood purifying methods have been proposed in which blood is taken out from the living body of the patient to be purified and the purified blood is then returned into the body. For example, the blood purification methods utilizing extracorporeal circulation are classified into the following types: hemodialysis (HD) by diffusion, hemofiltration (HF) which performs body fluid removal/substitution by ultrafiltration, and hemodiafiltration (HDF) in which HD and HF are combined.

The above-mentioned methods are implemented using a hemodialyzer. The dialyzer is the piece of equipment that actually filters the blood of waste solutes and fluids (e.g., urea, potassium, creatinine, and uric acid). Almost all dialyzers in use today are of the hollow-fiber variety. A cylindrical bundle of hollow fibers, whose walls are composed of semi-permeable membrane, is anchored at each end into potting compound (a sort of glue). This assembly is then put into a clear plastic cylindrical shell with four openings. One opening or blood port at each end of the cylinder communicates with each end of the bundle of hollow fibers. This forms the "blood compartment" of the dialyzer. Two other ports are cut into the side of the cylinder. These communicate with the space around the hollow fibers, the "dialysate compartment." Blood is pumped via the blood ports through this bundle of very thin capillary-like tubes, and the dialysate is pumped through the space surrounding the fibers. Pressure gradients are applied when necessary to move fluid from the blood to the dialysate compartment.

Hemodialysis is an important procedure that plays the role of an artificial kidney and replaces all vital functions due to chronic or acute kidney failure. The dialyzer may be used for the treatment of patients with renal failure, fluid overload, or toxemic conditions, and can be configured to perform HD, HF, HDF, or hemoconcentration.

While the blood is being transported to and from the body or cleaned in the dialyzer, an anticoagulant, such as heparin, may be added to prevent clotting or thrombosis. For patients receiving continuous renal replacement therapy (CRRT) (i.e., continuous dialysis 24 hours/7 days a week), heparin is typically given as a bolus systemically to prevent clogging of filter membranes during dialysis due to coagulation of blood. In cases where no heparin is administered filters clog 27% of the time, while with heparin filters clog 17% of the time (see Richardson et al., Kidney International 70:963-968 (2006)). For patients receiving intermittent hemodialysis (IHD) (intermittent dialysis of about 4 hours twice daily), typically no heparin is administered. During IHD the filters clog 20-30% of time (see Manns et al., Critical Care Medicine 31:449-455 (2003)). When the filters clog, the dialysis procedure is interrupted, and the filters are flushed with saline solution to clear the thrombus. In patients undergoing chronic hemodialysis (e.g., hemodialysis for extended hours at a time and with multiple sessions during a week) it is common to use heparin in bolus amounts to reduce the rate of filter clogging.

While advantageous, the use of heparin in some patients can be complicated by allergic reactions and bleeding, and can be contraindicated for use in patients taking certain medications.

Some medical procedures require the use of extracorporeal oxygenating methods, where blood is taken out from the living body of the patient to be oxygenated and the oxygenated blood is then returned to the body. For example, oxygenator devices implementing such extracorporeal oxygenating methods include heart-lung bypass units or extracorporeal membrane oxygenation (ECMO) machines used during open heart surgery, such as coronary artery bypass grafting (CABG) and cardiac valve replacement, or used to treat respiratory distress syndrome or respiratory insufficiencies. During open heart surgery, devices for hemoconcentration can also be used to increase various blood components within the patient, thus minimizing the risk of post-operative bleeding. These hemoconcentrators can be used in-line with an extracorporeal circuit that includes an oxygenator device, such as a heart-lung bypass unit.

Based on these treatments that require the use of pumping blood out of and into a patient, there is a need for extracorporeal blood circuits that have reduced thrombogenicity. In particular, there is a need for methods and compositions to provide a polymeric component of an extracorporeal blood circuit with a surface that minimizes the rate of thrombosis upon exposure to blood.

SUMMARY OF THE INVENTION

The methods and compositions of the invention features extracorporeal blood circuits, and components thereof (e.g., hollow fiber membranes, potted bundles, and blood tubing), including 0.005% to 10% (w/w) surface modifying macromolecule.

In a first aspect, the invention features an extracorporeal blood circuit including a polymeric component, where the polymeric component includes a base polymer admixed with from 0.005% to 10% (w/w) of a surface modifying macromolecule (e.g., from 0.005% to 0.1% (w/w), from 0.005% to 5% (w/w), from 0.1% to 0.3% (w/w), from 0.1% to 5% (w/w), from 0.1% to 10% (w/w), from 0.05% to 5% (w/w), 0.05% to 8% (w/w), from 1% to 5% (w/w), from 1% to 8% (w/w), from 1% to 10% (w/w), and from 2% to 10% (w/w)), where the polymeric component has a surface positioned to contact the blood when the extracorporeal blood circuit is in use, and where the surface is antithrombogenic when contacted with the blood. In one embodiment, the thrombi deposition at the surface is reduced by at least 10%, 20%, 40%, 60%, or 80% (e.g., from 10% to 95%, from 10% to 80%, from 20% to 95%, from 35% to 85%, or from 40% to 80%) when contacted with blood. In another embodiment, the extracorporeal blood circuit has an increased average functional working life of at least 110%, 125%, 150%, 200%, or 400% (e.g., from 110% to 1,000%, from 200% to 900%, or from 300% to 900%). In yet another embodiment, the extracorporeal blood circuit reduces adverse advents in a subject receiving blood passing through the extracorporeal blood circuit.

Any of the extracorporeal blood circuits described herein can include one or more of: a hollow fiber membrane of the invention; a potted bundle of the invention; or a blood tubing of the invention.

In a second aspect, the invention features a hollow fiber membrane, the hollow fiber membrane including a base polymer admixed with from 0.005% to 10% (w/w) surface modifying macromolecule (e.g., from 0.005% to 0.1% (w/w), from 0.005% to 5% (w/w), from 0.1% to 0.3% (w/w), from 0.1% to 5% (w/w), from 0.1% to 10% (w/w), from 0.05% to 5% (w/w), 0.05% to 8% (w/w), from 1% to 5% (w/w), from 1% to 8% (w/w), from 1% to 10% (w/w), and from 2% to 10% (w/w)), where the hollow fiber membrane is antithrombogenic when contacted with blood. In one embodiment, the thrombi deposition on the hollow fiber membrane is reduced by at least 10%, 20%, 40%, 60%, or 80% (e.g., from 10% to 95%, from 10% to 80%, from 20% to 95%, from 35% to 85%, or from 40% to 80%) when contacted with blood. In another embodiment, the hollow fiber membrane has an operating pressure after 4 hours of use that is reduced by at least 10%, 20%, 30%, 40%, or 50% (e.g., from 10% to 95%, from 10% to 80%, from 20% to 75%, from 25% to 45%, or from 30% to 80%). In yet another embodiment, the hollow fiber membrane reduces adverse advents in a subject receiving blood passing through the hollow fiber membrane. In certain embodiments, the base polymer is selected from the group consisting of a polysulfone (e.g., poly(oxy-1,4-phenylene sulfonyl-1,4-phenyleneoxy-1,4-phenyleneisopropylidene-1,4-phenylene) or polyether sulfone), a polyacrylonitrile, a cellulose acetate, a cellulose di- or tri-acetate, a polyimide, a poly(methyl methacrylate), a polycarbonate, a polyamide, a polypropylene, and a polyethylene. In further embodiments, the hollow fiber membrane further includes a hydrophilic pore forming agent (e.g., polyvinylpyrrolidone, ethylene glycol, alcohols, polypropylene glycol, and polyethylene glycol, or mixtures thereof). In one embodiment, the hollow fiber membrane includes from 80% to 96.5% (w/w) (e.g., from 80% to 95%, from 80% to 90% (w/w), from 85% to 90% (w/w), and from 90% to 95% (w/w)) of the base polymer, from 3% to 20% (w/w) (e.g., from 3% to 15% (w/w), from 3% to 7% (w/w), from 3% to 5% (w/w), and from 5% to 10% (w/w)) of the hydrophilic pore forming agent, and 0.005% to 10% (w/w) (e.g., from 0.005% to 0.1% (w/w), from 0.005% to 5% (w/w), from 0.1% to 0.3% (w/w), from 0.1% to 5% (w/w), from 0.1% to 10% (w/w), from 0.05% to 5% (w/w), 0.05% to 8% (w/w), from 1% to 5% (w/w), from 1% to 8% (w/w), from 1% to 10% (w/w), and from 2% to 10% (w/w)) of the surface modifying macromolecule.

In a third aspect, the invention features a potted bundle of hollow fiber membranes within an encasement including: (a) an array of hollow fiber membranes, the array of hollow fiber membranes having lumens, a first set of fiber ends, and a second set of fiber ends; (b) the first set of fiber ends being potted in a potting resin which defines a first internal wall near a first end of the encasement; and (c) the second set of fiber ends being potted in a potting resin which defines a second internal wall near a second end of the encasement, where the lumens of the hollow fiber membranes provide a path for the flow of blood from the first internal wall to the second internal wall, and where the potting resin includes from 0.005% to 10% (w/w) surface modifying macromolecule (e.g., from 0.005% to 0.1% (w/w), from 0.005% to 5% (w/w), from 0.1% to 0.3% (w/w), from 0.1% to 5% (w/w), from 0.1% to 10% (w/w), from 0.05% to 5% (w/w), 0.05% to 8% (w/w), from 1% to 5% (w/w), from 1% to 8% (w/w), from 1% to 10% (w/w), and from 2% to 10% (w/w)). In certain embodiments, the bundle has a prolonged working life. In some embodiments, the bundle has an increased average functional working life of at least 110%, 125%, 150%, 200%, or 400% (e.g., from 110% to 1,000%, from 125% to 1,000%, from 200% to 900%, or from 300% to 900%). In other embodiments, the thrombi deposition on the potted bundle is reduced by at least 10%, 20%, 40%, 60%, or 80% (e.g., from 10% to 95%, from 10% to 80%, from 20% to 95%, from 35% to 85%, or from 40% to 80%) when contacted with blood. In still other embodiments, the bundle has an operating pressure after 4 hours of use that is reduced by at least 10%, 20%, 30%, 40%, or 50% (e.g., from 10% to 95%, from 10% to 80%, from 20% to 75%, from 25% to 45%, or from 30% to 80%). In some embodiment, the potted bundle reduces adverse advents in a subject receiving blood passing through the potted bundle. In other embodiments, the potting resin is antithrombogenic when contacted with blood.

In one embodiment, the bundle of potted hollow fiber membranes within an encasement is part of a blood purification device (e.g., hemodialysis, hemodiafiltration, hemofiltration, hemoconcentration, or oxygenator device). In yet another embodiment, the potting resin is a cross-linked polyurethane (e.g., a cross-linked polyurethane formed from 4'-methylene bis(cyclohexyl isocyanate; 2,2'-methylene bis (phenyl) isocyanate; 2,4'-methylene bis(phenyl) isocyanate; or 4,4'-methylene bis(phenyl) isocyanate).

In another aspect, the invention features a dialysis filter including any hollow fiber membrane described herein or any potted bundle described herein, where the filter has a prolonged working life. In one embodiment, the dialysis filter reduces adverse advents in a subject receiving blood passing through the dialysis filter.

In another aspect, the invention features a blood tubing including a base polymer (e.g., polyvinyl chloride) admixed with from 0.005% to 10% (w/w) (e.g., from 0.005% to 0.1% (w/w), from 0.005% to 5% (w/w), from 0.1% to 0.3% (w/w), from 0.1% to 5% (w/w), from 0.1% to 10% (w/w), from 0.05% to 5% (w/w), 0.05% to 8% (w/w), from 1% to 5% (w/w), from 1% to 8% (w/w), from 1% to 10% (w/w), and from 2% to 10% (w/w)) surface modifying macromolecule, where the blood tubing is antithrombogenic when contacted with blood. In a particular embodiment, the base polymer includes polyvinyl chloride. In one embodiment, the blood tubing reduces adverse advents in a subject receiving blood passing through the blood tubing. In one embodiment, the thrombi deposition at the surface of the blood tubing is reduced by at least 10%, 20%, 40%, 60%, or 80% (e.g., from 10% to 95%, from 10% to 80%, from 20% to 95%, from 35% to 85%, or from 40% to 80%) when contacted with blood. In another embodiment, the blood tubing has an increased average functional working life of at least 110%, 125%, 150%, 200%, or 400% (e.g., from 110% to 1,000%, from 125% to 1,000%, from 200% to 900%, or from 300% to 900%).

The invention further features method for treating a subject suffering from impaired kidney function, the method including performing a procedure selected from hemodialysis, hemofiltration, hemoconcentration, or hemodiafiltration on the subject using a dialysis filter, where the filter includes any hollow fiber membrane described herein or any potted bundle described herein. In one embodiment, during the procedure the subject receives less than a standard dose of anticoagulant (e.g., where during the procedure the subject receives no anticoagulant). In another embodiment, the filter has a prolonged working life. In yet another embodiment, the filter has an increased average functional working life of at least 110%, 125%, 150%, 200%, or 400% (e.g., from 110% to 1,000%, from 125% to 1,000%, from 200% to 900%, or from 300% to 900%). In one embodiment, the thrombi deposition on the filter is reduced by at least 10%, 20%, 40%, 60%, or 80% (e.g., from 10% to 95%, from 10% to 80%, from 20% to 95%, from 35% to 85%, or from 40% to 80%) when contacted with blood. In another embodiment, the filter has an operating pressure after 4 hours of use that is reduced by at least 10%, 20%, 30%, 40%, or 50% (e.g., from 10% to 95%, from 10% to 80%, from 20% to 75%, from 25% to 45%, or from 30% to 80%). In yet another embodiment, the adverse events experienced by the subject are reduced.

The invention features a method for treating a subject suffering from impaired cardiac function, the method including performing a surgery selected from a coronary artery bypass grafting and a cardiac valve replacement using an oxygenator device, where the oxygenator device includes any hollow fiber membrane described herein or any potted bundle described herein. In one embodiment, during the procedure the subject receives less than a standard dose of anticoagulant (e.g., where during the procedure the subject receives no anticoagulant). In another embodiment, the adverse events experienced by the subject are reduced.

The invention features a method for treating a subject, said method including withdrawing blood from, and returning blood to, said subject via any extracorporeal blood circuit described herein. In one embodiment, during the procedure the subject receives less than a standard dose of anticoagulant (e.g., where during the procedure the subject receives no anticoagulant). In another embodiment, the adverse events experienced by the subject are reduced.

The invention also features a method for purifying a protein in blood, a blood product (e.g., plasma or fractionated blood component), or a combination thereof, the method including dialyzing the blood, the blood product, or the combination thereof across any hollow fiber membrane described herein or any potted bundle described herein.

The invention features a hollow fiber plasma purification membrane, including any bundle of potted hollow fiber membranes described herein.

The invention also features a spinning solution for preparing a hollow fiber membrane, the spinning solution including (i) from 57% to 87% (w/w) (e.g., from 57% to 85% (w/w), from 70% to 87% (w/w), and from 70% to 85% (w/w)) of an aprotic solvent; (ii) from 10% to 25% (w/w) (e.g., from 10% to 20% (w/w), from 12% to 25% (w/w), and from 12% to 20% (w/w)) of base polymer; (iii) from 0.005% to 8% (w/w) (e.g., from 0.005% to 5% (w/w), from 0.005% to 3% (w/w), 0.005% to 2% (w/w), from 0.01% to 3% (w/w), and from 0.01% to 2% (w/w)) of surface modifying macromolecule; and (iv) from 3% to 10% (w/w) (e.g., from 3% to 7% (w/w), from 3% to 5% (w/w), and from 5% to 10% (w/w)) of hydrophilic pore forming agent. In certain embodiments, the aprotic solvent is selected from dimethylformamide, dimethylsulfoxide, dimethylacetamide, N-methylpyrrolidone, and mixtures thereof. In other embodiments, the aprotic solvent further includes less than 25% (v/v) (i.e., from 1% to 25% (v/v), 1% to 15% (v/v), or 5% to 20% (v/v)) of a low boiling solvent selected from tetrahydrofuran, diethylether, methylethyl ketone, acetone, and mixtures thereof. In still other embodiments, the hydrophilic pore forming agent is polyvinylpyrrolidone. The spinning solution can be processed as described herein to produce a hollow fiber membrane of the invention.

The invention features a method for making a hollow fiber membrane including the steps of: (a) preparing a homogeneous spinning solution of the invention; and (b) extruding the homogeneous spinning solution from an outer annular orifice of a tube-in-orifice spinneret into an aqueous solution to form the hollow fiber membrane.

The invention also features a method of potting hollow fiber membranes including the steps of: (a) forming a bundle of hollow fiber membranes, the bundle of hollow fiber membranes having lumens, a first set of fiber ends, and a second set of fiber ends; (b) placing the first set of fiber ends and the second set of fiber ends in an uncured potting liquid; (c) curing the potting liquid to form a potting resin in which the hollow fiber membranes are potted; (d) cutting the potting resin and fiber ends to form a first wall in which the first set of fiber ends is potted and a second wall in which the second set of fiber ends is potted; and (e) heating the first wall and the second wall (i.e., heating to facilitate the migration of surface modifying macromolecule to the surface of the wall), where the potting liquid includes from 0.005% to 10% (w/w) (e.g., from 0.005% to 0.1% (w/w), from 0.005% to 5% (w/w), from 0.1% to 0.3% (w/w), from 0.1% to 5% (w/w), from 0.1% to 10% (w/w), from 0.05% to 5% (w/w), 0.05% to 8% (w/w), from 1% to 5% (w/w), from 1% to 8% (w/w), from 1% to 10% (w/w), and from 2% to 10% (w/w)) surface modifying macromolecule.

The invention features a dialysis kit including (i) a hollow fiber membrane of the invention, a potted bundle of the invention, a dialysis filter of the invention, and/or blood tubing of the invention; and (ii) instructions for performing dialysis on a subject receiving less than a standard dose of anticoagulant (e.g., receiving no anticoagulant).

In any of the hollow fiber membranes described herein, the surface modifying macromolecule is selected from VII-a, VIII-a, VIII-b, VIII-c, VIII-d, IX-a, X-a, X-b, XI-a, XI-b, XII-a, XII-b, XIII-a, XIII-b, XIII-c, XIII-d, XIV-a, and XIV-b.

In one embodiment, the potting resin includes a surface modifying macromolecule selected from VII-a, VIII-a, IX-a, XI-a, VIII-d, and XI-b.

In another embodiment, the blood tubing includes a surface modifying macromolecule selected from VII-a, XIV-a, and XIV-b.

In any of the extracorporeal blood circuits, hollow fiber membranes (or potted bundles thereof or plasma purification membranes thereof), potting materials (e.g., potting resin or potting liquid), blood tubings, dialysis filters, spinning solutions, methods, systems, and kits, the surface modifying macromolecule is described by any of the formulas (I)-(XIV) below.

(1)

$$F_T\text{-(oligo)-}F_T \tag{I}$$

wherein $F_T$ is a polyfluoroorgano group and oligo is an oligomeric segment.

(2)

wherein
(i) $F_T$ is a polyfluoroorgano group covalently attached to LinkB;
(ii) C is a chain terminating group;
(iii) Oligo is an oligomeric segment;
(iv) LinkB is a coupling segment; and
(v) a is an integer greater than 0.

(3)

$$F_T\text{-[B-(oligo)]}_n\text{-B-}F_T \tag{III}$$

wherein
(i) B includes a urethane;
(ii) oligo includes polypropylene oxide, polyethylene oxide, or polytetramethylene oxide;
(iii) $F_T$ is a polyfluoroorgano group; and
(iv) n is an integer from 1 to 10.

(4)

  (IV)

wherein
(i) A is a soft segment including hydrogenated polybutadiene, poly(2,2 dimethyl-1-3-propylcarbonate), polybutadiene, poly(diethylene glycol)adipate, poly(hexamethylene carbonate), poly(ethylene-co-butylene), neopentyl glycol-ortho phthalic anhydride polyester, diethylene glycol-ortho phthalic anhydride polyester, 1,6-hexanediol-ortho phthalic anhydride polyester, or bisphenol A ethoxylate;
(ii) B is a hard segment including a urethane; and
(iii) $F_T$ is a polyfluoroorgano group, and
(iv) n is an integer from 1 to 10.

(5)

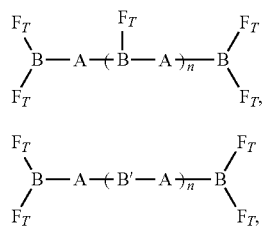  (V)
(VI)

wherein
(i) A is a soft segment;
(ii) B is a hard segment including a isocyanurate trimer or biuret trimer;
(iii) each $F_T$ is a polyfluoroorgano group; and
(iv) n is an integer between 0 to 10.

(6)

  (VII)

wherein
(i) Oligo is an oligomeric segment including polypropylene oxide, polyethylene oxide, or polytetramethyleneoxide and having a theoretical molecular weight of from 500 to 3,000 Daltons (e.g., from 500 to 2,000 Daltons, from 1,000 to 2,000 Daltons, or from 1,000 to 3,000 Daltons);
(ii) B is a hard segment formed from an isocyanate dimer;
(iii) $F_T$ is a polyfluoroorgano group; and
(iv) n is an integer from 1 to 10.

(7)

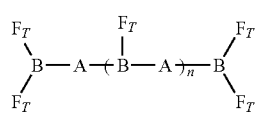  (VIII)

wherein
(i) A is an oligomeric segment including polypropylene oxide, polyethylene oxide, polytetramethyleneoxide, or mixtures thereof, and having a theoretical molecular weight of from 500 to 3,000 Daltons (e.g., from 500 to 2,000 Daltons, from 1,000 to 2,000 Daltons, or from 1,000 to 3,000 Daltons);

(ii) B is a hard segment including an isocyanurate trimer or biuret trimer;
(iii) $F_T$ is a polyfluoroorgano group; and
(iv) n is an integer from 0 to 10.

(8)

  (IX)

wherein
(i) Oligo is a polycarbonate polyol having a theoretical molecular weight of from 500 to 3,000 Daltons (e.g., from 500 to 2,000 Daltons, from 1,000 to 2,000 Daltons, or from 1,000 to 3,000 Daltons);
(ii) B is a hard segment formed from an isocyanate dimer;
(iii) $F_T$ is a polyfluoroorgano group; and
(iv) n is an integer from 1 to 10.

(9)

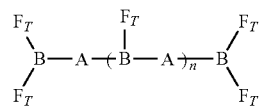  (X)

wherein
(i) A is an oligomeric segment including a polycarbonate polyol having a theoretical molecular weight of from 500 to 3,000 Daltons (e.g., from 500 to 2,000 Daltons, from 1,000 to 2,000 Daltons, or from 1,000 to 3,000 Daltons);
(ii) B is a hard segment including an isocyanurate trimer or biuret trimer;
(iii) $F_T$ is a polyfluoroorgano group; and
(iv) n is an integer from 0 to 10.

(10)

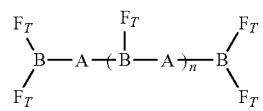  (XI)

wherein
(i) A includes a first block segment selected from polypropylene oxide, polyethylene oxide, polytetramethyleneoxide, or mixtures thereof, and a second block segment including a polysiloxane or polydimethylsiloxane, wherein A has a theoretical molecular weight of from 1,000 to 5,000 Daltons (e.g., from 1,000 to 3,000 Daltons, from 2,000 to 5,000 Daltons, or from 2,500 to 5,000 Daltons);
(ii) B is a hard segment including an isocyanurate trimer or biuret trimer;
(iii) $F_T$ is a polyfluoroorgano group; and
(iv) n is an integer from 0 to 10.

(11)

  (XII)

wherein
(i) A is a soft segment selected from hydrogenated polybutadiene
(HLBH) diol (e.g., HLBH diol), polybutadiene (LBHP) diol (e.g., LBHP diol), hydrogenated polyisoprene (HHTPI) diol (e.g., HHTPI diol), and polystyrene and has a theoretical molecular weight of from 750 to 3,500 Daltons (e.g., from 750 to 2,000 Daltons, from 1,000 to 2,500 Daltons, or from 1,000 to 3,500 Daltons);
(ii) B is a hard segment formed from an isocyanate dimer;

(iii) $F_T$ is a polyfluoroorgano group; and
(iv) n is an integer from 1 to 10.

(12)

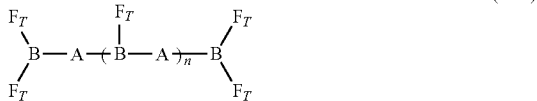

(XIII)

wherein
(i) A is a soft segment selected from hydrogenated polybutadiene (HLBH) diol (e.g., HLBH diol), polybutadiene (LBHP) diol (e.g., LBHP diol), hydrogenated polyisoprene (HHTPI) diol (e.g., HHTPI diol), and polystyrene and has a theoretical molecular weight of from 750 to 3,500 Daltons (e.g., from 750 to 2,000 Daltons, from 1,000 to 2,500 Daltons, or from 1,000 to 3,500 Daltons);
(ii) B is a hard segment including an isocyanurate trimer or biuret trimer;
(iii) $F_T$ is a polyfluoroorgano group; and
(iv) n is an integer from 0 to 10.

(13)

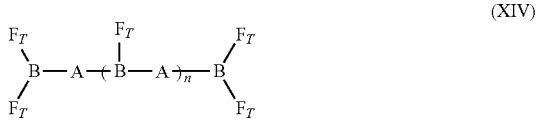

(XIV)

wherein
(i) A is a polyester having a theoretical molecular weight of from 500 to 3,500 Daltons (e.g., from 500 to 2,000 Daltons, from 1,000 to 2,000 Daltons, or from 1,000 to 3,000 Daltons);
(ii) B is a hard segment including an isocyanurate trimer or biuret trimer;
(iii) $F_T$ is a polyfluoroorgano group; and
(iv) n is an integer from 0 to 10.

In certain embodiments, the surface modifying macromolecule of formulas (I) and (II) include an oligo segment that is a branched or non-branched oligomeric segment of fewer than 20 repeating units (e.g., from 2 to 15 units, from 2 to 10 units, from 3 to 15 units, and from 3 to 10 units). In another embodiment, the surface modifying macromolecule of formulas (I) and (II) include an oligomeric segment selected from polyurethane, polyurea, polyamide, polyalkylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polyethylene oxide, polytetramethylene oxide, or polyethylenebutylene segments.

In certain embodiments, the surface modifying macromolecule of formulas (IV) include a hard segment formed from a diisocyanate selected from 3-isocyanatomethyl, 3,5,5-trimethyl cyclohexylisocyanate; 4,4'-methylene bis(cyclohexyl isocyanate); 4,4'-methylene bis(phenyl)isocyanate; toluene-2,4 diisocyanate); m-tetramethylxylene diisocyanate; and hexamethylene diisocyanate; and n is 1 or 2.

In certain embodiments, the surface modifying macromolecule of formulas (V) and (VI) include a soft segment having a theoretical molecular weight of 500 to 3,500 Daltons (e.g., from 500 to 2,000 Daltons, from 1,000 to 2,000 Daltons, or from 1,000 to 3,000 Daltons) and/or the soft segment includes hydrogenated polybutadiene (HLBH), poly(2,2 dimethyl-1-3-propylcarbonate) (PCN), polybutadiene (LBHP), polytetramethylene oxide (PTMO), (propylene)oxide (PPO), diethyleneglycol-orthophthalic anhydride polyester (PDP), hydrogenated polyisoprene (HHTPI), poly(hexamethylene carbonate), poly(2-butyl-2-ethyl-1,3-propyl carbonate), or hydroxylterminated polydimethylsiloxane (C22). In other embodiments of the surface modifying macromolecule of formulas (V) and (VI), the hard segment is formed by reacting a triisocyanate with a diol including the soft segment, wherein the triisocyanate is selected from hexamethylene diisocyanate (HDI) biuret trimer, isophorone diisocyanate (IPDI) trimer, or hexamethylene diisocyanate (HDI) trimer.

In some embodiments of the surface modifying macromolecule of formula (VII), B is a hard segment formed from 3-isocyanatomethyl, 3,5,5-trimethyl cyclohexylisocyanate; 4,4'-methylene bis(cyclohexyl isocyanate); 4,4'-methylene bis(phenyl) isocyanate; toluene-2,4 diisocyanate); m-tetramethylxylene diisocyanate; and hexamethylene diisocyanate; and n is an integer from 1 to 3. In one particular embodiment, the surface modifying macromolecule of formula (VII) is VII-a. The surface modifying macromolecules of formula (VII) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (VII) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

In certain embodiments of the surface modifying macromolecule of formula (VIII), B is a hard segment formed by reacting a triisocyanate with a diol of A (e.g., the oligomeric segment), wherein the triisocyanate is selected from hexamethylene diisocyanate (HDI) biuret trimer, isophorone diisocyanate (IPDI) trimer, and hexamethylene diisocyanate (HDI) trimer; and n is 0, 1, 2, or 3. In one particular embodiment, the surface modifying macromolecule of formula (VIII) is VIII-a, VIII-b, VIII-c, or VIII-d. The surface modifying macromolecules of formula (VIII) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (VIII) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

In certain embodiments of the surface modifying macromolecule of formula (IX), Oligo includes poly (2,2 dimethyl-1-3-propylcarbonate) (PCN) polyol (e.g., PCN diol); B is a hard segment formed from 3-isocyanatomethyl, 3,5,5-trimethyl cyclohexylisocyanate; 4,4'-methylene bis(cyclohexyl isocyanate); 4,4'-methylene bis(phenyl) isocyanate; toluene- 2,4 diisocyanate); m-tetramethylxylene diisocyanate; and hexamethylene diisocyanate; and n is 1, 2, or 3. In one particular embodiment, the surface modifying macromolecule of formula (IX) is IX-a. The surface modifying macromolecules of formula (IX) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (IX) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

In certain embodiments of the surface modifying macromolecule of formula (X), A includes poly (2,2 dimethyl-1-3-propylcarbonate) (PCN) polyol (e.g., PCN diol) or poly(hexamethylene carbonate) (PHCN) polyol; B is a hard segment formed by reacting a triisocyanate with a diol of A (e.g., the oligomeric segment), wherein the triisocyanate is selected from hexamethylene diisocyanate (HDI) biuret trimer, isophorone diisocyanate (IPDI) trimer, and hexamethylene diisocyanate (HDI) trimer; and n is 0, 1, 2, or 3. In one particular embodiment, the surface modifying macromolecule of formula (X) is X-a or X-b. The surface modifying macromolecules of formula (X) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (X) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

In certain embodiments of the surface modifying macromolecule of formula (XI), A is a includes polypropylene oxide and polydimethylsiloxane; B is a hard segment formed by reacting a triisocyanate with a diol of A, wherein the triisocyanate is selected from hexamethylene diisocyanate (HDI) biuret trimer, isophorone diisocyanate (IPDI) trimer, and hexamethylene diisocyanate (HDI) trimer; and n is 0, 1, 2, or 3. In one particular embodiment, the surface modifying macromolecule of formula (XI) is XI-a or XI-b. The surface modifying macromolecules of formula (XI) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (XI) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

In certain embodiments of the surface modifying macromolecule of formula (XII), A includes hydrogenated polybutadiene diol; B is a hard segment formed from 3-isocyanatomethyl, 3,5,5-trimethyl cyclohexylisocyanate); 4,4'-methylene bis(cyclohexyl isocyanate); 4,4'-methylene bis (phenyl) isocyanate; toluene-2,4 diisocyanate); m-tetramethylxylene diisocyanate; and hexamethylene diisocyanate; and n is 1, 2, or 3. In one particular embodiment, the surface modifying macromolecule of formula (XII) is XII-a or XII-b. The surface modifying macromolecules of formula (XII) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (XII) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

In certain embodiments of the surface modifying macromolecule of formula (XIII), A is selected from hydrogenated polybutadiene (HLBH) diol (e.g., HLBH diol), and hydrogenated polyisoprene (HHTPI) diol (e.g., HHTPI diol); B is a hard segment formed by reacting a triisocyanate with a diol of A (e.g., the oligomeric segment), wherein the triisocyanate is selected from hexamethylene diisocyanate (HDI) biuret trimer, isophorone diisocyanate (IPDI) trimer, and hexamethylene diisocyanate (HDI) trimer; and n is 0, 1, 2, or 3. In one particular embodiment, the surface modifying macromolecule of formula (XIII) is XIII-a, XIII-b, XIII-c, or XIII-d. The surface modifying macromolecules of formula (XIII) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (XIII) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

In certain embodiments of the surface modifying macromolecule of formula (XIV), A is selected from poly (diethylene glycol)adipate, neopentyl glycol-ortho phthalic anhydride polyester, diethylene glycol-ortho phthalic anhydride polyester, and 1,6-hexanediol-ortho phthalic anhydride polyester; B is a hard segment formed by reacting a triisocyanate with a diol of A (e.g., the polyester segment), wherein the triisocyanate is selected from hexamethylene diisocyanate (HDI) biuret trimer, isophorone diisocyanate (IPDI) trimer, and hexamethylene diisocyanate (HDI) trimer; and n is 0, 1, 2, or 3. In one particular embodiment, the surface modifying macromolecule of formula (XIV) is XIV-a or XIV-b. The surface modifying macromolecules of formula (XIV) can be used in an extracorporeal blood circuit of the invention, or a component thereof, such as a hollow fiber membrane, potted bundle, blood tubing, or dialysis filter, and in conjunction with any methods, systems, and kits of the invention described herein. For example, the surface modifying macromolecules of formula (XIV) can be added to polyvinyl chloride to make an antithrombogenic blood tubing; added to a potting material to make an antithrombogenic potted bundle; and/or added to the base polymer of a hollow fiber membrane (e.g., a polysulfone, a polyacrylonitrile, a cellulose acetate, a cellulose di- or tri-acetate, a polyimide, a poly(methyl methacrylate), a polycarbonate, a polyamide, a polypropylene, or a polyethylene) to form a hollow fiber membrane that is antithrombogenic when contacted with blood.

For any of the surface modifying macromolecules of the invention formed from an isocyanate dimer, the isocyanate dimers can be selected from 3-isocyanatomethyl, 3,5,5-trimethyl cyclohexylisocyanate; 4,4'-methylene bis(cyclohexyl isocyanate) (HMDI); 2,2'-, 2,4'-, and 4,4'-methylene bis(phenyl) isocyanate (MDI); toluene-2,4 diisocyanate; aromatic aliphatic isocyanate, such 1,2-, 1,3-, and 1,4-xylene diisocyanate; meta-tetramethylxylene diisocyanate (m-TMXDI); para-tetramethylxylene diisocyanate (p-TMXDI); hexamethylene diisocyanate (HDI); ethylene diisocyanate; propylene-1,2-diisocyanate; tetramethylene diisocyanate; tetramethylene-1,4-diisocyanate; octamethylene diisocyanate; decamethylene diisocyanate; 2,2,4-trimethylhexamethylene diisocyanate; 2,4,4-trimethylhexamethylene diisocyanate; dodecane-1,12-diisocyanate; dicyclohexylmethane diisocyanate; cyclobutane-1,3-diisocyanate; cyclohexane-1,2-diisocyanate; cyclohexane-1,3-diisocyanate; cyclohexane-1,4-diisocyanate; methyl-cyclohexylene diisocyanate (HTDI); 2,4-methylcyclohexane diisocyanate; 2,6-methylcyclohexane diisocyanate; 4,4'-dicyclohexyl diisocyanate; 2,4'-dicyclohexyl diisocyanate; 1,3,5-cyclohexane triisocyanate; isocyanatomethylcyclohexane isocyanate; 1-isocyanato-3,3-5-trimethyl-5-isocyanatomethylcyclohexane; isocyanatoethylcyclohexane isocyanate; bis(isocyanatomethyl)-cyclohexane diisocyanate; 4,4'-bis(isocyanatomethyl) dicyclohexane; 2,4'-bis(isocyanatomethyl)dicyclohexane; isophoronediisocyanate (IPDI); 2,4-hexahydrotoluene diisocyanate; 2,6-hexahydrotoluene diisocyanate;3,3'-dimethyl-4,4'-biphenylene diisocyanate (TODI); polymeric MDI; carbodiimide-modified liquid 4,4'-diphenylmethane diisocyanate; para-phenylene diisocyanate (PPDI); meta-phenylene diisocyanate (MPDI); triphenyl methane-4,4'-, and triphenyl methane-4,4"-triisocyanate; naphthylene-1,5-diisocyanate; 2,4'-, 4,4'-, and 2,2-biphenyl diisocyanate; polyphenyl polymethylene polyisocyanate (PMDI); mixtures of MDI and PMDI; mixtures of PMDI and TDI; dimerized uredione of any isocyanate described herein, such as uredione of toluene diisocyanate, uredione of hexamethylene diisocyanate, and mixtures thereof; and substituted and isomeric mixtures thereof.

For any of the surface modifying macromolecules of the invention formed from an isocyanate trimer, the isocyanate trimer can be selected from hexamethylene diisocyanate (HDI) biuret trimer, isophorone diisocyanate (IPDI) trimer, hexamethylene diisocyanate (HDI) trimer; triisocyanate of 2,2,4-trimethyl-1,6-hexane diisocyanate (TMDI); a trimerized isocyanurate of any isocyanates described herein, such as isocyanurate of toluene diisocyanate, trimer of diphenylmethane diisocyanate, trimer of tetramethylxylene diisocyanate, and mixtures thereof; a trimerized biuret of any isocyanates described herein; modified isocyanates derived from the above diisocyanates; and substituted and isomeric mixtures thereof.

In any of formulas (I)-(XIV), the above surface modifying macromolecule includes the group $F_T$ that is a polyfluoroalkyl having a theoretical molecular weight of between 100-1,500 Da. For example, $F_T$ may be selected from the group consisting of radicals of the general formula $CF_3(CF_2)_rCH_2CH_2$—wherein r is 2-20, and $CF_3(CF_2)_s(CH_2CH_2O)_\chi$ wherein $\chi$ is 1-10 and s is 1-20. Alternatively, $F_T$ may be selected from the group consisting of radicals of the general formula $CH_mF_{(3-m)}(CF_2)_rCH_2CH_2$— and $CH_mF_{(3-m)}(CF_2)_s(CH_2CH_2O)_\chi$—, wherein m is 0, 1, 2, or 3; $\chi$ is an integer between 1-10; r is an integer between 2-20; and s is an integer between 1-20. In certain embodiments, $F_T$ is selected from 1H,1H,2H,2H-perfluoro-1-decanol; 1H,1H,2H,2H-perfluoro-1-octanol; 1H,1H,5H-perfluoro-1-pentanol; and 1H,1H, perfluoro-1-butanol, and mixtures thereof. In still other embodiments, $F_T$ is selected from $(CF_3)(CF_2)_5CH_2CH_2O$—, $(CF_3)(CF_2)_2CH_2CH_2O$—, $(CF_3)(CF_2)_5CH_2CH_2O$—, $CHF_2(CF_2)_3CH_2O$—, and $(CF_3)(CF_2)_2CH_2O$—.

In another embodiment, the above surface modifying macromolecule has a theoretical molecular weight of less than 10,000 Daltons (e.g., from 500 to 10,000 Daltons, from 500 to 9,000 Daltons, from 500 to 5,000 Daltons, from 1,000 to 10,000 Daltons, from 1,000 to 6,000 Daltons, or from 1,500 to 8,000 Daltons).

In still another embodiment, the above surface modifying macromolecule includes from 5% to 40% (w/w) of the hard segment (e.g., from 5% to 35% (w/w), from 5% to 30% (w/w), and from 10% to 40% (w/w)), from 20% to 90% (w/w) of the soft segment (e.g., from 20% to 80% (w/w), from 30% to 90% (w/w), and from 40% to 90% (w/w)), and from 5% to 50% (w/w) of the polyfluoroorgano group (e.g., from 5% to 40% (w/w), from 5% to 30% (w/w), and from 10% to 40% (w/w)).

In one embodiment, the above surface modifying macromolecule has a ratio of hard segment to soft segment of from 0.15 to 2.0 (e.g., from 0.15 to 1.8, from 0.15 to 1.5, and from 0.2 to 2.0).

As used herein, the term "antithrombogenic" refers to an extracorporeal blood circuit, or component thereof (e.g., a hollow fiber membrane, blood tubing, dialysis filter, and/or a potted bundle of hollow fiber membranes) for which the rate at which thrombosis occurs upon exposure to whole blood under is reduced in comparison to an otherwise identical extracorporeal blood circuit, or component thereof, that differs only by the absence of a surface modifying macromolecule tested under the same blood-contacting conditions. A reduced rate of thrombosis can be determined by any of the assays and methods described herein. For example, antithrombogenicity can be determined by radiolabeling blood components and measuring the formation of thrombi using, for example, a γ-count to assess the amount of thrombosis occurring at a surface. For the extracorporeal blood circuits, or components thereof, of the invention an average decrease in thrombosis based upon the γ-count can be 70%, 60%, 50%, 40%, 30%, 20%, or 10% of the average thrombosis as determined by γ-count of a reference hollow fiber membrane lacking the surface modifying macromolecule). Alternatively, antithrombogenicity in a filter or hollow fiber membrane can be determined by a reduced operating pressure (e.g., an average decrease in operating pressure at the header of a hollow fiber membrane being reduced by at least 10%, 20%, 30%, 40%, 50%, or 60% in comparison to the average pressure at the header of a reference filter or hollow fiber membrane lacking the surface modifying macromolecule.

By "base polymer" is meant a polymer having a theoretical molecular weight of greater than 50,000 Daltons (e.g., greater than 50,000, 75,000, 100,000, 150,000, 200,000 Daltons).

As used herein, "C" refers to a chain terminating group. Exemplary chain terminating groups include monofunctional groups containing an amine, alcohol, or carboxylic acid functionality.

By "dialysis filter" is meant a filter configured for use in a dialysis machine which can be used by patients suffering from impaired kidney function.

By "hard segment" is meant a portion of the surface modifying macromolecule or a portion of an oligo segment, where the portion includes a urethane group —NH—C(O)O— (e.g., a urethane group formed by reacting an isocyanate with a hydroxyl group of a soft segment diol or a hydroxyl group of a polyfluoroorgano group).

As used herein, the term "increased average functional working life" refers to an average increase in functional working life for an extracorporeal blood circuit, or component thereof, of the invention in comparison to the average working life of an extracorporeal blood circuit, or component thereof, used under the same conditions and differing only by the absence of surface modifying macromolecule, where the working life is determined by the length of time the extracorporeal circuit, or a component thereof, can be used without having to flush thrombi deposits from the extracorporeal circuit, or a component thereof (e.g., working life without a saline flush, or flush with an anticoagulant). The increased average functional working life for an extracorporeal blood circuit, or component thereof, of the invention can be at least 110%, 125%, 150%, 200%, 250%, 300%, or 400% longer than the working life of the reference extracorporeal blood circuit, or component thereof, lacking the surface modifying macromolecule.

By "less than a standard dose of anticoagulant" is meant a reduction in the anticoagulant administered to a subject during hemodialysis when using the dialysis filters of the invention in comparison to the amount used for a dialysis filter that differs only by the absence of a surface modifying macromolecule. A standard dose is generally identified by each institution in a standard operating procedure for a clinical setting, such as for use of an extracorporeal blood circuit, and components thereof. The standard dose of anticoagulant refers to a dose or a range of doses determined by reference to a standard operating procedure of an institution, and a reduced dose is determined as compared to that standard dose. The reduced dose of anticoagulant can be 80%, 70%, 60%, 50%, 40%, 30%, 20%, or 10% of the standard dose of anticoagulant (e.g., heparin or citrate).

As used herein, "LinkB" refers to a coupling segment capable of covalently linking two oligo moieties and a surface active group. Typically, LinkB molecules have molecular weights ranging from 40 to 700. Preferably the LinkB molecules are selected from the group of functionalized diamines, diisocyanates, disulfonic acids, dicarboxylic acids, diacid chlorides and dialdehydes, wherein the functionalized component has secondary functional chemistry that is accessed for chemical attachment of a surface active group. Such secondary groups include, for example, esters, carboxylic acid salts, sulfonic acid salts, phosphonic acid salts, thiols, vinyls and secondary amines. Terminal hydroxyls, amines or carboxylic acids on the oligo intermediates can react with diamines to form oligo-amides; react with diisocyanates to form oligo-urethanes, oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal, oligo-imines.

By "oligo" is meant a relatively short length of a repeating unit or units, generally less than about 50 monomeric units and theoretical molecular weights less than 10,000 Daltons, but preferably <7,000 Daltons and in some examples, <5,000 Daltons. In certain embodiments, oligo is selected from the group consisting of polyurethane, polyurea, polyimide, polyalkylene oxide, polycarbonate, polyester, polylactone, polysilicone, polyethersulfone, polyolefin, polyvinyl, polypeptide, polysaccharide, and ether and amine linked segments thereof.

By "polyethersulfone" is meant a polymer of the formula:

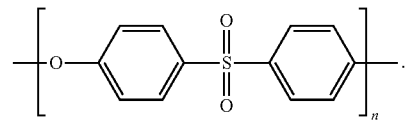

Polyether Sulfone (PES)

This polymer is commercially available under the trade name Radel™ from Amoco Corp.

By "polymeric component" is meant any component within an extracorporeal blood circuit, wherein the component includes a base polymer, as described herein. For example, polymeric components include a hollow fiber membrane, a potted bundle of hollow fiber membranes, a dialysis filter, an oxygenator device, and a blood tubing.

By "poly(oxy-1,4-phenylene sulfonyl-1,4-phenyleneoxy-1,4-phenyleneisopropylidene-1,4-phenylene)" is meant a polymer of the formula:

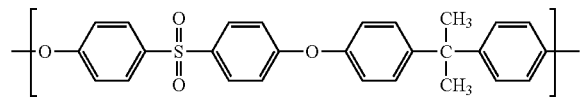

This polymer is commercially available under the trade name Udel™ P-3500 from Solvay Advanced Polymers. For use in the hollow fiber membranes of the invention, a particular size for this polymer may be preferred (i.e., in the range of 30-90 kDa; 45-80 kDa; or 60-80 kDa.).

As used herein, the term "polysulfone" refers to a class of polymers that include as a repeating subunit the moiety -aryl-SO$_2$-aryl-. Polysulfones include, without limitation, polyethersulfones and poly(oxy-1,4-phenylene sulfonyl-1,4-phenyleneoxy-1,4-phenyleneisopropylidene-1,4-phenylene).

By "prolonged working life" is meant a dialysis filter for which the rate at which the filter becomes clogged during a hemodialysis procedure (e.g., and then requiring a saline flush to unclog the filter), is reduced in comparison to a dialysis filter that differs only by the absence of a surface modifying macromolecule used under the same conditions. The prolonged working life for a dialysis filter can be at least 110%, 125%, 150%, 200%, 250%, 300%, or 400% longer than the working life of the reference dialysis filter lacking the surface modifying macromolecule.

As used herein, the term "reduced thrombi deposition" refers to an average decrease in γ-count following a period of use (e.g., 60, 90, 120, 360, or 720 minutes), for an extracorporeal blood circuit, or component thereof, of the invention in comparison to the average γ-count observed for an extracorporeal blood circuit used under the same conditions and differing only by the absence of surface modifying macromolecule. The γ-count is obtained by incorporating surface modifying macromolecule into the extracorporeal blood circuit to provide an antithrombogenic interface between the membrane and the flow of blood passing through the membrane, where γ-count is measured at any treated surface of the circuit and is measured under conditions in which the amount of anticoagulant included in the blood is insufficient to prevent the formation of thrombi in the absence of surface modifying macromolecule. A γ-count can be determined by any of the assays and methods described herein. For example, γ-count can be determined by flowing blood or plasma containing radiolabeled platelets (or other blood components, such as red blood cells) into an extracorporeal blood circuit and measuring the radiation from the radiolabel within the extracorporeal blood circuit. These assays and methods can be performed multiple times to obtain an average γ-count or an average decrease in γ-count. The thrombi deposition for an extracorporeal blood circuit, or component thereof, of the invention can be on average reduced by 10%, 20%, 30, 40%, 50%, 60%, 70%, 80%, 90%, or 95% in comparison to the average thrombi deposition of the extracorporeal blood circuit, or component thereof, lacking the surface modifying macromolecule.

By "reduced operating pressure" is meant an average decrease in operating pressure following a period of use (e.g., 2 hrs, 4 hrs, 8 hrs, 12 hrs, or 16 hrs), for a hollow fiber membrane, or filters or potted bundles thereof, of the invention in comparison to the average pressure observed for a hollow fiber membrane used under the same conditions and differing only by the absence of surface modifying macromolecule. The reduced operating pressure is obtained by incorporating surface modifying macromolecule into the hollow fiber membrane to provide an antithrombogenic interface between the membrane and the flow of blood passing through the membrane, where pressure is measured at the header of the membrane. For an array of hollow fiber membranes having a potting resin at an end of the array, a reduced operating pressure can be obtained by using a surface modifying macromolecule to provide an antithrombogenic interface between the membrane and/or the potting resin and the flow of blood passing through the potted bundle. Operating pressure can be determined by any of the assays and methods described herein. For example, operating pressure can be determined by flowing blood into a hollow fiber membrane and measuring the change in pressure within the hollow fiber membrane over a period of time. These assays and methods can be performed multiple times to obtain an average operating pressure or an average decrease in operating pressure. The reduced operating pressure for a hollow fiber membrane (or filters or potted bundles thereof) of the invention can be less than 10%, 20%, 30%, 40%, 50%, 60%, 70%, or 80% after 2, 4, 8, 12, or 16 hours of use in comparison to the average pressure observed for a reference hollow fiber membrane, filter, or potted bundle lacking the surface modifying macromolecule.

As used herein, the terms "reduces adverse events" and "adverse events experienced by a subject" refer to a number or extent of adverse events experienced by a subject connected to an extracorporeal blood circuit, or component thereof, of the invention, where such adverse events are reduced or decreased during or after a period of use, in comparison to an extracorporeal blood circuit, or component, used under the same conditions and differing only by the absence of surface modifying macromolecule. The number or extent of adverse events can be determined by any useful method, including the use of animal models (see Livigni et al., Critical Care 10:R151 (2006); Walker et al., Artificial Organs 8:329-333 (1984); Cheung, Blood Purification 5:155-161 (1987); Kamler et al., Journal of Thoracic and Cardiovascular Surgery 49:157-161 (2001); and Kamler et al., European Journal of Cardio-Thoracic Surgery 11:973-980 (1997)). Adverse events include bleeding (e.g., measured by the activated clotting time), hemolysis, reduced blood cell counts, severe hemodynamic instability, embolism, thromboembolism, a thrombi-related event, and any other event requiring that the subject take an erythropoiesis-stimulating agent (e.g., erythropoietin and/or intravenous iron). The presence of one or more adverse events can be indicative of the presence of thrombi or the activation of blood complements in the coagulation cascade.

By "soft segment" is meant a portion of the surface modifying macromolecule or a portion of an oligo segment, where the portion includes an ether group, an ester group (e.g., a polyester), an alkyl group, a carbonate group, a siloxane group, or a mixture thereof. For example, the soft segment can have a theoretical molecular weight or average molecular weight from 500 to 3,000 Daltons (e.g., from 500 to 2,000 Daltons, from 1,000 to 2,000 Daltons, or from 1,000 to 3,000 Daltons).

As used herein, "surface modifying macromolecule" refers to the macromolecules containing polyfluoroorgano groups and described herein by formulas (I)-(XIV) and in U.S. Pat. No. 6,127,507; in U.S. Patent Publication No. 20080228253; and in U.S. Provisional Ser. No. 61/092,667, filed Aug. 28, 2008, each of which is incorporated herein by reference. Surface modifying macromolecules can be prepared as described in U.S. Pat. No. 6,127,507; U.S. Patent Publication No. 20080228253; and PCT Publication No. WO/2010/025398, filed Aug. 28, 2009. Briefly, surface modifying macromolecules, such as XI-a and X-a, may be synthesized from a polyisocyanate (e.g., Desmodur N3200 or Desmodur Z4470) reacted dropwise with a fluoroalkyl alcohol in an organic solvent (e.g., anhydrous THF or DMAC) in the presence of a catalyst at 25° C. for 2 hours. After addition of the fluorinated alcohol, stirring is continued for 1 hour at 50° C. and for a further 1 hour at 70° C. These steps lead to the formation of a partially fluorinated intermediate which is then coupled with a polyol soft segment (e.g., polydimethylsiloxane diol or poly(2,2 dimethyl-1-3-propyl carbonate)diol) at 70° C. over a period of 14 hours to provide the surface modifying macromolecule. Because the reactions are moisture sensitive, they are typically carried out under an inert $N_2$ atmosphere and under anhydrous conditions. The reaction product is precipitated in 1% MeOH/water mixture and then washed several times with water, and the surface modifying macromolecule is dried prior to use. The soft segment of the surface modifying macromolecule can function as an anchor for the surface modifying macromolecule within the base polymer substrate upon admixture. The surface active groups are responsible, in part, for carrying the surface modifying macromolecule to the surface of the admixture, where the surface active groups are exposed on the surface. The migration of the surface modifying macromolecules to the surface is a dynamic process and is dependent on the surface environment. The process of migration is driven by the tendency towards establishing a low surface energy at the mixture's surface. When the balance between anchoring and surface migration is achieved, the surface modifying macromolecule remains stable at the surface of the polymer, while simultaneously altering surface properties.

This invention features blood circuits which can be useful for reducing platelet adhesion, reducing occlusion, reducing the need for heparin and/or other anticoagulants, reducing the costs associated with certain medical procedures, such as dialysis, prolonging the working life of the blood circuit, improving patient safety, and reducing waste.

Other features and advantages of the invention will be apparent from the Drawings, Detailed Description, and the claims.

BRIEF DESCRIPTION OF THE DRAWINGS

FIG. 20A is a scanning electron micrograph of a single hollow fiber depicting the outer surface, the inner surface, and the fiber thickness. FIG. 20B is an illustration of bundle of hollow fibers arranged in the header part of the dialyzer cartridge with the potting area (areas indicated by arrow labeled "Potted area untreated" in the inner lumen of the dialyzer cartridge, including the thick dotted line within the inner lumen of the dialyzer cartridge and the areas marked with an X) exposed.

FIG. 24A shows thrombi formed at the inlet of the hemofilters. FIG. 24B shows thrombi formed at the outlet of the hemofilters.

FIG. 25A shows thrombi formed at the inlet of the control hemofilter (no surface modification). FIG. 25B shows thrombi formed at the outlet of the control hemofilter (no surface modification). FIG. 25C shows residue on the sieve after draining blood.

FIG. 26A shows thrombi formed at the inlet of the hemofilters. FIG. 26B shows thrombi formed at the outlet of the hemofilters. A control hemofilter showed complete occlusion, where close-ups are provided for the inlet (FIG. 26C) and outlet (FIG. 26D) for control.

FIG. 28A shows thrombi formed at the inlet of the hemofilters. FIG. 28B shows thrombi formed at the outlet of the hemofilters.

FIG. 29A shows thrombi formed at the inlet of the hemofilters. FIG. 29B shows thrombi formed at the outlet of the hemofilters.

FIG. 30A shows thrombi formed at the inlet of the hemofilters. FIG. 30B shows thrombi formed at the outlet of the hemofilters.

FIG. 31A shows thrombi formed at the inlet of the hemofilters. FIG. 31B shows thrombi formed at the outlet of the hemofilters.

DETAILED DESCRIPTION

Figure 1:
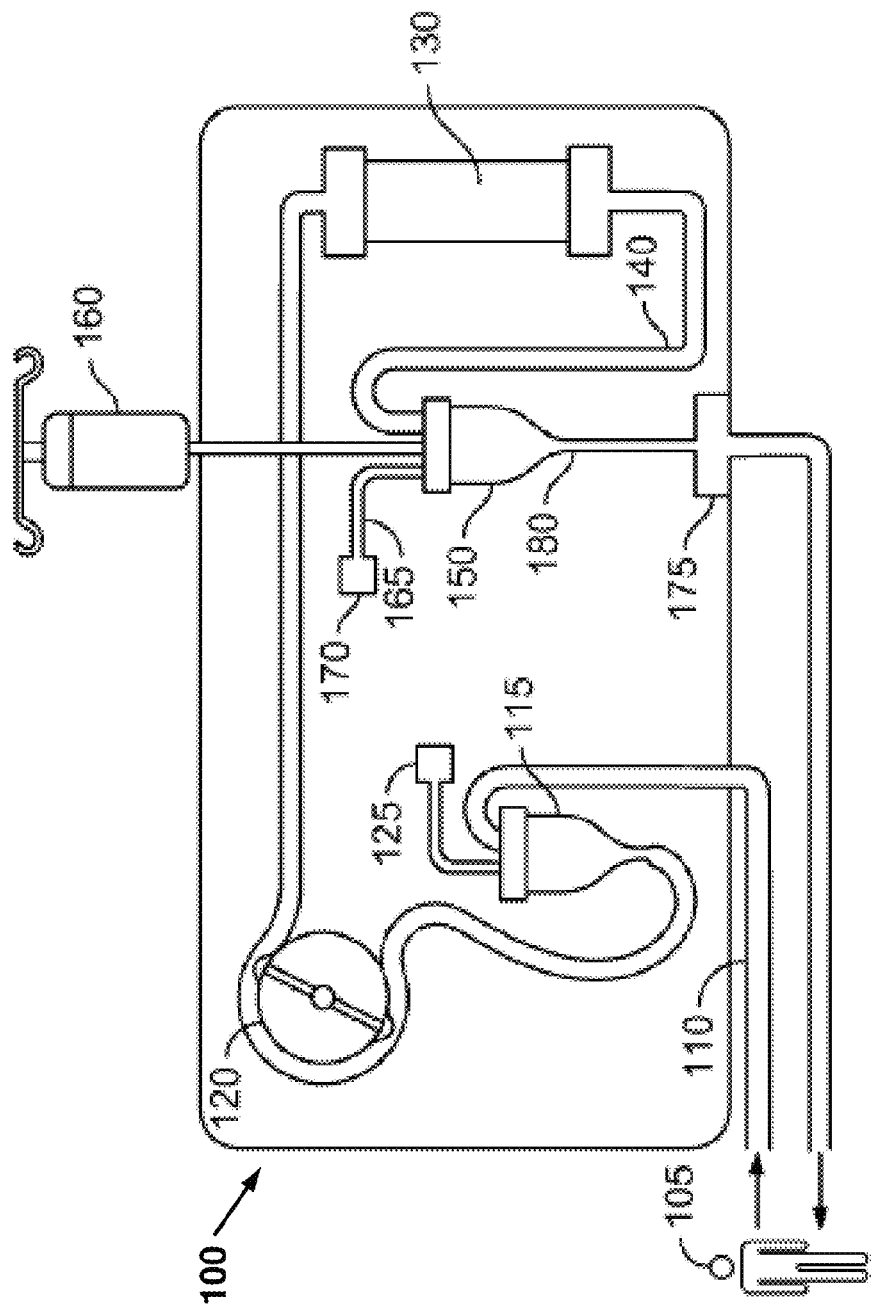
FIG. 1 is a schematic of an exemplary extracorporeal blood circuit.
Figure 2:
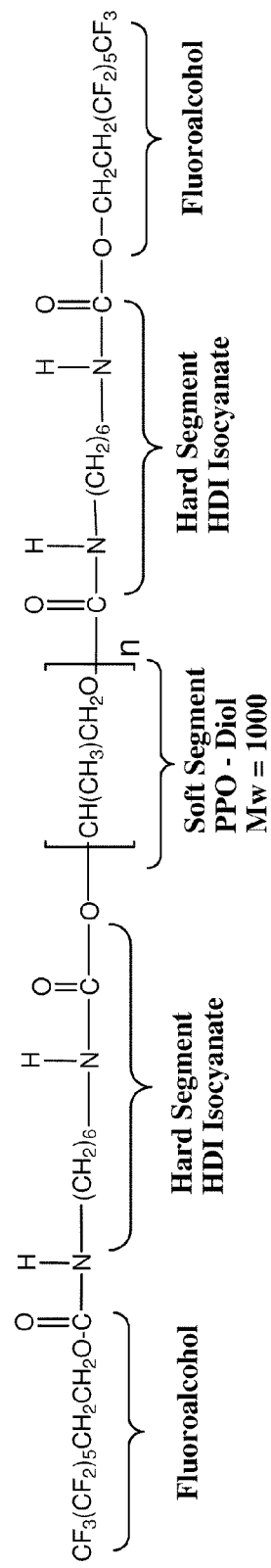
FIG. 2 is an illustration depicting surface modifying macromolecule VII-a of the invention.
Figure 3:
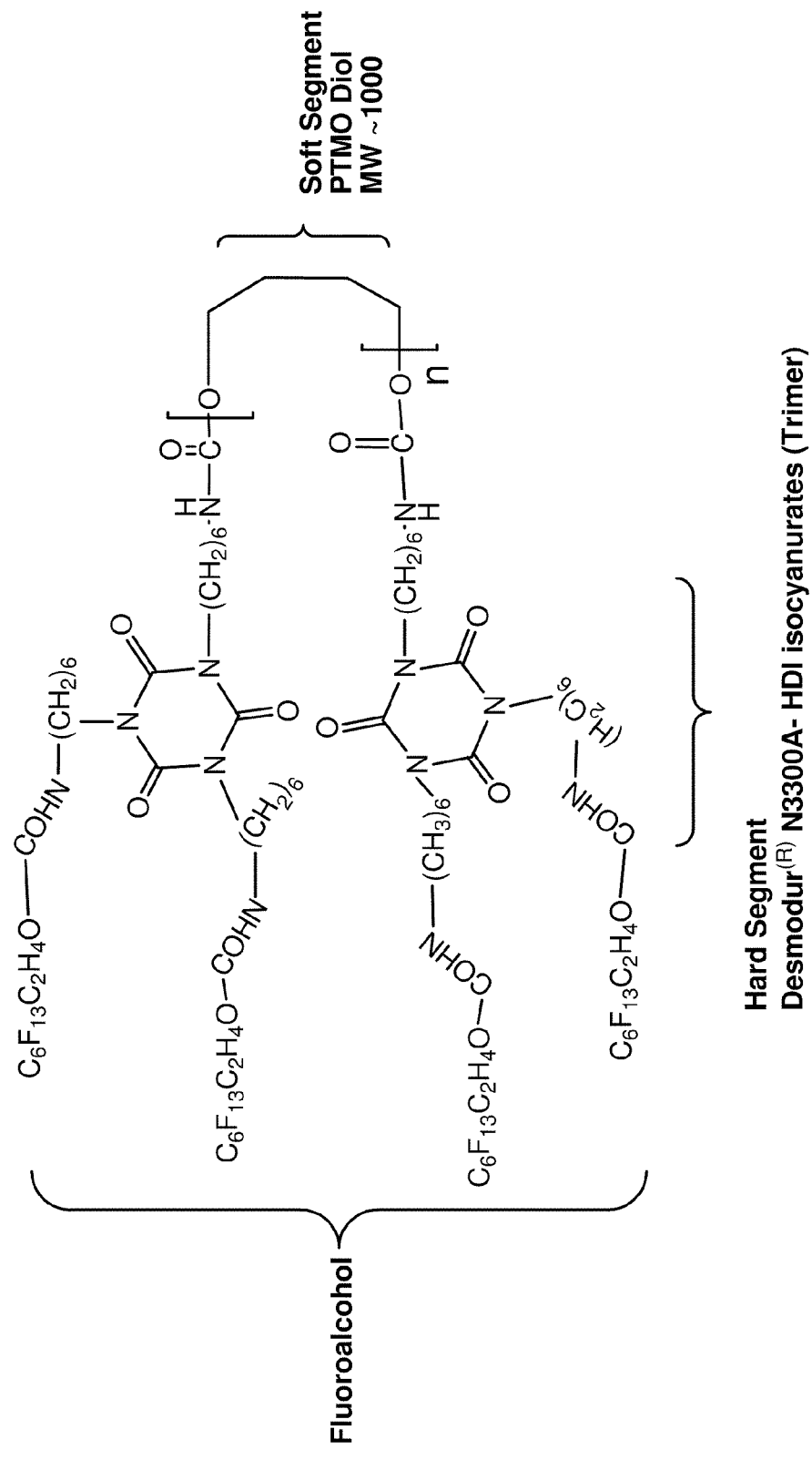
FIG. 3 is an illustration depicting surface modifying macromolecule VIII-a of the invention.
Figure 4:
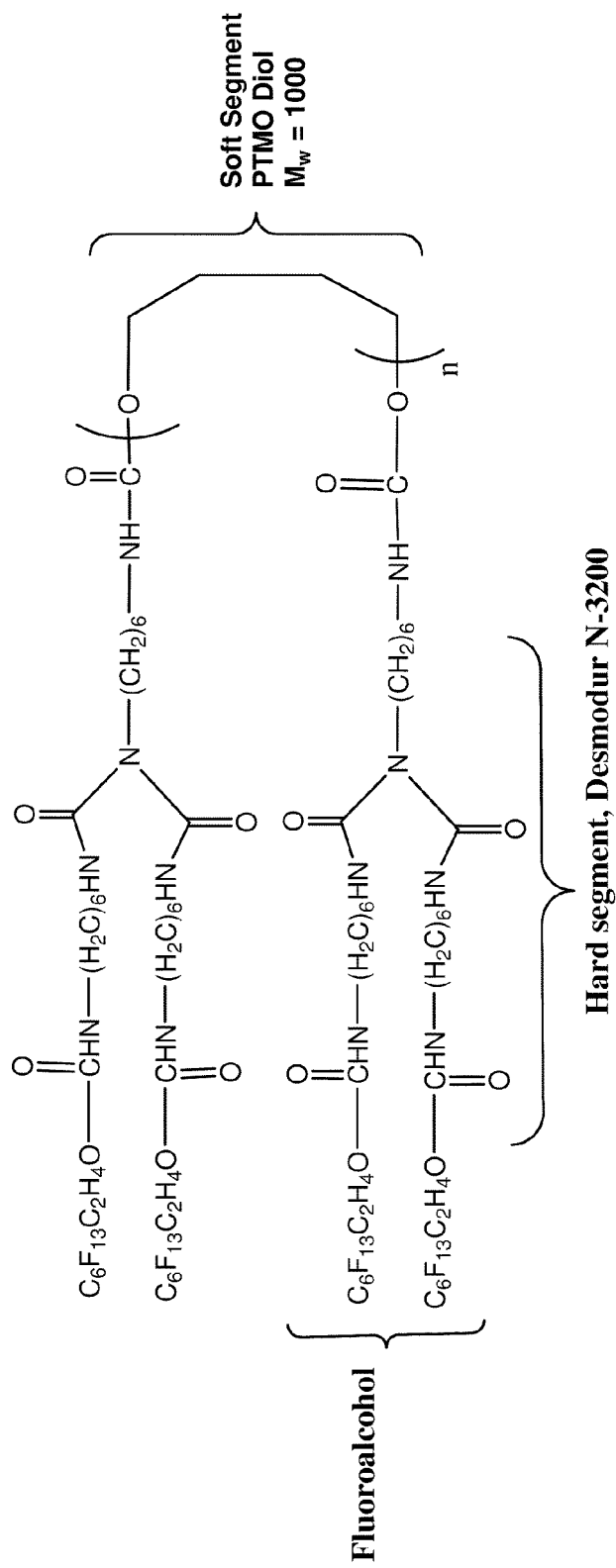
FIG. 4 is an illustration depicting surface modifying macromolecule VIII-b of the invention.
Figure 5:
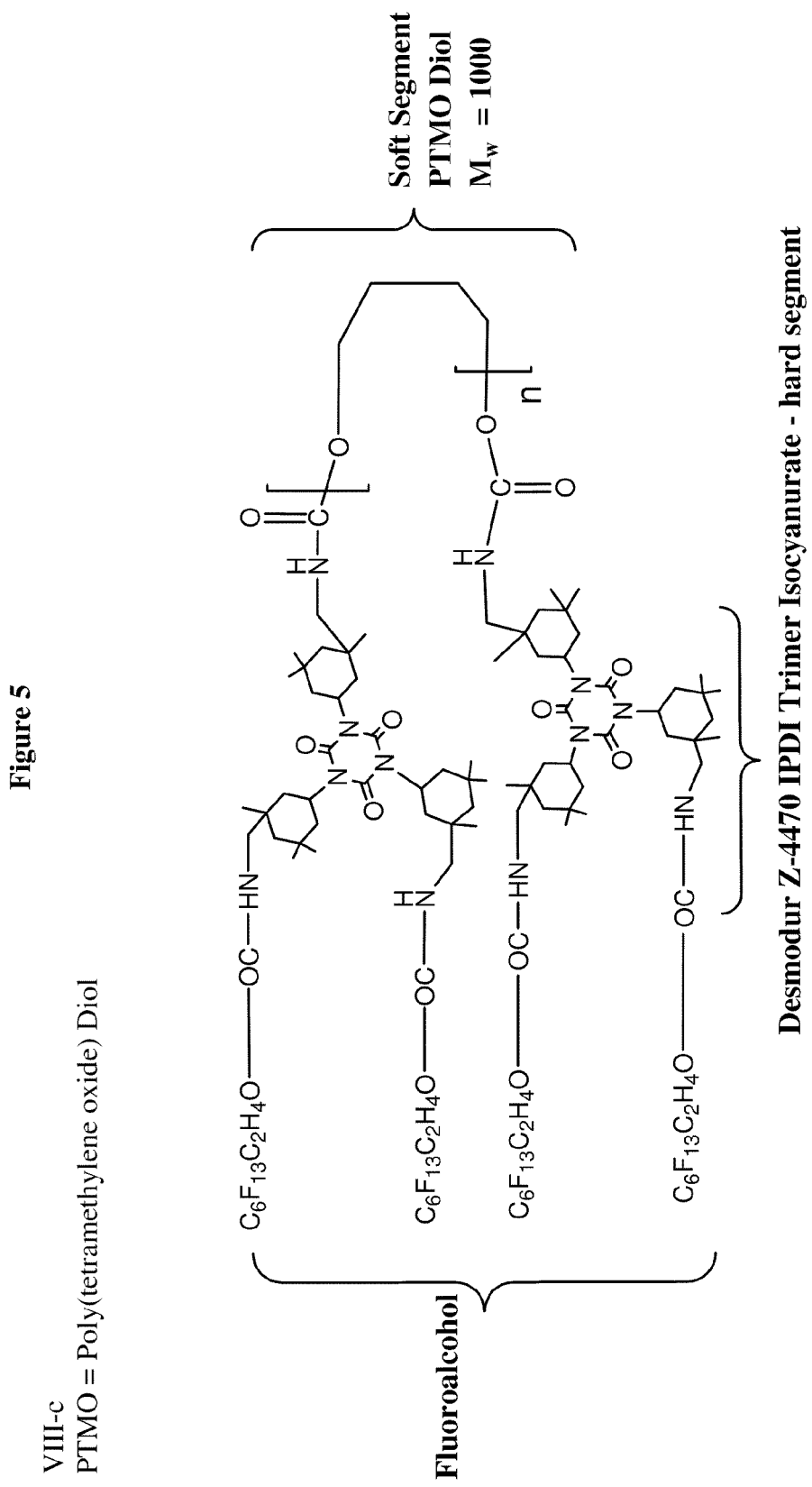
FIG. 5 is an illustration depicting surface modifying macromolecule VIII-c of the invention.
Figure 6:
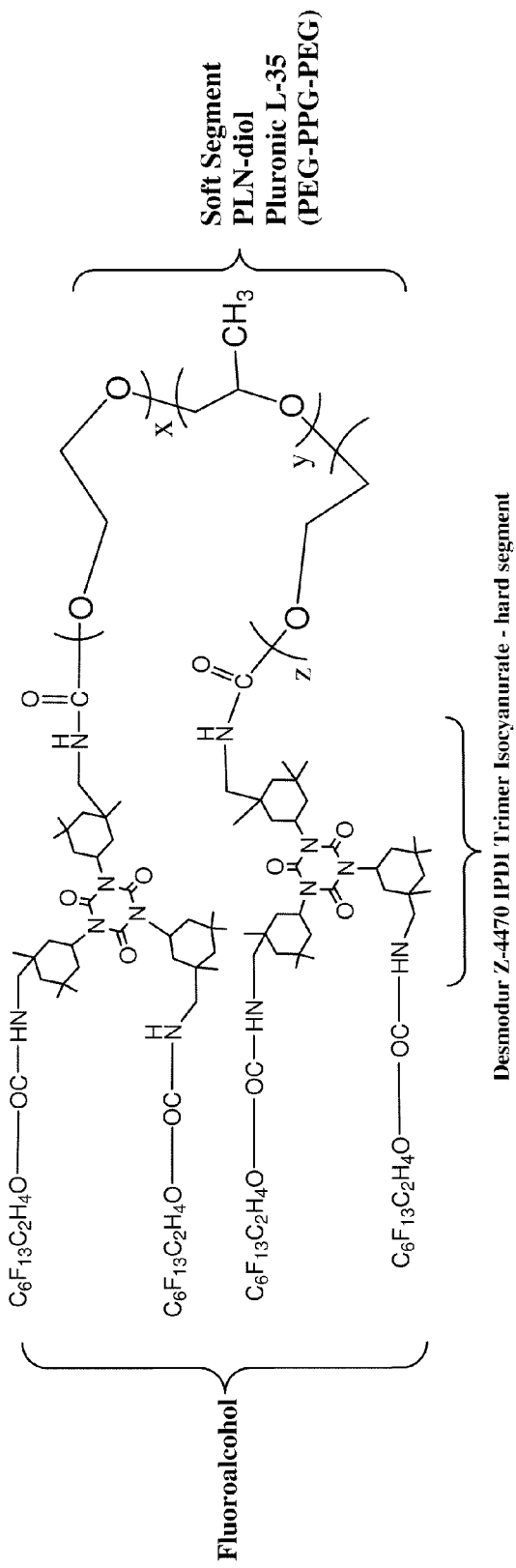
FIG. 6 is an illustration depicting surface modifying macromolecule VIII-d of the invention.
Figure 7:
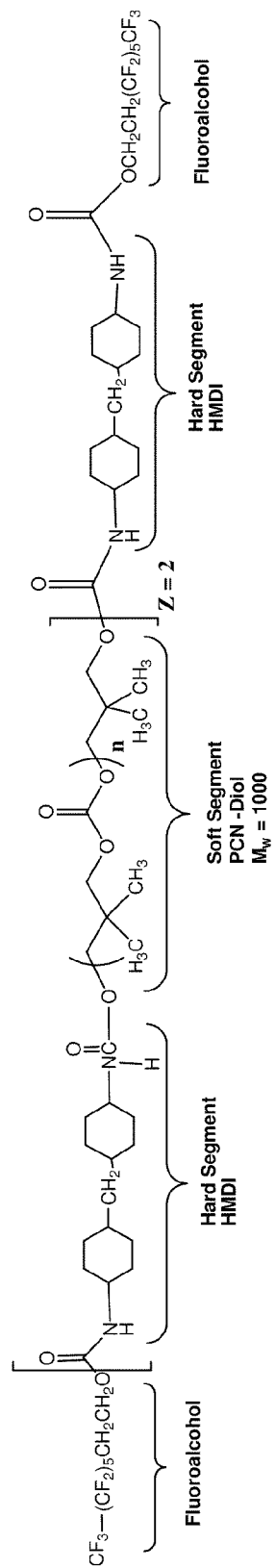
FIG. 7 is an illustration depicting surface modifying macromolecule IX-a of the invention.
Figure 8:
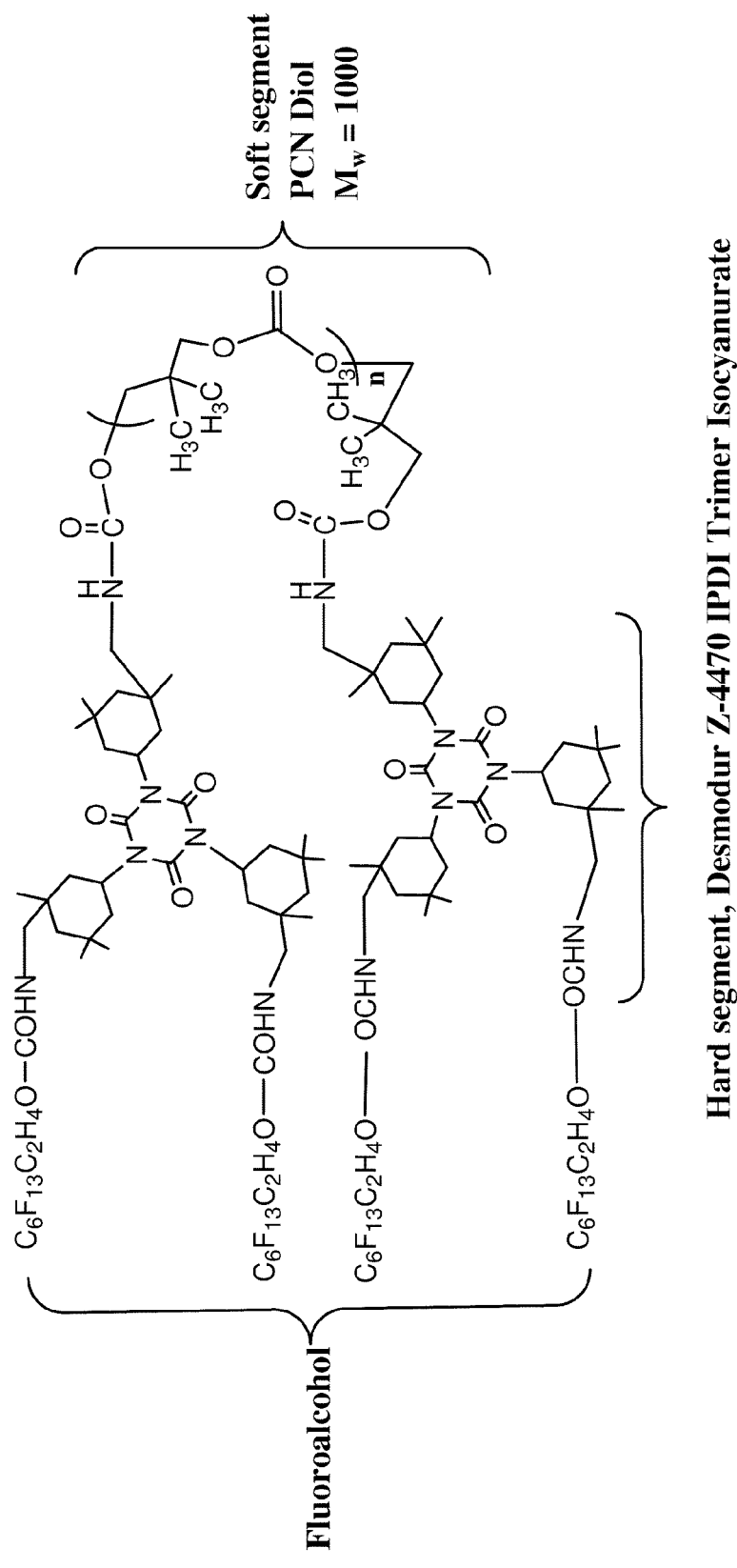
FIG. 8 is an illustration depicting surface modifying macromolecule X-a of the invention.
Figure 9:
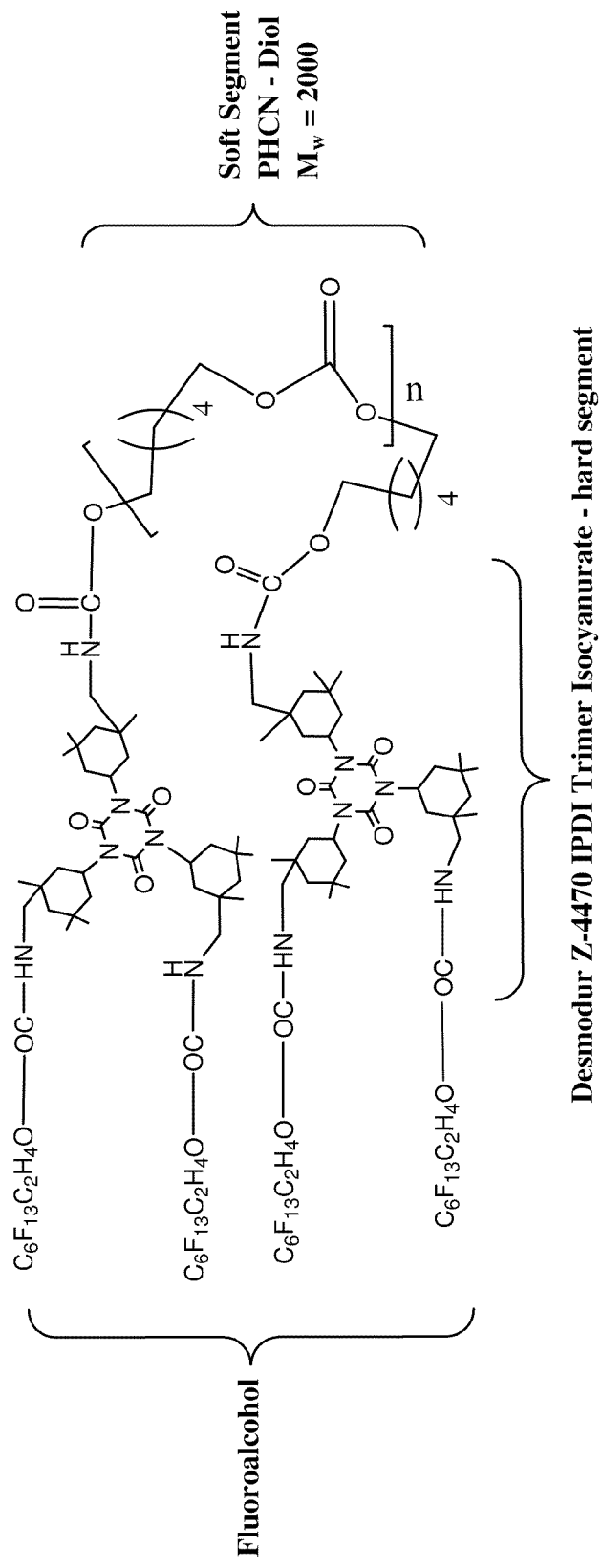
FIG. 9 is an illustration depicting surface modifying macromolecule X-b of the invention.
Figure 10:
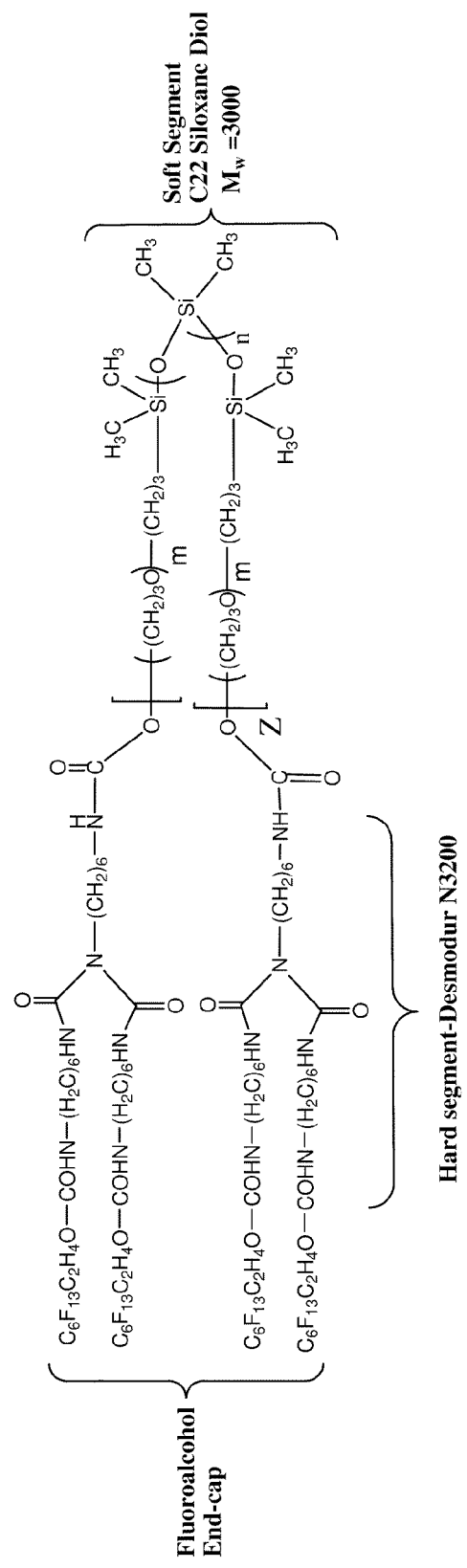
FIG. 10 is an illustration depicting surface modifying macromolecule XI-a of the invention.
Figure 11:
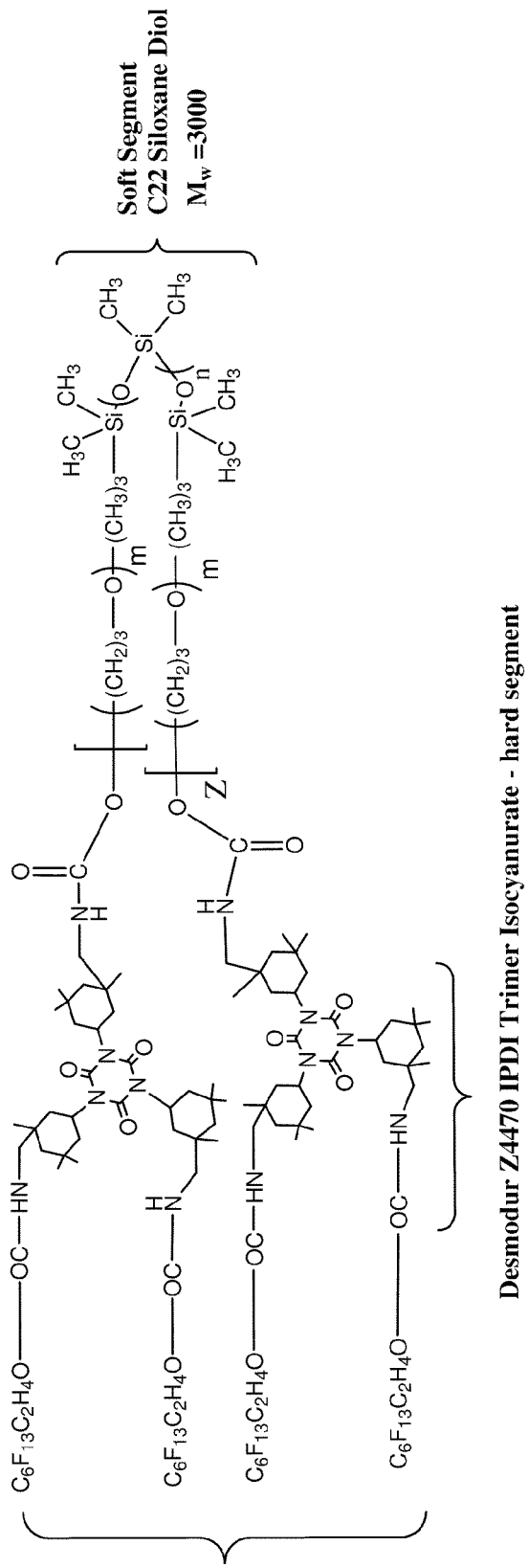
FIG. 11 is an illustration depicting surface modifying macromolecule XI-b of the invention.
Figure 12:
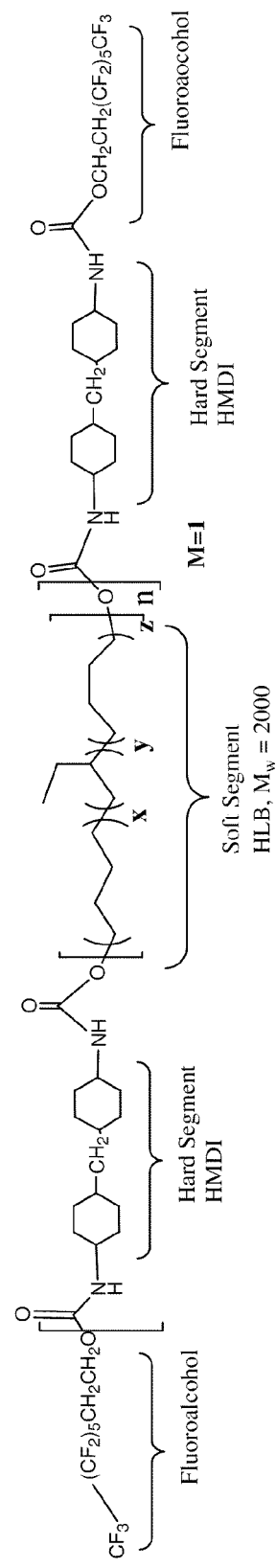
FIG. 12 is an illustration depicting surface modifying macromolecule XII-a of the invention.
Figure 13:
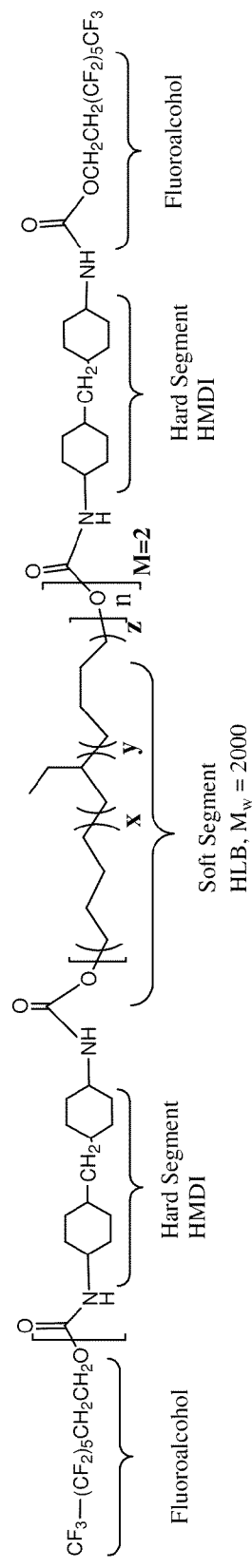
FIG. 13 is an illustration depicting surface modifying macromolecule XII-b of the invention.
Figure 14:
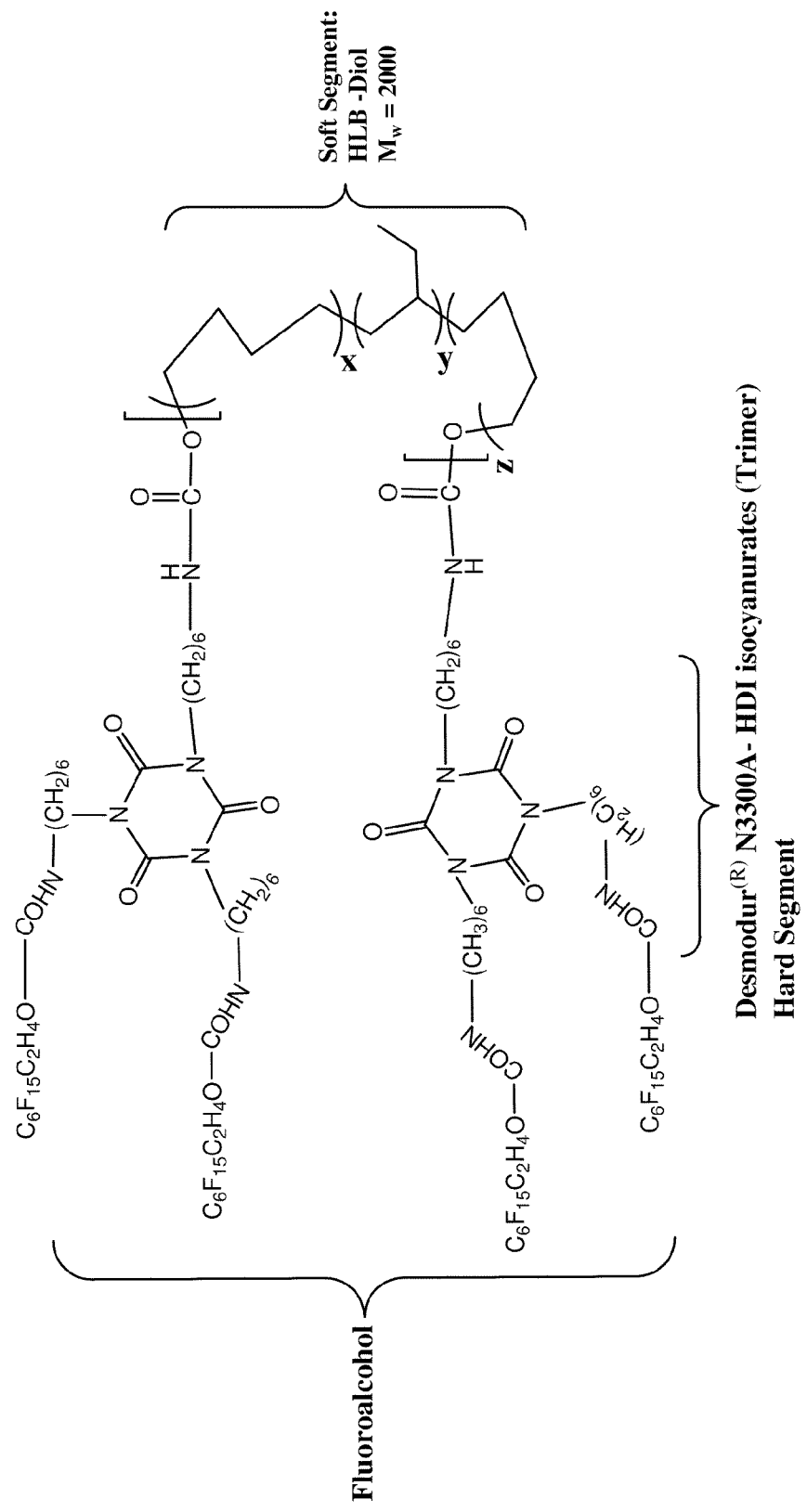
FIG. 14 is an illustration depicting surface modifying macromolecule XIII-a of the invention.
Figure 15:
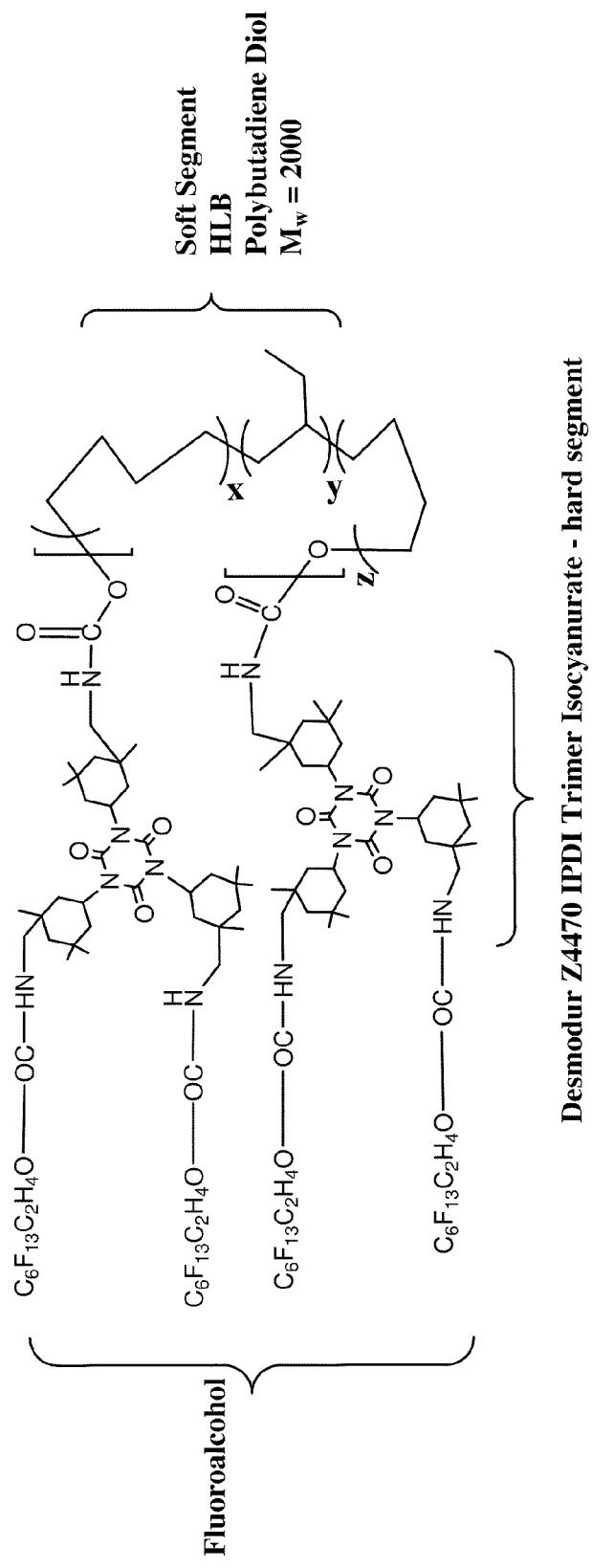
FIG. 15 is an illustration depicting surface modifying macromolecule XIII-b of the invention.
Figure 16:
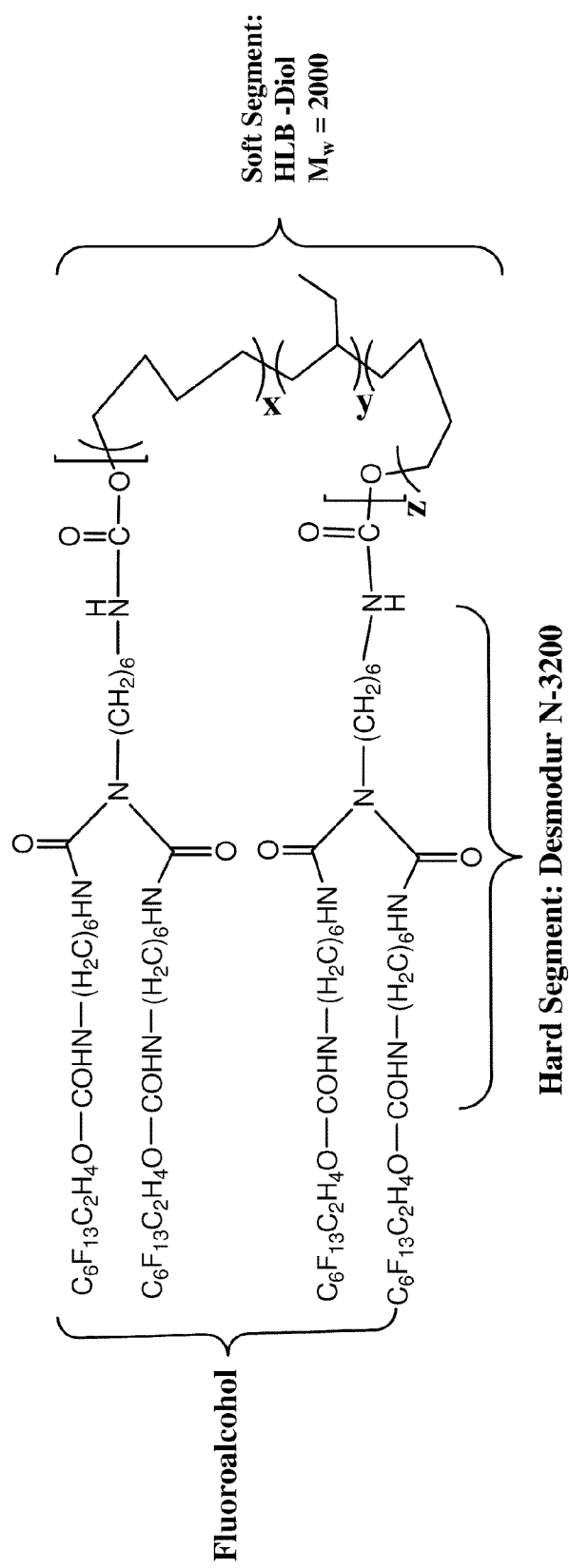
FIG. 16 is an illustration depicting surface modifying macromolecule XIII-c of the invention.
Figure 17:
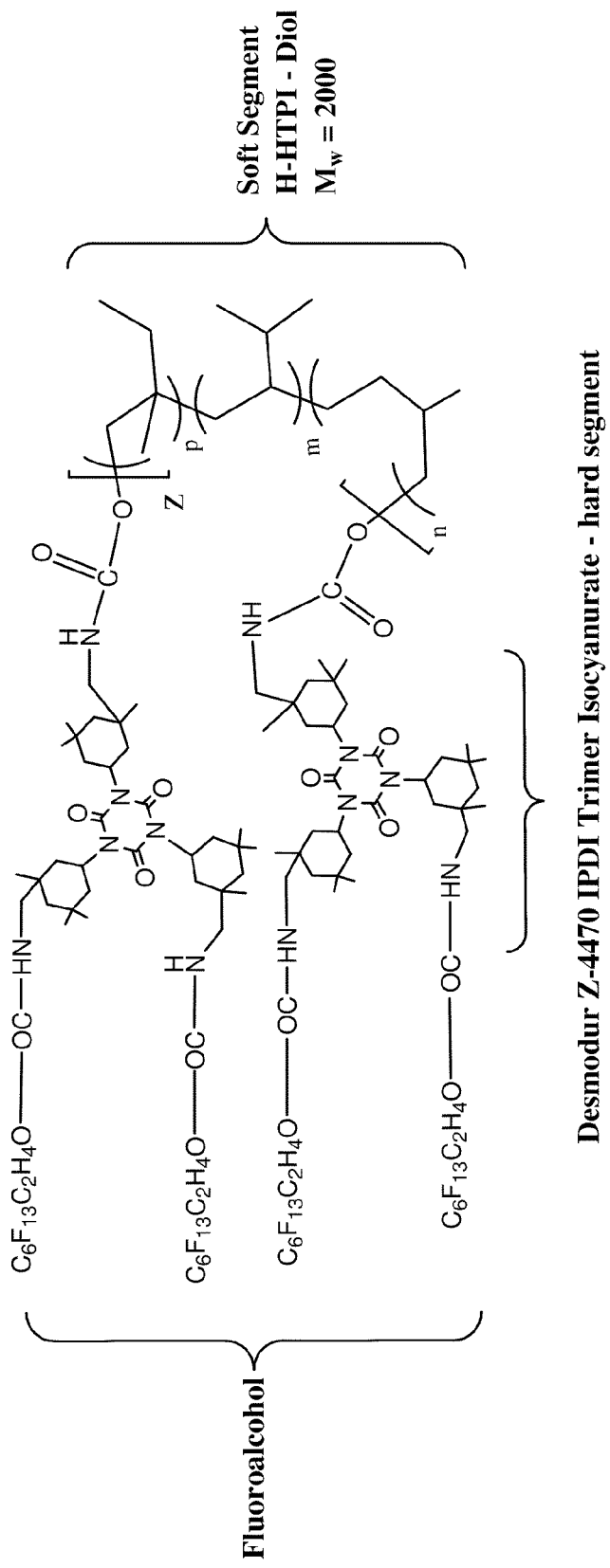
FIG. 17 is an illustration depicting surface modifying macromolecule XIII-d of the invention.
Figure 18:
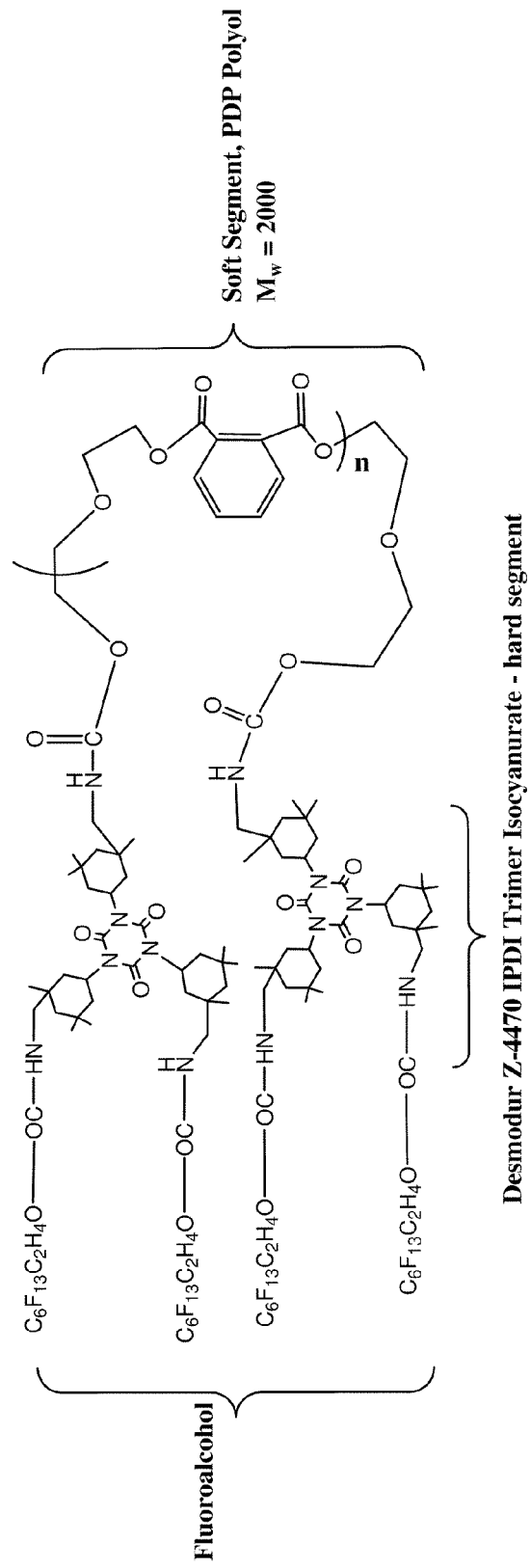
FIG. 18 is an illustration depicting surface modifying macromolecule XIV-a of the invention.
Figure 19:
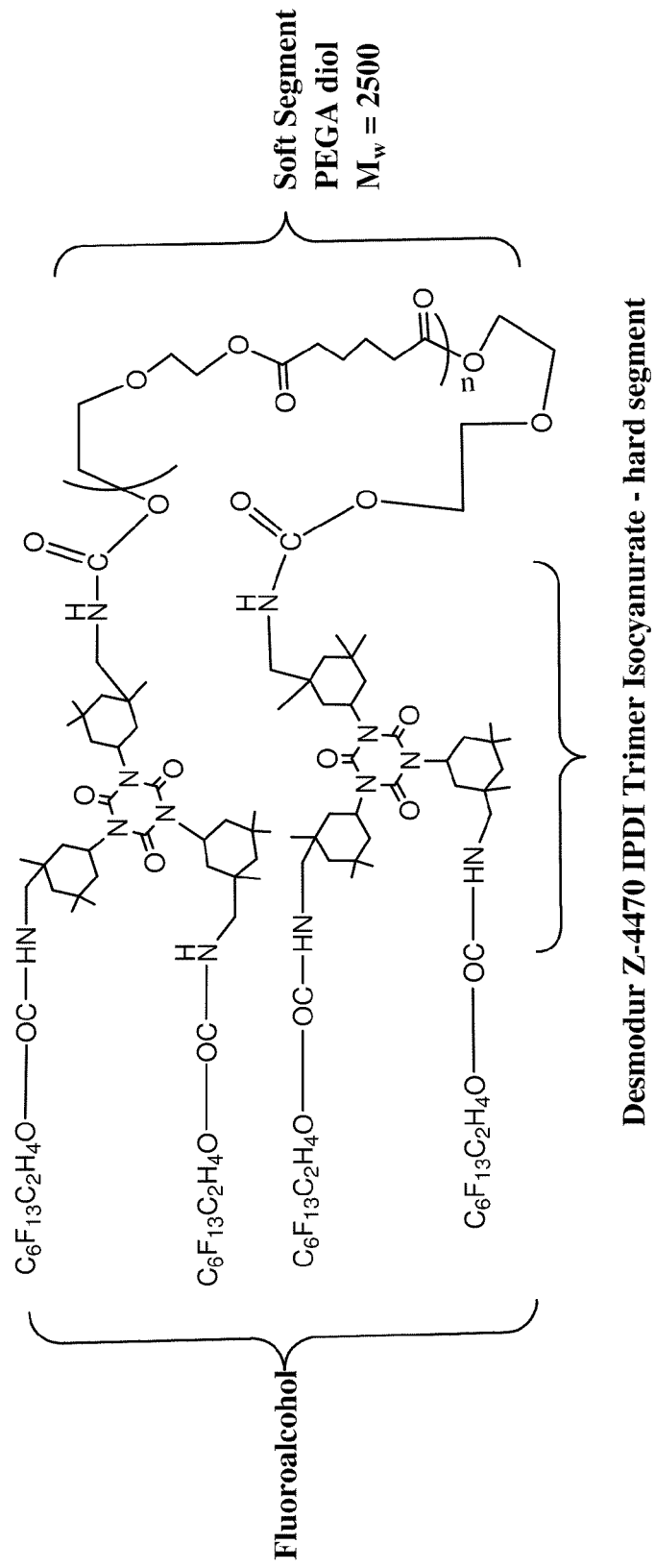
FIG. 19 is an illustration depicting surface modifying macromolecule XIV-b of the invention.

The methods and compositions of the invention feature antithrombogenic, extracorporeal blood circuits and components thereof (hollow fiber membranes, potting materials, and blood tubing, etc.) including a synthetic base polymer admixed with from 0.005% to 10% (w/w) surface modifying macromolecule. The extracorporeal blood circuit components of the invention can be used in therapies such as hemodialysis, hemofiltration, hemoconcentration, hemodiafiltration, and oxygenation, for the treatment of patients with renal failure, fluid overload, toxemic conditions, cardiac failure, or cardiac distress. They can also be used for protein separation, plasma filtration, and blood separation.

The selection of the combination of a particular surface modifying macromolecule (SMM) and a particular base polymer can be determined by the methods and protocols described herein. First, the type and amount of SMM to be added to base polymer is determined in part by whether the admixture forms a single stable phase, where the SMM is soluble in the base polymer (e.g., separation of the admixture to form two or more distinct phases would indicate an unstable solution). Then, the compatibility of the admixture can be tested by various known analytical methods. The surface of the admixture as a film or as a fiber can be analyzed by any useful spectroscopic method, such as X-ray photoelectron spectroscopy (XPS) with an elemental analysis (EA). Data from XPS could indicate the extent of modification of the surface by migrating SMMs and data from EA can indicate the extent of modification of the bulk material. Stable admixtures can then be tested to determine the thrombogenicity of the surface under various conditions.

Extracorporeal Blood Circuits

The invention features compositions and methods for reducing the activation of blood components in contact with any of the parts of an extracorporeal blood circuit (e.g., the blood tubing, the hollow fiber membrane, the potted surface, or the ends of the filter into which the blood tubing attaches) by including a surface modifying macromolecule in one or more of the parts of an extracorporeal blood circuit. The hemodialysis machine pumps the dialysate as well as the patient's blood through a dialyzer. The blood and dialysate are separated from each other by a semipermeable hollow fiber membrane, the blood passing through the extracorporeal blood circuit of a hemodialysis machine and the dialysate passing through the dialysate circuit of a hemodialysis machine. Any one or more of the blood-contacting surfaces in the extracorporeal blood circuit of a dialysis machine may be treated with a surface modifying macromolecule as described herein to produce an antithrombogenic surface. The medical separatory device of the invention can be an artificial kidney of the hollow fiber type, or a related device, such as hemofilter, blood oxygenator, or other separator of impurities from a body.

The devices include a dialysate chamber, and a pair of spaced apart drip chambers attached to each end of the dialysate chamber. Each drip chamber terminates in a port leading to blood tubing, which ultimately exit and enter a subject undergoing hemodialysis. The dialysate chamber is provided with conventional inlet and outlet dialysate ports and surrounds a bundle of axially extending hollow semipermeable fibers.

The fiber bundle contains thousands (e.g., 3,000 to 30,000) individual fibers which may formed from cellulose (e.g., made by deacetylating cellulose acetate as taught in U.S. Pat. No. 3,546,209), cellulose acetate, cellulose ester, polyesters, polyamides, polysulfone, or any other hollow fiber membrane known in the art. Typically, the fibers are fine and of capillary size which typically ranges from about 150 to about 300 microns internal diameter with a wall thickness in the range of about 20 to about 50 microns.

Referring to FIG. 1, a typical extracorporeal blood circuit 100 includes tubing through which the blood flows and components for filtering and performing dialysis on the blood.

Blood flows from a patient 105 through arterial tubing 110. Blood drips into a drip chamber 115 where a connecting tube from the drip chamber 115 attaches to a sensor 125 on a hemodialysis machine that determines the pressure of the blood on the arterial side of the extracorporeal blood circuit. A pump 120 forces the blood to continue along the path through the extracorporeal blood circuit. A dialyzer 130 separates waste products from the blood.

After passing through the dialyzer 130, the blood flows through venous tubing 140 into a second drip chamber 150. The drip chamber 150 can function as an air trap. Free gases in the blood may be able to escape into the drip chamber 150 before the blood continues to the patient. A sensor 170 is in communication with air in the drip chamber through tube 165. The sensor 170 can determine the pressure on the venous side of the extracorporeal blood circuit.

Heparin 160 can be added to the blood in the drip chamber 115. When blood is exposed to oxygen, the blood begins to clot. The drip chamber 150 may include a filter for preventing any clots from exiting the drip chamber 150 and entering the patient 105. The blood continues from the drip chamber through venous tubing 180 and through a bubble detector 175 before returning to the patient 105.

Any of the blood contacting components of the extracorporeal blood circuit can be modified with a surface modifying macromolecule as described herein to produce an antithrombogenic surface. The extracorporeal blood circuit can be useful for hemodialysis, as explained above, and can also be applied for other therapies involving hemoconcentration, oxygenation, protein separation, plasma filtration, and blood separation.

Surface Modifying Macromolecule

Illustrations of VII-a to XI-b are shown in FIGS. 2-19. For all of the SMMs, the number of soft segments can be any integer or non-integer to provide the approximate theoretical molecule weight of the soft segment. For compounds of formulas (XII) and (XIII), the number of hydrogenated alkyl moieties can be any integer or non-integer to provide the approximate theoretical molecule weight of the soft segment. Examples of XII-a, XII-b, XIII-a, XIII-b, and XIII-c include SMM's, where x=0.225, y=0.65, and z=0.125. For compounds of formula (XI), the number of first block segments and second block segments can be any integer or non-integer to provide the approximate theoretical molecule weight of the soft segment. Examples of XI-a and XI-b include SMM's, where m=12 to 16 and n=12 to 18.

Table 1 shows the SMM distribution of hard segments, soft segments, and fluorinated end-groups (F end groups). Table 1 also shows the ratio of hard segment to soft segment, which range from 0.16 to 1.49.

TABLE 1

| SMM's | MW Theo | % Soft Seg (Diol) | % Hard Seg (Isocyanate) | % F End Groups | Ratio: Hard/Soft segment |
|---|---|---|---|---|---|
| VII-a | 2016 | 47.21 | 16.68 | 36.11 | 0.35 |
| VIII-a | 3814 | 25.78 | 30.59 | 43.63 | 1.19 |
| VIII-b | 3545 | 27.73 | 31.18 | 41.09 | 1.12 |
| VIII-c | 3870 | 25.64 | 37.01 | 37.35 | 1.44 |
| VIII-d | 4800 | 39.59 | 30.07 | 30.34 | 0.76 |
| IX-a | 3515 | 56.89 | 22.39 | 20.72 | 0.39 |
| X-a | 4075 | 23.74 | 35.42 | 40.84 | 1.49 |
| X-b | 4861 | 40.35 | 29.69 | 29.96 | 0.74 |
| XI-a | 5562 | 53.94 | 19.87 | 26.19 | 0.37 |
| XI-b | 5900 | 50.85 | 24.46 | 24.69 | 0.48 |
| XII-a | 3785 | 64.60 | 13.90 | 22.00 | 0.22 |
| XII-b | 6372 | 76.20 | 12.40 | 11.40 | 0.16 |
| XIII-a | 5259 | 46.18 | 22.18 | 31.64 | 0.48 |
| XIII-b | 5536 | 43.87 | 26.07 | 30.06 | 0.59 |
| XIII-c | 5198 | 46.72 | 21.26 | 32.01 | 0.46 |
| XIII-d | 5227 | 40.55 | 27.61 | 25.38 | 0.68 |
| XIV-a | 5097 | 38.76 | 28.59 | 32.65 | 0.74 |
| XIV-b | 5450 | 46.79 | 26.48 | 26.72 | 0.57 |

Hollow Fiber Membranes

Hydrophobic polymers have been a popular choice as polymeric materials in hollow fiber spinning e.g. polysulfones, aromatic polyimides, and amides. Any base polymers described herein can be used as a hydrophobic polymer for hollow fiber spinning. For hemodialysis, hollow fiber membranes are often made from natural cellulose, cellulose derivatives (e.g. cellulose di- or tri-acetate), or synthetic polymers (e.g., polysulfones, polyacrylonitrile, or polyamides, among others), which are selected for their biocompatibility. However, none of these materials have proven to provide the desired antithrombogenicity that is needed to reduce the reliance upon anticoagulants.

In particular, polysulfones (PS) are synthetic hydrophobic polymers that are widely used in hollow fiber membranes due to their excellent fiber spinning properties and biocompatibility. However, pure hydrophobic PS cannot be used directly for some applications, e.g., dialysis membranes, as this will decrease the wetting characteristics of the membrane in an aqueous environment and affect the wetting properties essential for the clearance of toxins. To address this problem, polyvinylpyrrolidone (PVP) is typically added to the PS as a pore forming hydrophilic polymer, most of which dissolves and is lost during the hollow fiber spinning process and hydrophilically modify the PS to make it suitable as a semipermeable membrane. Although some of the PVP remains in the fiber this is not sufficient as clotting still occurs during dialysis requiring heparin anticoagulants or saline flushes of the dialyzer to clear the blockage.

The methods and compositions of the invention address these issues by including a surface modifying macromolecule in the hollow fiber membrane. The surface modifying macromolecule migrates to the surface of the hollow fiber membrane (both inner lumen and outer surface during the spinning process) to occupy the top 10 microns of the hollow fiber.

Manufacture of Hollow Fiber Membranes

A porous hollow fiber membrane adapted for use in the methods of the invention, e.g., kidney dialysis, should be capable of removing low molecular weight uremic substances while retaining useful substances such as albumin. Such porous hollow fiber membranes are produced using processes adapted to accurately control the pore diameter in the porous hollow fiber membrane. The pore diameter of the hollow fiber membrane can depend upon the composition of the spinning solution, composition of the core solution, draft ratio, liquid composition for membrane coagulation, temperature, humidity, among other factors. The composition of the core solution is an important factor as the combination and the mixing ratio of the solvent and the nonsolvent in relation to the membrane-constituting polymer determine the coagulation rate, and hence, the morphology of the interior surface of the hollow fiber membrane.

Various processes are known in the art for the production of hollow fiber membranes (see, for example, U.S. Pat. Nos. 6,001,288; 5,232,601; 4,906,375; and 4,874,522, each of which is incorporated herein by reference) including (i) processes wherein a tube-in-tube type orifice is used and the spinning solution is extruded from the outer tube (i.e., from the annular space defined between the inner and outer tubes) and the core solution is ejected from the inner tube; (ii) by extruding the spinning solution into air, allowing the filament to fall down by gravity, passing the filament through a coagulant bath for coagulation, and washing and drying the filament (dry-wet spinning); (iii) by using a bath including an upper layer of a non-coagulating solution and a lower layer of a coagulating solution, and extruding the spinning solution directly into the non-coagulating solution and passing the filament through the coagulating solution; (iv) by using a bath including an upper layer of a coagulating solution and a lower layer of a non-coagulating solution, and extruding the spinning solution directly into the non-coagulating solution and passing the filament through the coagulating solution; (v) by extruding the spinning solution directly into a non-coagulating solution and passing the filament along the boundary between the coagulating solution and the non-coagulating solution; and (vi) by extruding the spinning solution from the orifice surrounding a non-coagulating solution and passing the filament through a coagulating solution.

In such processes, pore diameter of the hollow fiber membrane is controlled by adjusting the rate and the extent of the coagulation of the extruded spinning solution through the use of a coagulation solution which promotes the coagulation of the spinning solution (a non solvent for the spinning solution) and a non-coagulation solution which inhibits the coagulation of the spinning solution (a solvent for the spinning solution) either separately or in a mixture.

For use in the compositions and methods of the invention, a typical spinning solution will include a base polymer (e.g., a polysulfone), a hydrophilic pore forming agent (e.g., polyvinylpyrrolidone, ethylene glycol, alcohols, polypropylene glycol, or polyethylene glycol), a solvent for the polymer (i.e., dimethylformamide, dimethylsulfoxide, dimethylacetamide, N-methylpyrrolidone, or mixtures thereof), and a surface modifying macromolecule.

The hollow fiber membranes of the invention can be produced, for example, by extruding the spinning solution from a tube-in-tube type orifice of the spinner in a coagulation solution to form the hollow fiber membrane. The polymer-containing spinning solution is extruded from the outer tube (i.e., annular space defined between the inner and outer tubes) to form a cylindrical filament having an inner bore and the core solution for coagulation of the spinning solution is extruded from the inner tube of the orifice into the inner bore of the filament. In this process, the filament may be directly extruded into the coagulation solution, or extruded into air and then drawn to the coagulation solution. As noted above, the spinning solution is supplemented with a hydrophilic pore forming agent and a surface modifying macromolecule and the resulting hollow fiber membrane contains the surface modifying macromolecule on its surface.

The viscosity of the spinning solution can be modified as needed. For example, by adding a thickener (e.g., polyvinylpyrrolidone (PVP), polyethylene glycol (PEG), or polypropylene glycol) to increase viscosity, or by adding an aprotic low boiling solvent (i.e., tetrahydrofuran, diethylether, methylethyl ketone, acetone, or mixtures thereof) to the spinning solution to reduce viscosity. An aprotic low boiling solvent may also be included to increase the solubility of the surface modifying macromolecule in the spinning solution.

The spinning solution is extruded to form the shape of a filament which is precipitated using a coagulating solution, resulting in formation of the desired porous hollow fiber. The coagulating solution may include a nonsolvent or a mixture of a nonsolvent and a solvent for the base polymer of the spinning solution. Typically the nonsolvent used for the coagulating solution is an aqueous solution.

After the porous hollow fiber is formed, it may be passed through a second rinsing bath. The porous hollow fiber may then be processed further, e.g., cutting, bundling, and drying, and made into a porous hollow fiber membrane suitable, e.g., for use in a dialyzer.

Potted Bundles of Hollow Fiber Membranes

The invention features compositions and methods for reducing the activation of blood components in contact with the potting material of a filter (e.g., as part of a blood purification device, such as a hemodialysis, hemodiafiltration, hemofiltration, hemoconcentration, or oxygenator device) by including a surface modifying macromolecule in the potting material at the time that the hollow fiber membranes are potted.

In order to filter or permeate with hollow fiber membranes, a large number of thin hollow fibers must be potted (i.e., fixed) to a header of an encasement such that their inner surfaces are each completely sealed to the inside of the encasement but their lumens are open to pass blood from a first potted end to a second potted end of a filter. Potting materials are an important integral part of blood purification filter as these are cured polymer materials (usually a polyurethane) that act as a glue to hold the hollow membrane fiber bundles (e.g., numbering up to 20,000) firmly at the ends inside the cartridge of the dialyzer, while at the same time leaving the ends of the hollow fibers open to allow for passage of blood into the fibers for filtration purposes. Holding these numerous fiber bundles inside an encasement and ensuring that each and every hollow fiber is properly aligned along the axis of the cartridge is a necessary step in a filter assembly.

The potted walls formed at either end of a blood purification filter is an area prone to turbulent blood flow under shear conditions which causes activation of the blood components and first initiate thrombus formation which can adversely affect blood flow and filter function. This problem is not ameliorated by the use of antithrombogenic hollow fiber membranes as the ends of the hollow fiber membranes are only a very small portion of a typical wall surface (e.g., ca. 18% of the wall surface), followed by hollow lumen (e.g., ca. 16% of the wall surface), and a large amount of potting material (e.g., ca. 66% of the wall surface). There is a need to address this larger area where dynamic blood flow takes place and where most of thrombus starts that may lead to occlusion of the filters. There is a need for hollow fiber membranes and blood filtration devices that have reduced thrombogenicity.

Potting materials can be thermoset polymers formed by mixing two or more components to form a cured resin (i.e., typically a polyurethane). To produce an antithrombogenic potting material of the invention a surface modifying macromolecule is added to at least one of the components of the potting material prior to mixing to form the cured resin.

The surface modifying macromolecules can be incorporated into any potting material known in the art. For example, surface modifying macromolecules can be incorporated into polyurethane potting materials formed from an isocyanate-terminated prepolymer, the reaction product of a polyol and a polyisocyanate, and cured with one or more polyfunctional crosslinking agents have been described in the art. Potting materials that can be used in the methods, compositions, and dialysis systems of the invention include those described in U.S. Pat. Nos. 3,362,921; 3,483,150; 3,362,921; 3,962,094; 2,972,349; 3,228,876; 3,228,877; 3,339,341; 3,442,088; 3,423,491; 3,503,515; 3,551,331; 3,362,921; 3,708,071; 3,722,695; 3,962,094; 4,031,012; 4,256,617; 4,284,506; and 4,332,927, each of which is incorporated herein by reference.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Illustration and Calculation of Potting Area

Figure 20A:
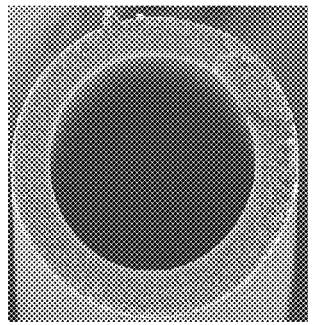
FIGS. 20A and 20B show an exemplary hollow fiber and an exemplary bundle of fibers.
Figure 20B:
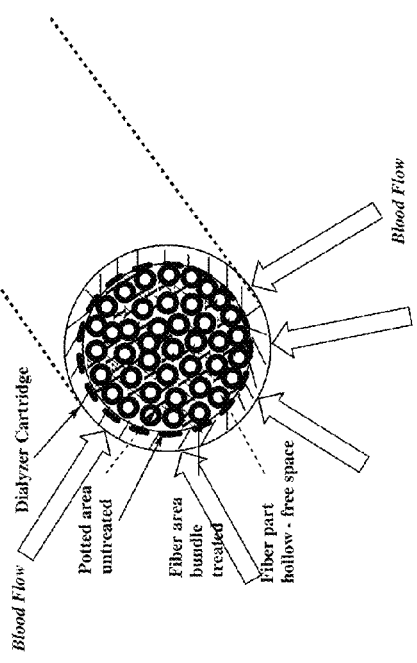

FIG. 20A is a scanning electron micrograph of a single hollow fiber. FIG. 20B is an illustration of a hollow fiber bundle. FIGS. 20A-20B highlight the ability of the fiber bundle to provide an antithrombogenic surface area when in contact with blood. Based upon the dimensions of the potted area and the fiber, it can be estimated that if only the hollow fiber membranes are modified as described herein, then only ~18% of the header area occupied by the fibers (depicted by circles with thick lines within the dialyzer cartridge) is modified with the surface modifying macromolecules (SMM) for providing the antithrombogenic effect. This leaves ~66% of the area including the potted part unmodified and prone to thrombus formation when in contact with blood during hemodialysis. Accordingly, this invention features a method of treating this ~66% of the potted part (an integral part of the fiber) also with surface modifying macromolecules to obtain a header surface that is antithrombogenic, minimizes blood activation, reduces blood coagulation, and reduces the incidence of hemofilter occlusion.

EXAMPLE 2

Surface Modifying Macromolecule in Films of PS/PVP Polymer Blends

Films were prepared to demonstrate the surface composition in the mixtures from which the hollow fiber membranes of the invention can be made. A surface modifying macromolecule (SMM, 5 wt %), polysulfone (PS, 10 wt %) and polyvinylpyrrolidone (PVP, 5 wt %) were dissolved in a mixture of dimethylacetamide and tetrahydrofuran (ca. 80 wt %). Films having a thickness of 254 μm were cast on Teflon substrates and were then dried and analyzed for surface Fluorine and Nitrogen content. The results are provided in Table 2 for the four solution cast formulation films that were analyzed, each utilizing a different surface modifying macromolecule.

TABLE 2

| SMM # | XPS in PS/PVP/SMM Films (Surface) | | EA of SMM (Bulk) | |
|---|---|---|---|---|
| | % F | % N | % F | % N |
| VIII-a | 42.77 | 4.23 | 33.2 | 5.07 |
| VIII-b | 43.82 | 4.39 | 23.29 | 6.66 |
| XI-a | 37.34 | 4.93 | 15.94 | 3.9 |
| XIII-a | 42.75 | 4.05 | 20.63 | 3.49 |

The surface fluorine content is provided by the X-ray photoelectron spectroscopy (XPS) results for the four films, while the elemental analysis (EA) of the bulk (neat) SMM is provided for comparison. The difference in XPS and EA data for percent fluorine content results from the migration of the oligofluoro groups of the surface modifying macromolecule to the surface of the film. The percent nitrogen content at the surface reflects the presence of the hydrophilic urethane portion of the surface modifying macromolecule at the surface of the film in addition to the presence of the polyvinylpyrrolidone.

EXAMPLE 3

Surface Modifying Macromolecule in Fibers of PS/PVP Polymer Blends

Fibers were also analyzed for Fluorine and Nitrogen content. The results are provided in Table 3 for the four solution spun fibers that were analyzed, each utilizing a different surface modifying macromolecule (VII-a, VIII-a, IX-a, and XI-a).

TABLE 3

| SMM Fibers | XPS (OS) | | XPS (IS) | | EA (Fibers) | |
|---|---|---|---|---|---|---|
| | % F | % N | % F | % N | % F (x) | % N |
| VII-a | 12.06 | 4.02 | 10.79 | 2.33 | 0.83 (4)[a] | 0.50 |
| VIII-a | 5.14 | 4.15 | 8.68 | 2.90 | 0.74 ((3)[b] | 0.52 |

TABLE 3-continued

| SMM | XPS (OS) | | XPS (IS) | | EA (Fibers) | |
|---|---|---|---|---|---|---|
| Fibers | % F | % N | % F | % N | % F (x) | % N |
| IX-a | 0.78 | 2.9 | 2.76 | 1.51 | 0.17 (2)[b] | <0.50 |
| XI-a | 1.35 | 3.11 | 1.71 | 1.39 | 0.27 (1.6)[c] | <0.50 |
|  | Si = 1.51% | | Si = 2.38% | | | |
| Control Polysulfone/PVP Fibers | 0.00 | 4.12 | 0.00 | 1.47 | 0 (0) | <0.5 |

[a]Target incorporation of VII-a = 6%
[b]Target incorporation of VIII-a & IX-a = 4%
[c]Target incorporation of XI-a = 3%

The X-ray photoelectron spectroscopy (XPS) data indicated that all of the SMM modified fibers have surface fluorine to various degrees both in the inner surface (IS) that actually comes in contact with blood during hemodialysis and the outer surface (OS).

Table 3 also provides the elemental analysis (EA) of the SMM's and the % F in the bulk, which indicates the amount of the additive incorporated into the fibers as compared to the targeted incorporation amount. For VII-a, the EA of the % F shows that of the 6 wt % additive incorporation only 4 wt % was actually present. This loss of ~33% can be attributed to the harsh conditions of the fiber spinning process, which involves spinning solvent mixtures that dissolves some of the SMM at the same time that it dissolves the pore forming polyvinylpyrrolidone (PVP). This is true for VIII-a, IX-a, and XI-a and is reflected in the difference between the target incorporation and the actual incorporation that is calculated from the elemental analysis. However, all the SMM's no matter their final concentration are robust enough to remain in sufficient quantities to provide significant impact on the surface properties, which can be reflected in the antithrombogenic properties evidenced in the blood loop studies in Example 5.

Table 3 shows that for the commercial control PS/PVP fibers (not modified with SMM) the XPS results show an absence of Fluorine. The nitrogen content in the commercial fiber comes from the PVP that remains after most of it is washed away during the spinning process. The amount of PVP remaining in the unmodified and SMM modified fibers will also vary.

Considering the XPS results of the inner surface of the fibers (IS) which comes in contact with the blood, Table 3 shows that for VII-a, VIII-a, IX-a, and XI-a the % F (hydrophobic groups) range from 1.71%-10.79% and the % N (hydrophilic groups) are in the range 1.39%-2.90%. As determined from the data from Table 3, the ratio of % F to % N includes from 1.23-4.63 and possible ranges for the ratio of % F to % N include from 1.20 to 10.0. As provided in Table 1, the ratio of hard segments to soft segments includes from 0.16-1.49 and possible ranges for this ratio of hard segments to soft segments include from 0.15 to 2.0.

While VII-a and XI-a performed the best in this series as shown in Example 5, VIII-a and IX-a did not have any major failures, compared to the control nor did the failures result in major occlusion of the filters. Unlike the control, filters modified with VII-a, VIII-a, IX-a, or XI-a did not show such large variation in the header pressures and γ-count (as compared to the standard error in Table 6.).

EXAMPLE 4

Surface Modifying Macromolecule in Potting Materials

Sample disks were prepared to demonstrate the surface composition in the polymer material including the potted area.

A commercially available potting compound GSP-1555 from GS polymers Inc. was used as the potting material. It is a two part system consisting of Part A (HMDI based diisocyanate) and Part B (a polyol). Four SMM's designated as VII-a, VIII-a, IX-a, and XI-a (structure depicted in FIGS. 2-5) were admixed with the GSP 1555 potting material as shown in Table 4. VII-a was used in two concentrations of 1% and 2%, respectively. All other SMM's, i.e., VIII-a, IX-a, and XI-a, were prepared in only 2% (w/w) concentration according to the following method.

To the GSP 1555 precursor polyol was added the SMM in a 40 ml plastic falcon tube with thorough mixing. The mixture was dissolved in a volume of THF. The GSP 1555 precursor diisocyanate was then added, and the reaction mixture was stirred. The resulting GSP 1555 potting compound containing SMM was allowed to cure at room temperature for 24-48 hours. The cured mixture was then dried under vacuum for 48 hours to remove any residual solvent from the samples.

TABLE 4

| | GSP 1555 2A:1B | | | | |
|---|---|---|---|---|---|
| SMM # Form | Part A (HMDI) (g) | Part B (Polyol) (g) | Conc of A:B in Sol. (%) | SMM (g) | Conc of SMM in (A:B) % |
| VII-a | 6.7 | 3.3 | 20 | 0.1 | 1 |
| VII-a | 6.7 | 3.3 | 20 | 0.2 | 2 |
| VIII-a | 6.7 | 3.3 | 20 | 0.2 | 2 |
| IX-a | 6.7 | 3.3 | 20 | 0.2 | 2 |
| XI-a | 6.7 | 3.3 | 20 | 0.2 | 2 |

The samples were cut into appropriate sizes and submitted for XPS. The XPS results are provided in Table 5. Values of the atomic % F demonstrate that all parts of the potted materials (i.e., the top surface and new surfaces generated after cutting) have been modified with the additive. That the cut portions of the potted materials have been modified with the additive is important, because production of a filter from a bundle of potted hollow fiber membranes typically includes generating a new surface as the potted portion of the bundle is cut to produce a smooth finish to expose the hollow fiber openings. Values of the atomic % F also demonstrate that migration of the SMM to a surface is a dynamic process and occurs at all surfaces, including those surfaces newly generated. For example, VII-a was incorporated at 1% (w/w) to produce a top portion which displays a surface that is 30% fluorine. After heating at 60° C. for 24 hours to increase the amount of surface modifying macromolecule near the surface of the wall, the % F content at the surface was reduced to ~13%. After cutting the sample the XPS showed that the cut surface displays a surface that is ~7% fluorine, which upon heating at 60° C. for 24 hours is increased to ~26% fluorine. Thus, the potting material surface of the invention can be heated if there is insufficient fluorine at a freshly cut surface. Similar observations were made for the other SMM's. This also demonstrates that SMM's can migrate through cured or thermoset polymers.

TABLE 5

| Samples | | % F | % N | % Si |
|---|---|---|---|---|
| Control | 1-T[1] | 3.51[5] | 4.42 | 0.49 |
| GSP1555 | 1-T60[2] | 0.36 | 4.40 | 0.88 |
| polyurethane | 1-C[3] | 0.60 | 4.68 | 1.03 |
| #1 | 1-C60[4] | — | — | — |
| VII-a | 2-T | 30.23 | 3.45 | 0.31 |
| 1% | 2-T60 | 13.24 | 3.18 | 0.37 |
| #2 | 2-C | 6.77 | 3.96 | 0.41 |
|  | 2-C60 | 26.10 | 3.32 | 0.24 |
| VII-a | 3-T | 18.00 | 3.80 | 0.09 |
| 2% | 3-T60 | 27.00 | 3.31 | 0.19 |
| #3 | 3-C | 12.60 | 3.16 | 0.16 |
|  | 3-C60 | 41.93 | 3.62 | 0.01 |
|  | 4-T | 28.90 | 6.31 | 1.79 |
| VIII-a | 4-T60 | 31.40 | 6.66 | 0.78 |
| 2% | 4-C | 23.88 | 5.54 | 1.50 |
| #4 | 4-C60 | 22.75 | 5.93 | 1.04 |
|  | 5-T | 3.00 | 3.29 | 0.26 |
| IX-a | 5-T60 | 9.10 | 2.69 | 0.75 |
| 2% | 5-C | 7.47 | 3.93 | 1.42 |
| #5 | 5-C60 | 11.08 | 2.99 | 0.47 |
|  | 6-T | 36.71 | 5.72 | 0.00 |
| XI-a | 6-T60 | 42.31 | 5.25 | 0.02 |
| 2% | 6-C | 26.19 | 6.07 | 0.17 |
| #6 | 6-C60 | 33.35 | 5.81 | 0.01 |

[1] T = Top portion of sample at ambient temperature.
[2] T60 = Top portion of sample at 60° C., 24 hours.
[3] C = Cut portion of sample at ambient temperature.
[4] C60 = Cut portion of sample at 60° C., 24 hours.
[5] Control should be devoid of fluorine. Here a 3% F content indicates contamination.

EXAMPLE 5

In Vitro Assessment of Hemofilter Thrombosis

Thrombotic surface activity of hemofilters was assessed using commercially available hemofilters in response to heparinized bovine blood. Hemofilters were surface modified with VII-a, VIII-a, IX-a, or XI-a and compared with control (hemofilter that was not surface modified).

Materials

Commercially available hemofilters containing PS/PVP were used as the control. Four surface modifying macromolecules (SMM's) of VII-a, VIII-a, IX-a, and XI-a (as shown in the Figures) having various chemical constituents were used to modify the commercial hemofilters, which were used as the test samples together with the control filters. Commercial filters modified with VII-a had 4% additive incorporation. Commercial filters modified with VIII-a had 3% additive incorporation. Commercial filters modified with IX-a had 2% additive incorporation. Commercial filters modified with XI-a had 1.6% additive incorporation. A total of 30 filters were analyzed in the study. Heparinized bovine blood (2 units/ml) was used for each experiment, where the study included 3 or 6 cows. QC release tests were performed on the modified filters for dialyzer function and assessment of fiber dimensions. These were compared to the control filters.

Methods

An in vitro assessment of hemofilter thrombosis was made using a standard blood loop system and protocol (see Sukavaneshvar et al., Annals of Biomedical Engineering 28:182-193 (2000), Sukavaneshvar et al., Thrombosis and Haemostasis 83:322-326 (2000), and Sukavaneshvar et al., ASAIO Journal 44:M388-M392 (1998)).

Briefly, the following protocol was used. The blood loop system included a reservoir, a pump, a hemofilter, and tubing to form a closed flow loop. The loop system was primed with phosphate buffered saline (PBS) at 37° C. and circulated for 1 hour before starting an experiment, and pressure was measured at the pressure port between the pump and the hemofilter.

Approximately 10 liters of fresh bovine blood was obtained from a single animal for each experiment and heparinized (typical concentration=2 U/ml). The experiments were conducted within 8 h of blood collection. Radiolabeled, autologous platelets (with $^{111}$Indium) were added to the blood prior to the commencement of the study. The PBS in the reservoir was replaced with blood, and pressure was monitored. Blood circulation in the loop system was typically maintained for 1-2 hours (unless terminated due to significant pressure build-up, as monitored by a pressure gauge). At the end of the experiment, hemofilters were photographed, and γ-count was measured at the inlet, outlet, and middle of the hemofilter using a γ-probe.

Figure 21:
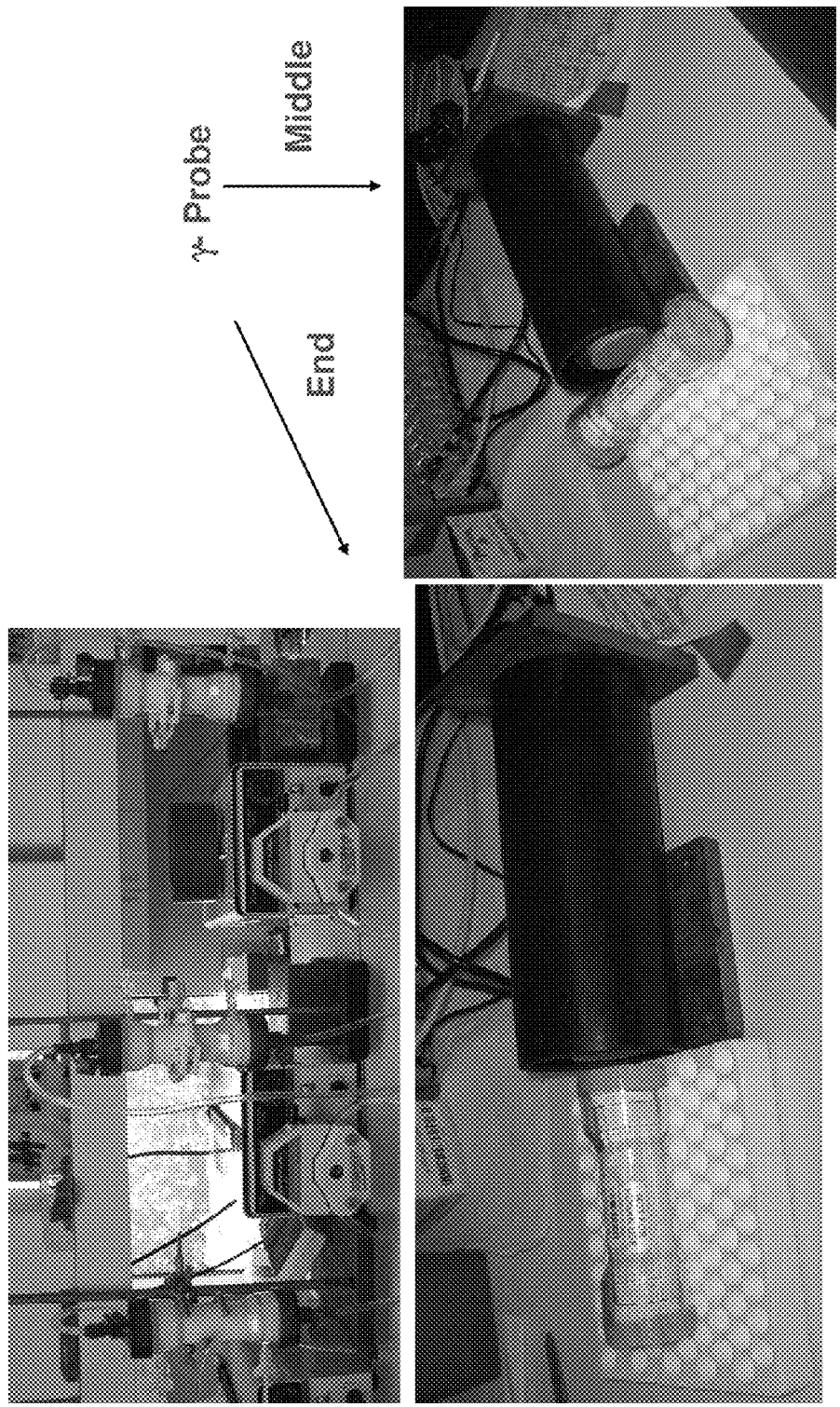
FIG. 21 is a photograph of an exemplary configuration for in vitro blood loop analysis and gamma probe reading.
Figure 22:
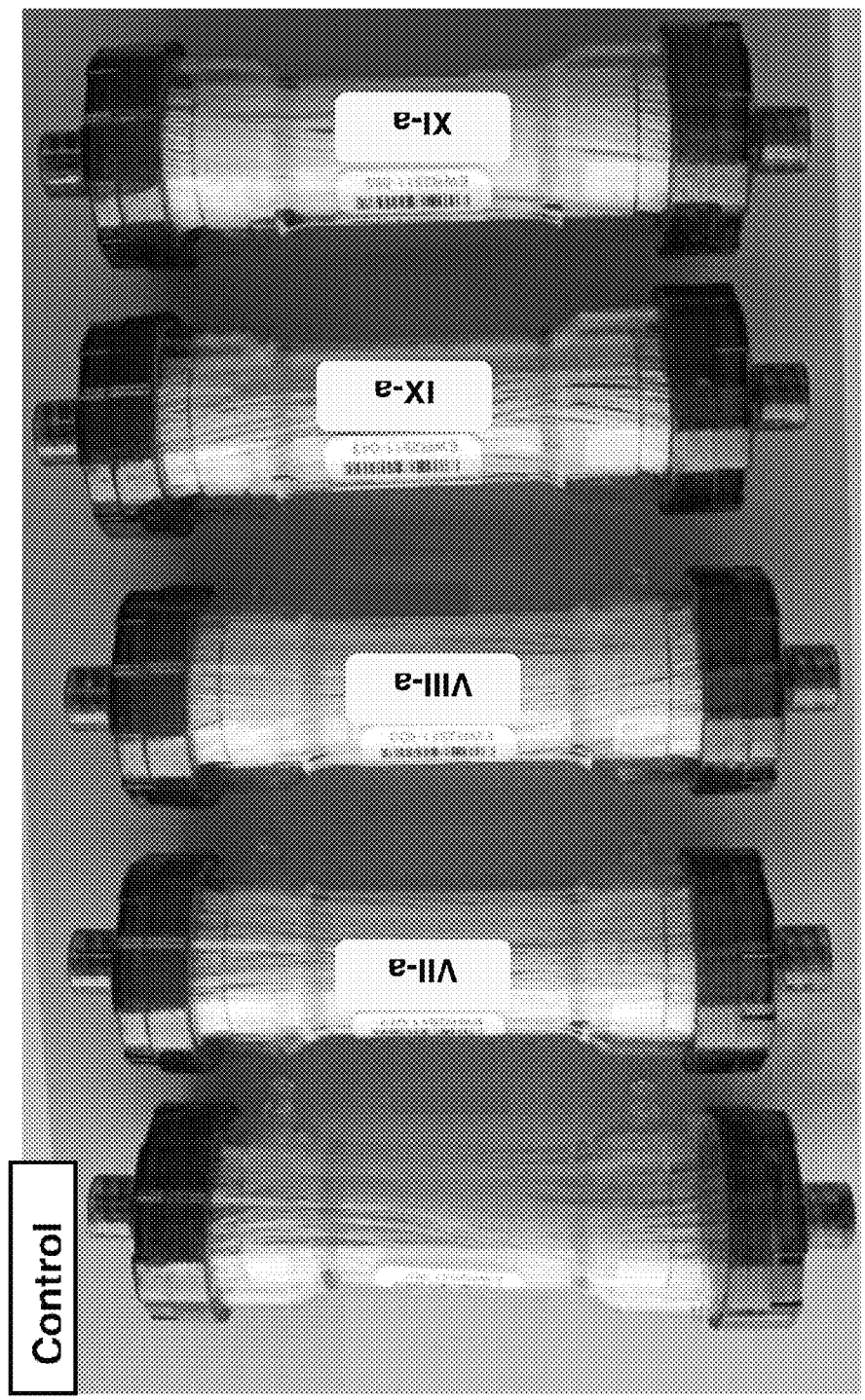
FIG. 22 is a photograph of hemofilters after a blood loop procedure.

FIG. 21 shows the experimental set-up for the in vitro blood loop analysis and the configuration of the hemofilters for the study. The figure also shows the arrangement of the γ-probe reading for the hemofilters, where measurements were determined end-on and in the middle of the hemofilters. The γ-probe readings for the radiolabeled platelets were determined after the filters were exposed to the blood flow and rinsed with PBS solution to remove any residual blood. FIG. 22 shows an arrangement of the hemofilters after the blood loop procedure, just before the header caps (top and bottom caps) are unscrewed to visually examine for thrombus.

Results & Discussion

Table 6 shows the results of the in vitro study of hemodialysis filters thrombus for control (C1) versus VII-a, VIII-a, IX-a, and XI-a. Table 6 also shows the header pressure change (ΔP) at the inlet (top cap in FIG. 22) and the γ-probe readings of the radiolabeled activated platelets at the inlet (top cap in FIG. 22), middle, and outlet (bottom cap in FIG. 22) regions of the hemofilters after blood contacting for Experiments 1-6. In Experiment 1, the first filter to fail after 25 minutes was IX-a, where the header pressure was 180 mm Hg. This is called the failure or occlusion time. Failure here means when the header pressure reached ≥175 mm Hg over the base pressure. At this point, the γ-count of the activated platelets was 3582, while it was 3250 in the middle and 2223 at the outlet. VII-a performed the best in this experiment not only amongst the SMM's but also compared to the control with the lowest header pressure of 20 vs. 53 mm Hg (control). The γ-count at this point was 2631. However, the γ-count in the middle was higher (at 4534) and lower in the outlet (at 2454). The higher γ-count in the middle may be indicative of loosely bound micro-thrombi that slips through into the fiber (due to the additive nature of the SMM), which does not allow the thrombi to accumulate. The higher concentration of activated platelets in the middle of the filters is generally true for most of the SMM modified filters, as is evident in Experiments 1, 2, 3, 5, and 6. In this experiment (Experiment 1), XI-a modified filters also performed well with a header pressure of 35 mm Hg, as compared to the control.

TABLE 6

| Expt | | Header pr | γ-probe read, (cpm) | | | Total Radiation |
|---|---|---|---|---|---|---|
| Flow = 200 ml/min | Filters # | Δ Pr Inlet (red) | R Inlet | M Middle | B Outlet | cpm |
| Expt 1 | C1 | 53 | 2231 | 2165 | 1410 | 4396 |
| Occlusion | VII-a | 20 | 2631 | 4534 | 2454 | 7165 |
| time | VIII-a | 53 | 2667 | 3683 | 2049 | 6350 |
| t = 25 mins | IX-a[a] | 180 | 3582 | 3250 | 2223 | 6832 |
| | XI-a | 35 | 2701 | 4631 | 2527 | 7332 |
| Expt 2 | C1 | 86 | 1905 | 1536 | 1078 | 3441 |
| Occlusion | VII-a | 158 | 3293 | 3557 | 2085 | 6850 |
| time | VIII-a[a] | 185 | 2623 | 2806 | 1512 | 5429 |
| t = 57 mins | IX-a | 155 | 2413 | 2510 | 1821 | 4923 |
| | XI-a | 176 | 2791 | 2942 | 1770 | 5733 |
| 3 | C1 | 154 | 20339 | 4624 | 2619 | 24963 |
| Occlusion | VII-a | 21 | 6554 | 4608 | 2662 | 11162 |
| time | VIII-a[a] | 227 | 19816 | 5799 | 2692 | 25615 |
| t = 30 mins | IX-a | 217 | 19982 | 6876 | 3930 | 26858 |
| | XI-a | 36 | 7660 | 2962 | 1867 | 10622 |
| 4 | C1[a] | 926 | 17982 | 4342 | 5707 | 22324 |
| Occlusion | VII-a | 9 | 1915 | 2547 | 1479 | 4462 |
| time | VIII-a | 12 | 1941 | 2106 | 1311 | 4047 |
| t = 8 mins | IX-a | 133 | 6433 | 3893 | 2554 | 10326 |
| | XI-a | 51 | 1404 | 1993 | 1196 | 3397 |
| 5 | C1[a] | 362 | 4836 | 2747 | 1984 | 7583 |
| Occlusion | VII-a | −3 | 2255 | 3442 | 2301 | 5697 |
| time | VIII-a | 8 | 5577 | 8065 | 4835 | 13642 |
| t = 10 mins | IX-a | 8 | 905 | 917 | 913 | 1822 |
| | XI-a | −5 | 1012 | 1098 | 435 | 2110 |
| 6 | C1 | 33 | 2465 | 1717 | 1082 | 4182 |
| Occlusion | VII-a | 41 | 5091 | 5762 | 2967 | 10853 |
| time | VIII-a[a] | 222 | 5019 | 3664 | 1850 | 8683 |
| t = 40 mins | IX-a | 35 | 2280 | 2348 | 1519 | 4628 |
| | XI-a | 63 | 3644 | 3186 | 1673 | 6830 |

[a]Filters that failed in each experiment

In Experiment 2, VIII-a failed within 57 minutes with a header pressure of 185 mm Hg. In this experiment, the control performed the best with the lowest header pressure at 86 mm Hg compared to VII-a or IX-a. The corresponding γ-counts are also shown in the Table 6. However, in the next 4 experiments, VII-a performed the best among all the filters tested with the lowest header pressure, except in Experiment 6 where the header pressure for XI-a was slightly higher than the control. The γ-counts at the header inlet are also reflective of its performance. XI-a performed second best in this series. Experiments 4 and 5 showed some interesting results, where the control filters failed catastrophically within 8 and 10 minutes, respectively, with massive fibrin rich thrombus and complete occlusion of the filters. Table 6 shows how high the pressure was (926 and 362 mm Hg) of the control filters relative to the SMM modified filters and the corresponding high platelet count at this point. None of the SMM modified filters failed within 10 minutes in any of the experiments nor did they reach such high pressures at any point during the entire analysis.

Table 7 shows the average header pressure and the γ-count at the inlet for the control and VII-a, VIII-a, IX-a, and XI-a modified filters with the corresponding standard deviation and standard error for six experiments (n=6). The high value of the standard error (STE) for the control in comparison to any of the SMM's is also an indication of the large variability in the control filter performance. The table also indicates that the header pressures (inlet) of VII-a and XI-a had the least variability, evident from the STE values of 24 and 25 respectively. The γ-counts of the activated platelets at the header inlet (Table 7) also show a much lower STE for VII-a and XI-a compared to the control filters. Both these values are in conformity with the filter performance of VII-a and XI-a vs. control filters.

It should be noted that Experiment 5 in Table 7 shows that the header pressures of VII-a was −3 mm Hg and XI-a was −5 mm Hg. These are actual values in the in vitro analysis due to a pulsating blood flow under high shear stress through the fibers, which can result in a slight negative pressure and should actually be interpreted as '0' for all intents and purposes.

TABLE 7

| Expt. | Control | VII-a | VIII-a | IX-a | XI-a | Occlusion T min |
|---|---|---|---|---|---|---|
| Header Pressure Change - Inlet (Red) | | | | | | |
| 1 | 53 | 20 | 53 | 180 | 35 | 25 |
| 2 | 86 | 158 | 185 | 155 | 176 | 57 |
| 3 | 154 | 21 | 227 | 217 | 36 | 30 |
| 4 | 926 | 9 | 12 | 133 | 51 | 8 |
| 5 | 362 | −3 | 8 | 8 | −5 | 10 |
| 6 | 33 | 41 | 222 | 35 | 63 | 40 |
| Av | 269 | 41 | 118 | 121 | 59 | |
| STD | 343 | 59 | 105 | 83 | 62 | |
| STE | 140 | 24 | 43 | 34 | 25 | |
| Gamma Count - Inlet (Red) | | | | | | |
| 1 | 2231 | 2631 | 2667 | 3582 | 2701 | |
| 2 | 1905 | 3293 | 2623 | 2413 | 2791 | |
| 3 | 20339 | 6554 | 19816 | 19982 | 7660 | |
| 4 | 17982 | 1915 | 1941 | 6433 | 1404 | |
| 5 | 4836 | 2255 | 5577 | 905 | 1012 | |
| 6 | 2465 | 5091 | 5019 | 2280 | 3644 | |
| Av | 8293 | 3623 | 6274 | 5933 | 3202 | |
| Av/10 | 829.3 | 362 | 627 | 593 | 320 | |
| STD | 8514 | 1824 | 6791 | 7130 | 2388 | |
| STE | 3476 | 744 | 2772 | 2911 | 975 | |
| STE/10 | 348 | 74 | 277 | 291 | 97 | |

Table 8 illustrates the time to failure and the corresponding filters that failed first in each experiment. It can be seen that in Experiments 4 and 5 the control filters failed catastrophically, whereas in Experiment 1, IX-a failed in 25 minutes. In Experiments 2, 3, and 6, VIII-a failed (57, 30, and 40 minutes respectively), but none of these were major failures nor did they result in filters becoming fully occluded with thrombus. Table 8 also summarizes the header pressure of the two best SMM formulations (VII-a and XI-a) and how these compare relative to the control.

TABLE 8

| Parameters | Expt 1 | Expt 2 | Expt 3 | Expt 4 | Expt 5 | Expt 6 |
|---|---|---|---|---|---|---|
| Time to Failure minutes[1] | 25 | 57 | 30 | 8 | 10 | 40 |
| First Filter to Fail | IX-a | VIII-a | VIII-a | Control | Control | VIII-a |
| ΔP at Header (Inlet) for VII-a & XI-a Filters vs Control[2] | | | | | | |
| VII-a | 20 | 158 | 21 | 9 | −3 | 41 |
| XI-a | 35 | 176 | 36 | 51 | −5 | 63 |
| Control | 53 | 86 | 154 | 926[3] | 362[3] | 33 |

Figure 23:
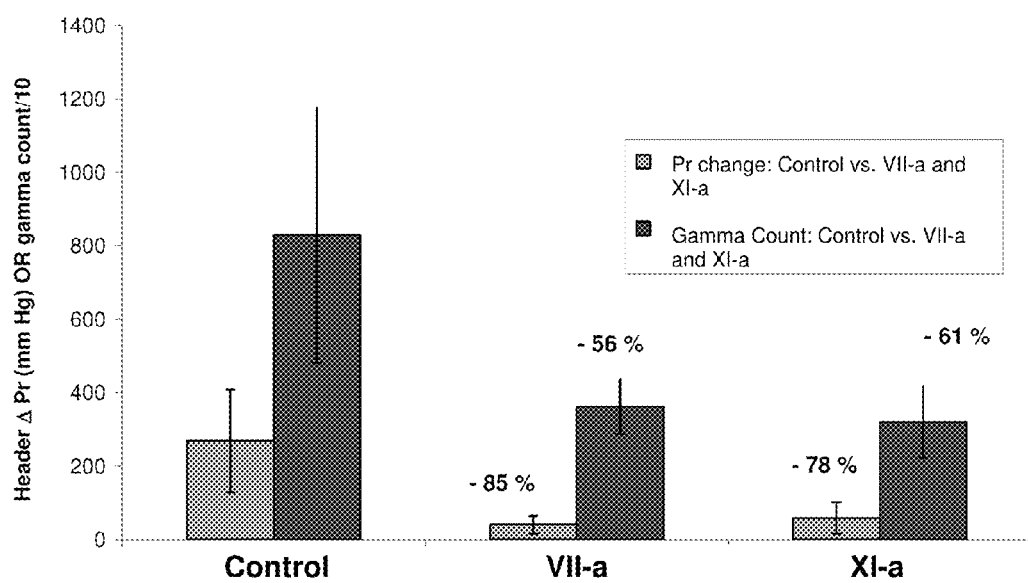
FIG. 23 is a graph showing average header pressure (ΔPr) and γ-count profiles for control versus VII-a and XI-a (n=6).
Figure 24A:
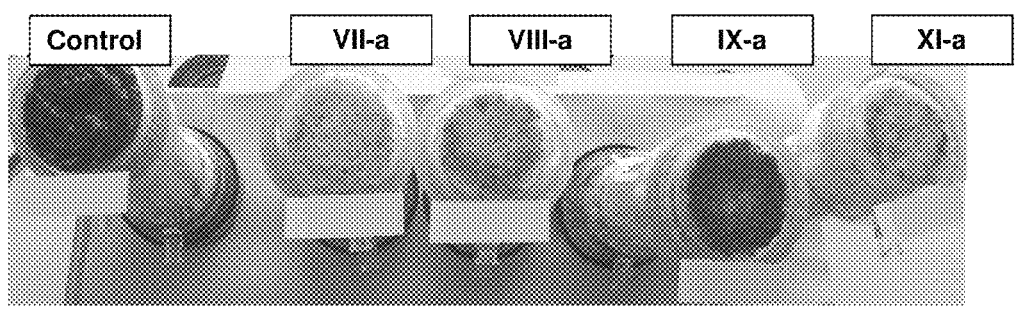
FIGS. 24A and 24B are photographs of hemofilters from Experiment 4 in Example 5, as described herein.
Figure 24B:
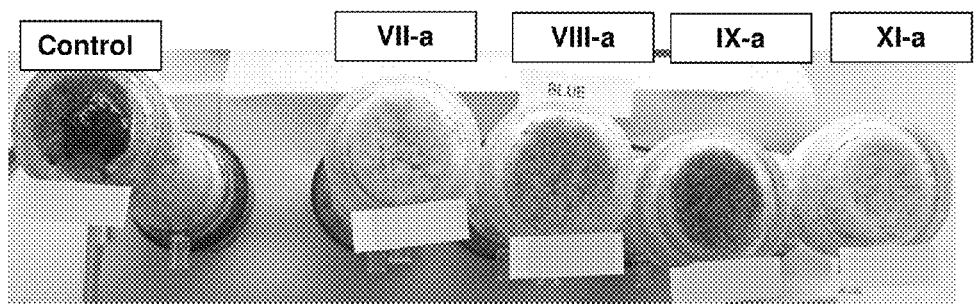
Figure 25A:
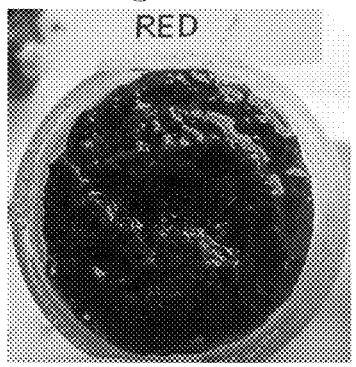
FIGS. 25A-25C are photographs from Experiment 4 in Example 5, as described herein, which show extensive coagulation.
Figure 25B:
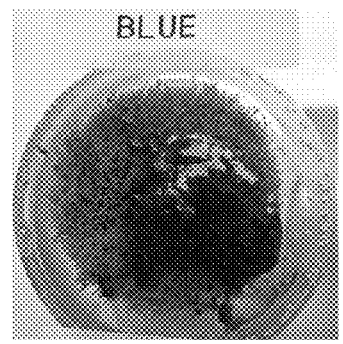
Figure 25C:
Figure 26A:
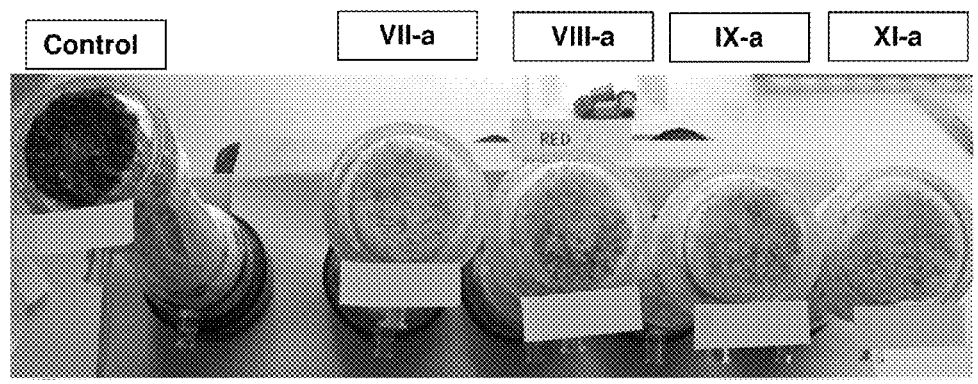
FIGS. 26A-26D are photographs of hemofilters from Experiment 5 in Example 5, as described herein.
Figure 26B:
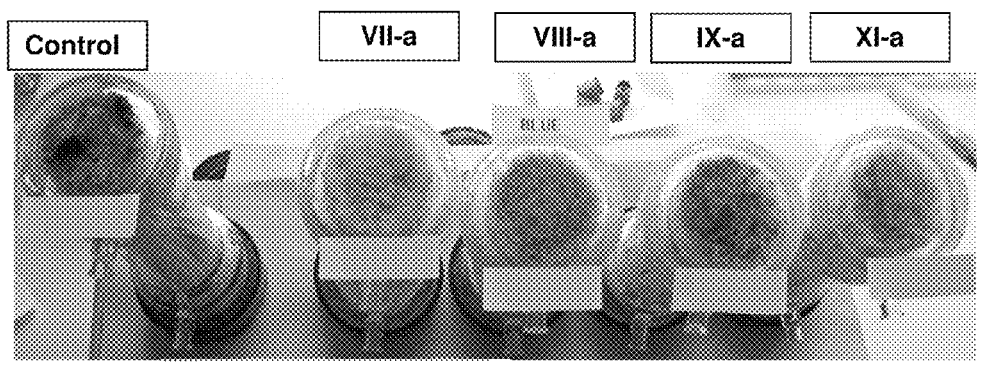
Figure 26C:
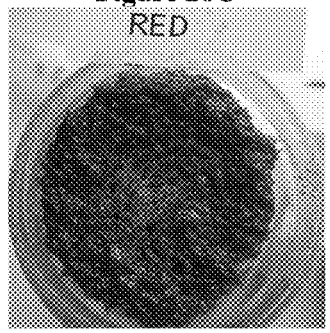
Figure 26D:
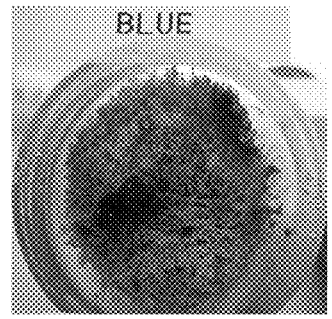

[1]Each experiment was terminated if the pressure was ≥175 mm Hg, relative to the baseline pressure. This was deemed as filter failure. Control in Expt 4 and 5 failed within 10 minutes.
[2]ΔP denote the change in header pressure relative to the baseline pressure.
[3]The filters in Expt 4 and 5 were fully occluded with thrombus FIG. 23 illustrates graphically the average header pressure and γ-counts of VII-a and XI-a in comparison to the control filters. The error bars are an indication of variability in both the pressure and γ readings; both of which are higher in the control vs. VII-a and XI-a. On average, VII-a had 85% less header pressure and XI-a had 78% less header pressure than the control while the γ-counts were 56% and 61% lower in VII-a and XI-a, respectively, as compared to the commercial control.

FIGS. 24A-24B and FIGS. 25A-25C are thrombus photos of Experiment 4, and FIGS. 26A-26D are thrombus photos of Experiment 5. In these experiments, the control filters failed within 10 minutes or less with massive thrombus formation and filter occlusion. FIGS. 24A-24B and FIGS. 25A-25C especially shows that not only the headers had thrombus but there was thrombus residue on the sieve after the draining of the blood indicative of hypercoagulation.

Figure 27:
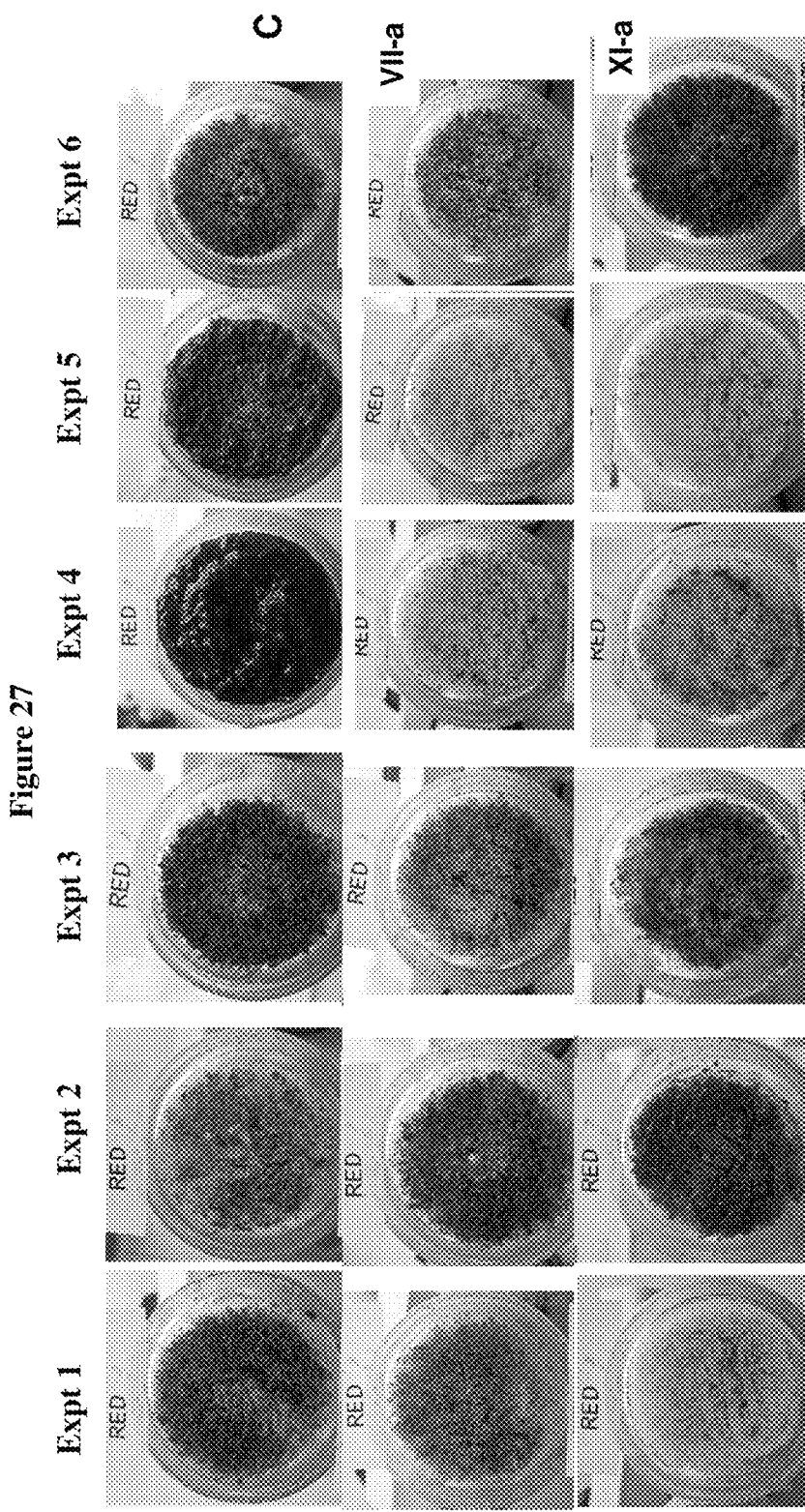
FIG. 27 shows photographs of the inlet of hemofilters from Experiment 1-6 in Example 5, as described herein. Photographs are shown for control (C, top row), VII-a (middle row), and XI-a (bottom row).

FIG. 27 compares the thrombus photos of VII-a and XI-a with control filters for all the 6 experiments. From the degree of redness of the header inlet indicative of red thrombus build-up and platelet activation, it can be seen that VII-a and XI-a on an average, performed better than the control (besides the pressure values).

Figure 28A:
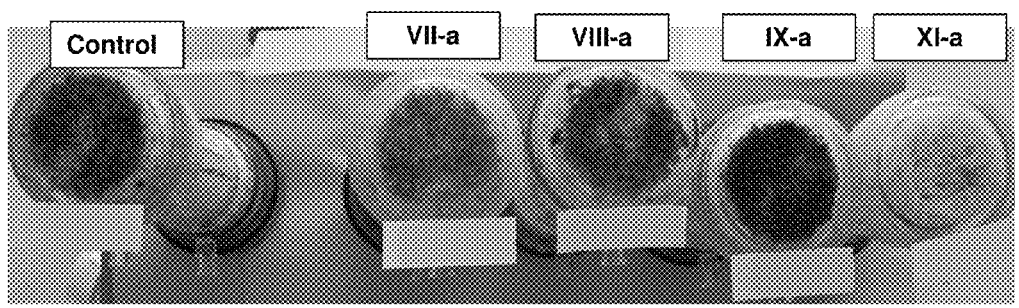
FIGS. 28A and 28B are photographs of hemofilters from Experiment 1 in Example 5, as described herein.
Figure 28B:
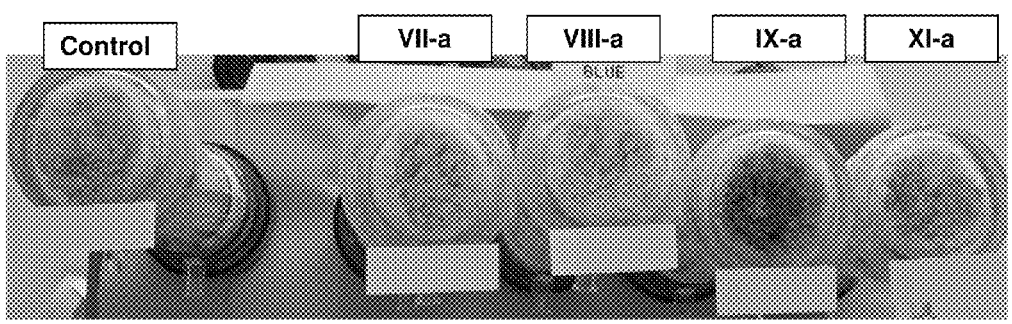
Figure 29A:
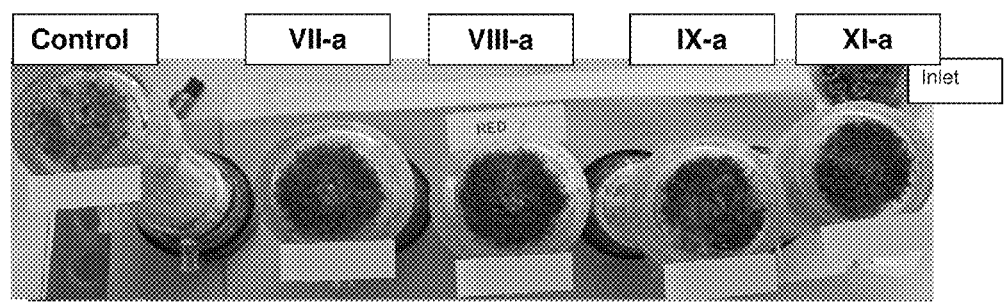
FIGS. 29A and 29B are photographs of hemofilters from Experiment 2 in Example 5, as described herein.
Figure 29B:
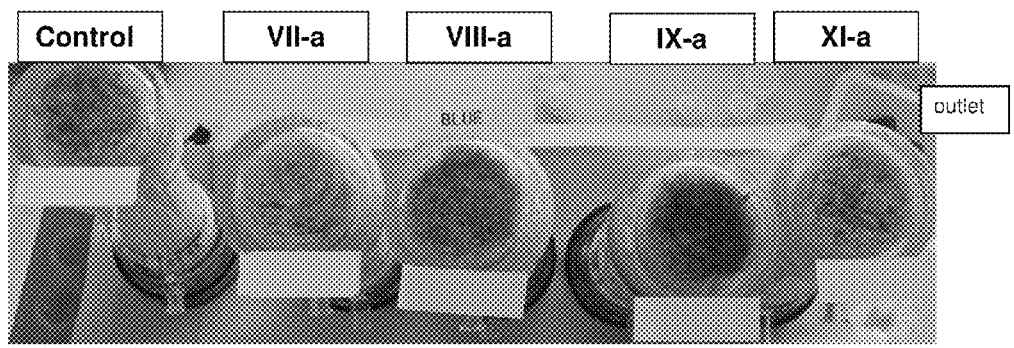
Figure 30A:
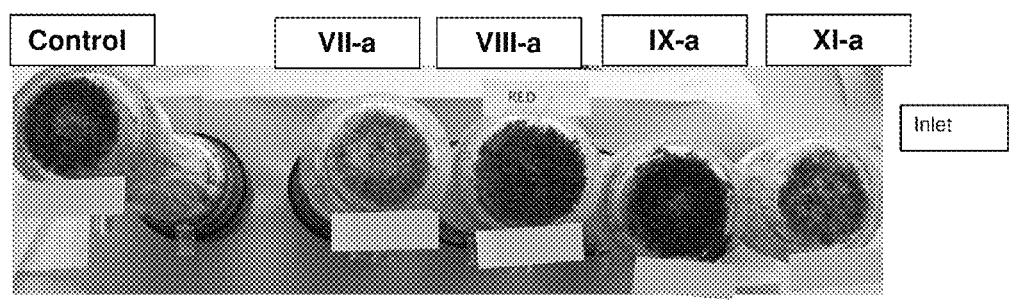
FIGS. 30A and 30B are photographs of hemofilters from Experiment 3 in Example 5, as described herein.
Figure 30B:
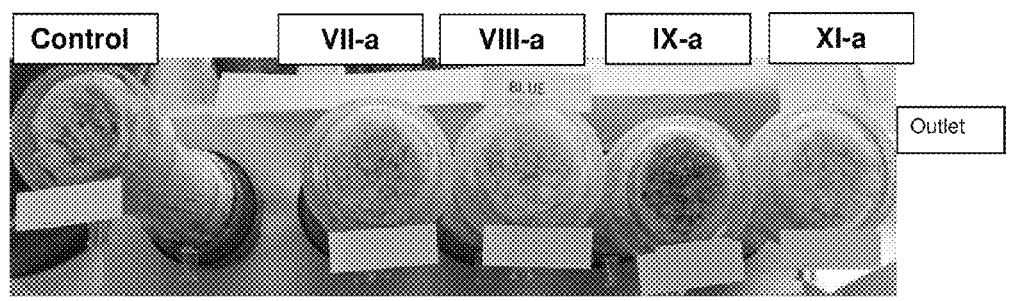
Figure 31A:
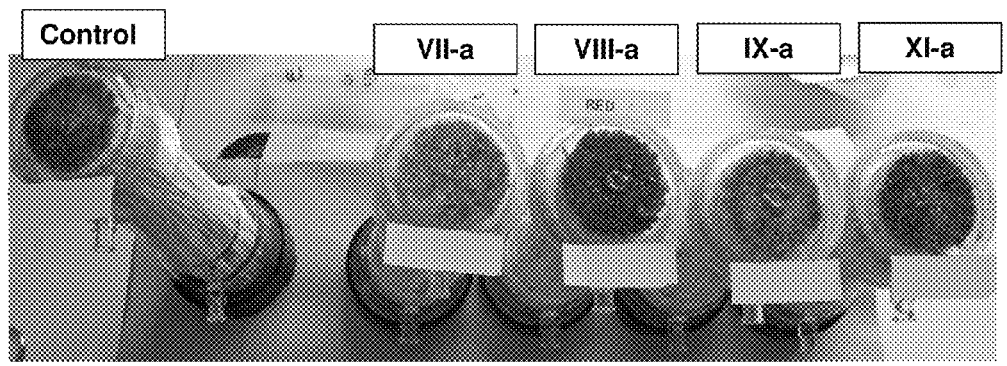
FIGS. 31A and 31B are photographs of hemofilters from Experiment 6 in Example 5, as described herein.
Figure 31B:
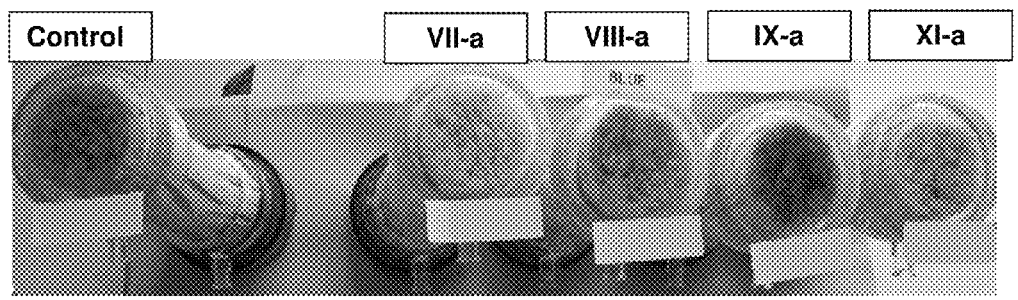

Thrombus photos were taken of the filter headers at the inlet and outlet positions after the blood loop analysis for all the 6 experiments. Experimental results are shown as thrombus photos for Experiment 1 (FIGS. 28A-28B), Experiment 2 (FIGS. 29A-29B), Experiment 3 (FIGS. 30A-30B), and Experiment 6 (FIGS. 31A-31B). In all these cases it was either VIII-a or IX-a failed, but the filters were never occluded unlike the control in experiment 4 and 5.

In addition, all the SMM modified filters (VII-a, VIII-a, IX-a, or XI-a) were able to be spun into fibers. When assembled into dialyzer filters, the hemofilters were tested, and all were able to function as a hemofilter, as compared to a control hemofilter. In general, all of the hemofilters functioned as a dialyzer.

Conclusions

The in vitro blood loop studies using heparinized bovine blood indicated that VII-a and XI-a performed the best among all the filters tested. These two formulations showed no filter failure with the lowest average header pressure (>75% less pressure), low average γ-count (>55% less), low thrombus and less thrombogenicity, than the control. Conversely, the control filters performed the worst, failing catastrophically in two experiments within 10 minutes. It also had the highest average header pressure, γ-count and variability of all the filters tested in the 6 experiments. VIII-a failed in 3 experiments and IX-a failed in 1 experiment, but all of these were within 25-57 minutes and none of the filters had any major occlusion. All of the hemofilters function as a dialyzer in various degrees and adjustments can be made easily to conform to the desired specifications.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of performing a procedure selected from hemodialysis, hemofiltration, hemoconcentration, or hemodiafiltration on a subject using a dialysis filter, wherein said filter comprises
(a) a hollow fiber membrane comprising a base polymer admixed with from 0.005% to 10% (w/w) of a surface modifying macromolecule, wherein said base polymer is a polysulfone or a polyacrylonitrile, wherein said hollow fiber membrane is antithrombogenic when contacted with blood, wherein said surface modifying macromolecule has a structure according to:
(a1) formula (VII):

$$F_T[B\text{-(Oligo)}]_n\text{-}B\text{-}F_T \qquad (VII),$$

wherein Oligo is an oligomeric segment including polypropylene oxide or polytetramethylene oxide and having a theoretical molecular weight of from 500 to 3,000 Daltons; B is a hard segment formed from hexamethylene diisocyanate; $F_T$ is a polyfluoroorgano group; and n is an integer from 1 to 10;
(a2) formula (VIII):

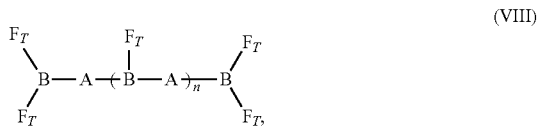

(VIII)

wherein A is an oligomeric segment including polytetramethylene oxide and having a theoretical molecular weight of from 500 to 3,000 Daltons; B is a hard segment formed from hexamethylene diisocyanate biuret trimer; $F_T$ is a polyfluoroorgano group; and n is an integer from 0 to 10;
(a3) formula (IX):

$$F_T\text{-}[B\text{-(Oligo)}]_n\text{-}B\text{-}F_T \qquad (IX),$$

wherein Oligo is an oligomeric segment including poly (2,2 dimethyl-1,3-propylcarbonate and having a theoretical molecular weight of from 500 to 3,000 Daltons; B is a hard segment formed from 4,4'-methylene bis(cyclohexyl isocyanate); $F_T$ is a polyfluoroorgano group; and n is an integer from 1 to 10; or
(a4) formula (XI):

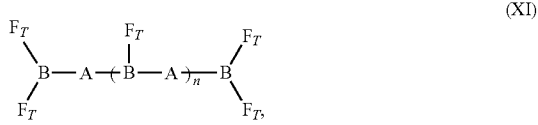

(XI)

wherein A is a block copolymer comprising polypropylene oxide and polydimethylsiloxane and having a theoretical molecular weight of from 1,000 to 5,000 Daltons; B is a hard segment formed from hexamethylene diisocyanate biuret trimer; $F_T$ is a polyfluoroorgano group; and n is an integer from 1 to 10;
(a5) formula (IV), $$F_T\text{-}[B\text{-}A]_n\text{-}B\text{-}F_T \qquad (IV),$$

wherein A is a soft segment including hydrogenated polybutadiene, poly (2,2 dimethyl-1,3-propylcarbonate), polybutadiene, poly (diethylene glycol)adipate, poly (hexamethylene carbonate), poly (ethylene-cobutylene), neopentyl glycol-ortho phthalic anhydride polyester, diethylene glycol-ortho phthalic anhydride polyester, 1,6-hexanediol-ortho phthalic anhydride polyester, or bisphenol A ethoxvlate; B is a hard segment including a urethane; $F_T$ is a polvfluoroorgano group, and n is an integer from 1to 10; and/or
  (b) a potted bundle of hollow fiber membranes within an encasement comprising:
    (i) an array of hollow fiber membranes, said array of hollow fiber membranes having lumens, a first set of fiber ends, and a second set of fiber ends;
    (ii) said first set of fiber ends being potted in a potting resin which defines a first internal wall near a first end of the encasement; and
    (iii) said second set of fiber ends being potted in a potting resin which defines a second internal wall near a second end of the encasement,
    wherein said lumens of said hollow fiber membranes provide a path for the flow of blood from said first internal wall to said second internal wall, and
    wherein said potting resin comprises from 0.005% to 10% (w/w) of a surface modifying macromolecule having a structure according to:
    (b 1) formula (III),

$$F_T\text{[B-(oligo)]}_n\text{-B-}F_T \qquad (III),$$

wherein B includes a urethane; oligo includes polypropylene oxide, polyethylene oxide, or polytetramethylene oxide; $F_T$ is a polyfluoroorgano group; and n is an integer from 1 to 10;
    (b2) formula (VII),

$$F_T\text{[B-(Oligo)]}_n\text{-B-}F_T \qquad (VII),$$

wherein Oligo is an oligomeric segment including polypropylene oxide, polyethylene oxide, or polytetramethylene oxide and having a theoretical molecular weight of from 500 to 3,000 Daltons; B is a hard segment formed from an isocyanate dimer; $F_T$ is a polvfluoroorgano group; and n is an integer from 1to 10; or
    (b3) formula (IV),

$$F_T\text{[B-A]}_n\text{-B-}F_T \qquad (IV),$$

wherein A is a soft segment including hydrogenated polybutadiene, poly (2,2 dimethyl-1,3-propylcarbonate), polybutadiene, poly (diethylene glycol)adipate, poly (hexamethylene carbonate), poly (ethylene-co-butylene), neopentyl glycol-ortho phthalic anhydride polyester, diethylene glycol-ortho phthalic anhydride polyester, 1,6-hexanediol-ortho phthalic anhydride polyester, or bisphenol A ethoxylate; B is a hard segment including a urethane; $F_T$ is a polyfluoroorgano group, and n is an integer from 1 to 10.

2. The method of claim 1, wherein during said procedure said subject receives less than a standard dose of anticoagulant or receives no anticoagulant.

3. The method of claim 1, wherein said filter has a prolonged working life, wherein said filter has an increased average functional working life of at least 125%, wherein the thrombi deposition on said filter is reduced by at least 10% when contacted with blood, wherein said filter has an operating pressure after 4 hours of use that is reduced by at least 10 %, or wherein the adverse events experienced by said subject are reduced.

4. The method of claim 1, wherein said filter comprises said hollow fiber membrane, said hollow fiber membrane comprising a surface modifying macromolecule having a structure according to formula VII-a, VIII-a, IX-a, and XI-a.

5. The method of claim 1, wherein said filter comprises said potted bundle, said potted bundle comprising a potting resin that comprises a surface modifying macromolecule selected from VII-a, VIII-a, IX-a, XI-a, VIII-b, VIII-d, and XI-b.

6. The method of claim 1, wherein said filter comprises said hollow fiber membrane comprising said surface modifying macromolecule,
  wherein the thrombi deposition on said surface said hollow fiber membrane is reduced by at least 10% when contacted with blood,
  wherein said hollow fiber membrane has an operating pressure after 4 hours of use that is reduced by at least 10%, or
  wherein said hollow fiber membrane reduces adverse advents in a subject receiving blood passing through said hollow fiber membrane.

7. The method of claim 1, wherein said filter comprises said hollow fiber membrane comprising said surface modifying macromolecule admixed with said base polymer, wherein said base polymer is a polysulfone.

8. The method of claim 7, wherein said polysulfone is poly(oxy-1,4-phenylene sulfonyl-1,4-phenyleneoxy-1,4-phenyleneisopropylidene-1,4-phenylene) or polyether sulfone.

9. The method of claim 1, wherein said filter comprises said hollow fiber membrane, said hollow fiber membrane further comprising a hydrophilic pore forming agent 10. The method of claim 9, wherein said hydrophilic pore forming agent is selected from polyvinylpyrrolidone, ethylene glycol, alcohols, polypropylene glycol, and polyethylene glycol, or mixtures thereof.

11. The method of claim 9, wherein said hollow fiber membrane comprises from 80% to 96.5% (w/w) of said base polymer, from 3% to 20% (w/w) of said hydrophilic pore forming agent, and 0.005% to 10% (w/w) of said surface modifying macromolecule.

12. The method of claim 1, wherein said filter comprises said potted bundle,
  wherein said potted bundle has a prolonged working life,
  wherein said bundle has an increased average functional working life of at least 125%,
  wherein the thrombi deposition on said potted bundle is reduced by at least 10% when contacted with blood,
  wherein said bundle has an operating pressure after 4 hours of use that is reduced by at least 10%,
  wherein said potting resin is antithrombogenic when contacted with blood, or
  wherein said potted bundle reduces adverse advents in a subject receiving blood passing through said potted bundle.

13. The method of claim 1, wherein said filter comprises said bundle of potted hollow fiber membranes, wherein said bundle of potted hollow fiber membranes within an encasement is part of a blood purification device.

14. The method of claim 13, wherein said blood purification device is a hemodialysis, hemodiafiltration, hemofiltration or hemoconcentration device.

15. The method of claim 1, wherein said filter comprises said potted bundle, wherein said potting resin comprises a cross-linked polyurethane.

16. The method of claim 1, wherein said filter comprises said hollow fiber membrame, said hollow fiber membrane comprising a surface modifying macromolecule having a structure according to formula (VII),

   (VII), wherein
(i) Oligo is an oligomeric segment including polypropylene oxide or polytetramethylene oxide having a theoretical molecular weight of from 500 to 3,000 Daltons;
(ii) B is a hard segment formed from hexamethylene diisocyanate;
(iii) $F_T$ is a polyfluoroorgano group; and
(iv) n is an integer from 1 to 10.

17. The method of claim 16, wherein n is an integer from 1 to 3.

18. The method of claim 17, wherein $F_T$ is selected from the group consisting of $CH_mF_{(3-m)}(CF_2)_rCH_2CH_2$- and $CH_mF_{(3-m)}(CF_2)_s(CH_2CH_2O)_x$—,
wherein m is 0, 1, 2, or 3; r is an integer from 2 to 20; s is an integer from 1 to 20; and x is an integer from 1 to 10.

19. The method of claim 16, wherein said surface modifying macromolecule of formula (VII) is VII-a.

20. The method of claim 1, wherein said filter comprises said potted bundle, said potted bundle comprising a surface modifying macromolecule having a structure according to formula (III),

   (III)

wherein
(i) B includes a urethane;
(ii) oligo includes polypropylene oxide, polyethylene oxide, or polytetramethylene oxide;
(iii) $F_T$ is a polyfluoroorgano group; and
(iv) n is an integer from 1 to 10.

21. The method of claim 1, wherein said filter comprises said potted bundle, said potted bundle comprising a surface modifying macromolecule having a structure according to formula (VII),

   (VII), wherein
(i) Oligo is an oligomeric segment including polypropylene oxide, polyethylene oxide, or polytetramethylene oxide and having a theoretical molecular weight of from 500 to 3,000 Daltons;
(ii) B is a hard segment formed from an isocyanate dimer;
(iii) $F_T$ is a polyfluoroorgano group; and
(iv) n is an integer from 1 to 10.

22. The method of claim 1, wherein said filter comprises said potted bundle, said potted bundle comprising a surface modifying macromolecule having a structure according to formula (IV),

   (IV)

wherein
A is a soft segment including hydrogenated polybutadiene, poly (2,2 dimethyl-1,3-propylcarbonate), polybutadiene, poly (diethylene glycol)adipate, poly (hexamethylene carbonate), poly (ethylene-co-butylene), neopentyl glycol-ortho phthalic anhydride polyester, diethylene glycol-ortho phthalic anhydride polyester, 1,6-hexanediol-ortho phthalic anhydride polyester, or bisphenol A ethoxylate;
(ii) B is a hard segment including a urethane; and
(iii) $F_T$ is a polyfluoroorgano group, and
(iv) n is an integer from 1 to 10.

23. The method of claim 1, wherein said filter comprises said hollow fiber membrane, said hollow fiber membrane comprising a surface modifying macromolecule having a structure according to formula (XI),

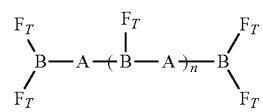   (XI)

wherein
(i) A is a block copolymer comprising polypropylene oxide and polydimethylsiloxane having a theoretical molecular weight of from 1,000 to 5,000 Daltons;
(ii) B is a hard segment formed from hexamethylene diisocyanate biuret trimer;
(iii) $F_T$ is a polyfluoroorgano group; and
(iv) n is 0, 1, 2, or 3.

24. The method of claim 23, wherein said hollow fiber membrane comprises a surface modifying macromolecule having a structure according to formula XI-a.

25. The method of claim 1, wherein said filter comprises said hollow fiber membrane, said hollow fiber membrane comprising a surface modifying macromolecule having a structure according to formula (VIII),

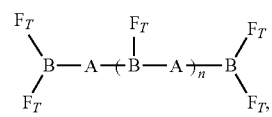   (VIII)

wherein
(i) A is an oligomeric segment including polytetramethylene oxide and having a theoretical molecular weight of from 500 to 3,000 Daltons;
(ii) B is a hard segment formed from hexamethylene diisocyanate biuret trimer;
(iii) $F_T$ is a polyfluoroorgano group; and
(iv) n is 0, 1, 2, or 3.

26. The method of claim 1, wherein said hollow fiber membrane comprises a surface modifying macromolecule having a structure according to formula VIII-a.

27. The method of claim 1, wherein said filter comprises said hollow fiber membrane, said hollow fiber membrane comprising a surface modifying macromolecule having a structure according to formula (IX),

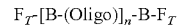   (IX), wherein
(i) Oligo is an oligomeric segment including poly (2,2dimethyl-1,3propylcarbonate and having a theoretical molecular weight of from 500 to 3,000 Daltons;
(ii) B is a hard segment formed from 4,4'-methylene bis (cyclohexyl isocyanate);
(iii) $F_T$ is a polyfluoroorgano group; and
(iv) n is 0, 1, 2, or 3.

28. The method of claim 27, wherein said hollow fiber membrane comprises a surface modifying macromolecule having a structure according to formula IX-a.

29. The method of claim 1, wherein said filter comprises said hollow fiber membrane, wherein $F_T$ is selected from the group consisting of $CH_mF_{(3-m)}(CF_2)_rCH_2CH_2$- and $CH_mF_{(3-m)}(CF_2)_s(CH_2CH_2O)_x$—, wherein m is 0, 1, 2, or 3; r is an integer from 2 to 20; s is an integer from 1 to 20; and x is an integer from 1 to 10.

30. A method of performing a procedure selected from hemodialysis, hemofiltration, hemoconcentration, or hemodiafiltration on a subject using a dialysis filter, wherein said filter comprises a hollow fiber membrane comprising a base polymer admixed with from 0.005% to 10% (w/w) of a surface modifying macromolecule, wherein said hollow fiber membrane is antithrombogenic when contacted with blood, wherein said surface modifying macromolecule has a structure according to:

(a1) formula (VII):

  (VII), wherein Oligo is an oligomeric segment including polypropylene oxide or polytetramethylene oxide and having a theoretical molecular weight of from 500 to 3,000 Daltons; B is a hard segment formed from hexamethylene diisocyanate; $F_T$ is a polyfluoroorgano group; and n is an integer from 1 to 10;

(a2) formula (VIII):

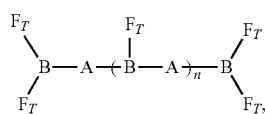  (VIII)

wherein A is an oligomeric segment including polytetramethylene oxide and having a theoretical molecular weight of from 500 to 3,000 Daltons; B is a hard segment formed from hexamethylene diisocyanate biuret trimer; $F_T$ is a polyfluoroorgano group; and n is an integer from 0 to 10;

(a3) formula (IX):

  (IX), wherein Oligo is an oligomeric segment including poly(2,2dimethyl-1,3-propylcarbonate and having a theoretical molecular weight of from 500 to 3,000 Daltons; B is a hard segment formed from 4,4'-methylene bis(cyclohexyl isocyanate); $F_T$ is a polyfluoroorgano group; and n is an integer from 1 to 10; or (a4) formula (XI):

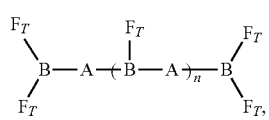  (XI)

wherein A is a block copolymer comprising polypropylene oxide and polydimethylsiloxane and having a theoretical molecular weight of from 1,000 to 5,000 Daltons; B is a hard segment formed from hexamethylene diisocyanate biuret trimer $F_T$ is a polyfluoroorgano group; and n is an integer from 1 to 10;

wherein the blood and dialysate are separated from each other by said hollow fiber membrane at a semipermeable surface of said hollow fiber membrane during said procedure, said semipermeable surface comprising said surface modifying macromolecule.

31. The method of claim 30, wherein said surface modifying macromolecule has a structure according to formula (VII):

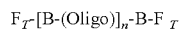  (VII), wherein Oligo is an oligomeric segment including polypropylene oxide, polyethylene oxide, or polytetramethylene oxide and having a theoretical molecular weight of from 500 to 3,000 Daltons; B is a hard segment formed from hexamethylene diisocyanate; $F_T$ is a polyfluoroorgano group; and n is an integer from 1 to 10.

32. The method of claim 31, wherein n is an integer from 1 to 3.

33. The method of claim 32, wherein Oligo is an oligomeric segment including polypropylene oxide.

34. The method of claim 32, wherein Oligo is an oligomeric segment including polytetramethylene oxide.

35. The method of claim 32, wherein $F_T$ is selected from the group consisting of $CH_mF_{(3-m)}CF_2)_rCH_2CH_2$- and $CH_mF_{(3-m)}(CF_2)_s(CH_2CH_2O)_x$—, wherein m is 0, 1, 2, or 3; r is an integer from 2 to 20; s is an integer from 1 to 20; and X is an integer from 1 to 10.

36. A method of performing a procedure selected from hemodialysis, hemofiltration, hemoconcentration, or hemodiafiltration on a subject using a dialysis filter, wherein said filter comprises a hollow fiber membrane comprising a base polymer admixed with from 0.005% to 10% (w/w) of a surface modifying macromolecule, wherein said hollow fiber membrane is antithrombogenic when contacted with blood, wherein said surface modifying macromolecule has a structure according to:

(a1) formula (VII):

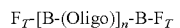  (VII), wherein Oligo is an oligomeric segment including polypropylene oxide or polytetramethylene oxide and having a theoretical molecular weight of from 500 to 3,000 Daltons; B is a hard segment formed from hexamethylene diisocyanate; $F_T$ is a polyfluoroorgano group; and n is an integer from 1 to 10;

(a2) formula (VIII):

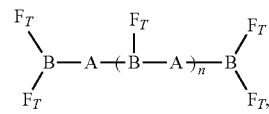  (VIII)

wherein A is an oligomeric segment including polytetramethylene oxide and having a theoretical molecular weight of from 500 to 3,000 Daltons; B is a hard segment formed from hexamethylene diisocyanate biuret trimer; $F_T$ is a polyfluoroorgano group; and n is an integer from 0 to 10;

(a3) formula (IX):

  (IX), wherein Oligo is an oligomeric segment including poly(2,2dimethyl-1,3-propylcarbonate and having a theoretical molecular weight of from 500 to 3,000 Daltons; B is a hard segment formed from 4,4'-methylene bis(cyclohexyl isocyanate); $F_T$ is a polyfluoroorgano group; and n is an integer from 1 to 10; or (4) formula (XI):

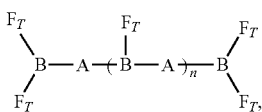 (XI)

wherein A is a block copolymer comprising polypropylene oxide and polydimethylsiloxane and having a theoretical molecular weight of from 1,000 to 5,000 Daltons; B is a hard segment formed from hexamethylene diisocyanate biuret trimer; $F_T$ is a polyfluoroorgano group; and n is an integer from 1 to 10;

wherein said hollow fiber membrane is formed from a spinning solution by extruding said spinning solution through a tube-in-tube type orifice, wherein said spinning solution comprises said base polymer and said surface-modifying macromolecule.

37. The method of claim 36, wherein said surface modifying macromolecule has a structure according to formula (VII):

$$F_T\text{-}[B\text{-}(Oligo)]_n\text{-}B\text{-}F_T \qquad (VII),$$

wherein Oligo is an oligomeric segment including polypropylene oxide or polytetramethylene oxide and having a theoretical molecular weight of from 500 to 3,000 Daltons; B is a hard segment formed from hexamethylene diisocyanate; $F_T$ is a polyfluoroorgano group; and n is an integer from 1 to 10.

38. The method of claim 37, wherein n is an integer from 1 to 3.

39. The method of claim 38, wherein Oligo is an oligomeric segment including polypropylene oxide.

40. The method of claim 38, wherein Oligo is an oligomeric segment including polytetramethylene oxide.

41. The method of claim 38, wherein $F_T$ is selected from the group consisting of $CH_mF_{(3-m)}(CF_2)_rCH_2CH_2$- and $CH_mF_{(3-m)}(CF_2)_s(CH_2CH_2O)_x$—, wherein m is 0, 1, 2, or 3; r is an integer from 2 to 20; s is an integer from 1 to 20; and x is an integer from 1 to 10.

* * * * *

UNITED STATES PATENT AND TRADEMARK OFFICE
CERTIFICATE OF CORRECTION

PATENT NO. : 8,877,062 B2  Page 1 of 1
APPLICATION NO. : 12/834730
DATED : November 4, 2014
INVENTOR(S) : Mullick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 481 days.

Signed and Sealed this
Sixth Day of June, 2017

Michelle K. Lee
*Director of the United States Patent and Trademark Office*